US012576169B2

(12) United States Patent
Di Carlo et al.

(10) Patent No.: US 12,576,169 B2
(45) Date of Patent: Mar. 17, 2026

(54) SILICON-FLUORIDE ACCEPTOR SUBSTITUTED RADIOPHARMACEUTICALS AND PRECURSORS THEREOF

(71) Applicant: Technische Universität München, Munich (DE)

(72) Inventors: Daniel Di Carlo, Haimhausen (DE); Hans-Jürgen Wester, Schweitenkirchen/Sünzhausen (DE)

(73) Assignee: Technische Universität München, Munich (DE)

( * ) Notice: Subject to any disclaimer, the term of this patent is extended or adjusted under 35 U.S.C. 154(b) by 1154 days.

(21) Appl. No.: 17/425,430

(22) PCT Filed: Jan. 29, 2020

(86) PCT No.: PCT/EP2020/052159
§ 371 (c)(1),
(2) Date: Jul. 23, 2021

(87) PCT Pub. No.: WO2020/157128
PCT Pub. Date: Aug. 6, 2020

(65) Prior Publication Data
US 2022/0096669 A1 Mar. 31, 2022

(30) Foreign Application Priority Data
Jan. 30, 2019 (EP) .................................... 19154636

(51) Int. Cl.
*A61K 51/04* (2006.01)

(52) U.S. Cl.
CPC ...... *A61K 51/0489* (2013.01); *A61K 51/0402* (2013.01)

(58) Field of Classification Search
None
See application file for complete search history.

(56) References Cited

U.S. PATENT DOCUMENTS

2017/0246327 A1* 8/2017 Kopka .................. A61K 51/06

FOREIGN PATENT DOCUMENTS

WO WO 2019/020831 1/2019

OTHER PUBLICATIONS

Litau et al (Next Generation of SiFAlin-Based TATE Derivatives for PET Imaging of SSTR-Positive Tumors: Influence of Molecular Design on In Vitro SSTR Binding and In Vivo Pharmacokinetics. Bioconjugate Chem. 2015, 26, 2350-2359). (Year: 2015).*
Bernard-Gauthier V et al., $^{18}$F-labeled silicon-based fluoride acceptors: potential opportunities for novel positron emitting radiopharmaceuticals, BioMed Research International, 1-20 (2014).
Niedermoser S, et al., In Vivo Evaluation of $^{18}$F-SiFAlin-Modified TATE: a Potential Challenge for $^{68}$Ga-DOTATATE, the Clinical Gold Standard for Somatostatin Receptor Imaging with PET, Journal of Nuclear Medicine, 56, 1100-05 (2015).
Wängler C, et al., One-step $^{18}$F-labeling of carbohydrate-conjugated octreotate-derivatives containing a silicon-fluoride-acceptor (SiFA): in vitro and in vivo evaluation as tumor imaging agents for positron emission tomography (PET), Bioconjugate Chemistry, 21, 2289-96 (2010).
Dialer et al., "Studies toward the Development of New Silicon-Containing Building Blocks for the Direct 18 F-Labeling of Peptides," *Journal of Medicinal Chemistry*, 56(19):7552-7563, 2013.
Kiess et al., "Prostate-specific membrane antigen as a target for cancer imaging and therapy," *The Quarterly Journal of Nuclear Medicine and Molecular Imaging*, 59(3):241-268, 2015.
Lindner et al., "Synthesis and in Vitro and in Vivo Evaluation of SiFA-Tagged Bombesin and RGD Peptides as Tumor Imaging Probes for Positron Emission Tomography," *Bioconjugate Chemistry*, 25(4):738-749, 2014.

(Continued)

*Primary Examiner* — Jake M Vu
(74) *Attorney, Agent, or Firm* — pH IP Law

(57) ABSTRACT

A ligand-SiFA conjugate compound represented by formula (1) wherein: $R^L$ is a ligand moiety which is capable of binding to prostate-specific membrane antigen (PSMA); $R^{SiFA}$ is a silicon-fluoride acceptor (SiFA) moiety which can be labeled with $^{18}$F or which is labeled with $^{18}$F; L is a linking moiety; $R^H$ is a hydrophilic moiety which comprises (i) a linear or branched sequence of 2 to 10 hydrophilic amino acid units $A^H$, each of which is independently derived from a natural or non-natural amino acid carrying a hydrophilic side chain, and optionally one amino acid unit $A^N$ derived from a natural or non-natural amino acid which is devoid of a hydrophilic side chain, wherein the hydrophilic amino acid units and, if present, the unit $A^N$, are bound to each other via a direct covalent bond or via a coupling unit; and which optionally further comprises (ii) one or more hydrophilic residues $R^T$, each of which may be bound to an amino group, a carboxylic acid group, or to a hydrophilic side chain of an amino acid unit; or a pharmaceutically acceptable salt thereof.

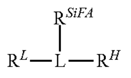

(1)

16 Claims, 7 Drawing Sheets

(56) References Cited

OTHER PUBLICATIONS

Litau et al., "Next Generation of SiFA lin-Based TATE Derivatives for PET Imaging of SSTR-Positive Tumors: Influence of Molecular Design on In Vitro SSTR Binding and In Vivo Pharmacokinetics," *Bioconjugate Chemistry*, 26(12):2350-2359, 2015.
PCT International Search Report and Written Opinion issued in International Application No. PCT/EP2020/052159, mailed Apr. 30, 2020.

* cited by examiner

| biodistribution of [$^{18}$F]01 a | |
|---|---|
| organ | %ID/g |
| blood | 0.97 ± 0.18 |
| heart | 1.10 ± 0.08 |
| lung | 1.83 ± 0.28 |
| liver | 0.92 ± 0.09 |
| spleen | 25.94 ± 12.04 |
| pancreas | 0.77 ± 0.22 |
| stomach | 0.55 ± 0.23 |
| intestine | 0.57 ± 0.12 |
| kidney | 214.23 ± 19.05 |
| adrenal gland | 5.38 ± 3.23 |
| muscle | 0.40 ± 0.25 |
| bone | 1.15 ± 0.33 |
| tumor | 15.02 ± 3.32 |
| salivary gland | 1.63 ± 0.35 |

| biodistribution of [$^{18}$F]01 d | |
|---|---|
| organ | %ID/g |
| blood | 0.94 ± 0.30 |
| heart | 0.94 ± 0.28 |
| lung | 1.78 ± 0.45 |
| liver | 0.91 ± 0.24 |
| spleen | 31.70 ± 16.91 |
| pancreas | 0.56 ± 0.09 |
| stomach | 0.40 ± 0.13 |
| intestine | 0.54 ± 0.15 |
| kidney | 164.12 ± 70.02 |
| adrenal gland | 5.72 ± 2.63 |
| muscle | 0.42 ± 0.15 |
| bone | 1.77 ± 0.46 |
| tumor | 14.30 ± 5.11 |
| salivary gland | 2.04 ± 0.70 |

| biodistribution of [$^{18}$F]02 c | |
|---|---|
| organ | %ID/g |
| blood | 1.33 ± 0.08 |
| heart | 0.76 ± 0.17 |
| lung | 1.04 ± 0.06 |
| liver | 1.57 ± 0.20 |
| spleen | 11.49 ± 2.42 |
| pancreas | 0.40 ± 0.08 |
| stomach | 0.44 ± 0.07 |
| intestine | 0.53 ± 0.09 |
| kidney | 160.88 ± 22.44 |
| adrenal gland | 14.94 ± 11.41 |
| muscle | 0.19 ± 0.03 |
| bone | 0.74 ± 0.21 |
| tumor | 8.93 ± 1.76 |
| salivary gland | 1.50 ± 0.16 |

| biodistribution of [$^{18}$F]03 f | |
|---|---|
| organ | %ID/g |
| blood | 0.96 ± 0.60 |
| heart | 0.55 ± 0.33 |
| lung | 1.24 ± 0.55 |
| liver | 0.51 ± 0.21 |
| spleen | 10.98 ± 6.14 |
| pancreas | 0.29 ± 0.06 |
| stomach | 0.60 ± 0.38 |
| intestine | 0.47 ± 0.12 |
| kidney | 119.52 ± 24.29 |
| adrenal gland | 2.40 ± 0.71 |
| muscle | 0.23 ± 0.12 |
| bone | 2.07 ± 0.60 |
| tumor | 7.03 ± 1.83 |
| salivary gland | 1.25 ± 0.47 |

| biodistribution of [$^{18}$F]06 | |
|---|---|
| organ | %ID/g |
| blood | 0.41 ± 0.05 |
| heart | 0.51 ± 0.14 |
| lung | 1.16 ± 0.21 |
| liver | 0.35 ± 0.04 |
| spleen | 19.92 ± 6.45 |
| pancreas | 0.42 ± 0.14 |
| stomach | 0.23 ± 0.07 |
| intestine | 0.26 ± 0.01 |
| kidney | 184.44 ± 33.05 |
| adrenal gland | 2.23 ± 0.73 |
| muscle | 0.43 ± 0.50 |
| bone | 0.49 ± 0.33 |
| tumor | 8.82 ± 2.33 |
| salivary gland | 1.35 ± 0.32 |

| biodistribution of [$^{18}$F]07 | |
|---|---|
| organ | %ID/g |
| blood | 1.09 ± 0.76 |
| heart | 0.75 ± 0.42 |
| lung | 1.32 ± 0.72 |
| liver | 0.90 ± 0.30 |
| spleen | 5.23 ± 3.99 |
| pancreas | 0.37 ± 0.22 |
| stomach | 0.43 ± 0.24 |
| intestine | 0.60 ± 0.28 |
| kidney | 201.51 ± 14.72 |
| adrenal gland | 1.63 ± 0.67 |
| muscle | 0.20 ± 0.10 |
| bone | 1.87 ± 0.88 |
| tumor | 6.23 ± 2.01 |
| salivary gland | 0.76 ± 0.49 |

SILICON-FLUORIDE ACCEPTOR SUBSTITUTED RADIOPHARMACEUTICALS AND PRECURSORS THEREOF

The present application is a national phase application under 35 U.S.C. § 371 of International Application No. PCT/EP2020/052159, filed Jan. 29, 2020, which claims the priority benefit of European Application No. 19154636.5, filed Jan. 30, 2019, the entire contents of each of which are hereby incorporated by reference.

The present invention relates to silicon-fluoride acceptor (SiFA) substituted radiopharmaceuticals and precursors thereof which are suitable in the diagnosis and the treatment of prostate cancer.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

BACKGROUND OF THE INVENTION

Prostate Cancer and PSMA

Prostate Cancer (PCa) remained over the last decades the most common malignant disease in men with high incidence and poor survival rates. Due to its overexpression in prostate cancer (Silver, D. A., et al., *Prostate-specific membrane antigen expression in normal and malignant human tissues*. Clinical Cancer Research, 1997. 3(1): p. 81-85), prostate-specific membrane antigen (PSMA) or glutamate carboxypeptidase II (GCP II) proved its eligibility as excellent target for the development of highly sensitive radiolabeled agents for endoradiotherapy and imaging of PCa (Afshar-Oromieh, A., et al., *The diagnostic value of PET/CT imaging with the $^{68}$Ga-labelled PSMA ligand HBED-CC in the diagnosis of recurrent prostate cancer*. European journal of nuclear medicine and molecular imaging, 2015. 42(2): p. 197-209; Benešová, M., et al., *Preclinical Evaluation of a Tailor-Made DOTA-Conjugated PSMA Inhibitor with Optimized Linker Moiety for Imaging and Endoradiotherapy of Prostate Cancer*. Journal of Nuclear Medicine, 2015. 56(6): p. 914-920; Robu, S., et al., *Preclinical evaluation and first patient application of $^{99m}$Tc-PSMA-I&S for SPECT imaging and radioguided surgery in prostate cancer*. Journal of Nuclear Medicine, 2016: p. jnumed. 116.178939; Weineisen, M., et al., *Development and first in human evaluation of PSMA I&T—A ligand for diagnostic imaging and endoradiotherapy of prostate cancer*. Journal of Nuclear Medicine, 2014. 55 (supplement 1): p. 1083-1083; Rowe, S., et al., *PET imaging of prostate-specific membrane antigen in prostate cancer: current state of the art and future challenges*. Prostate cancer and prostatic diseases, 2016; Maurer, T., et al., *Current use of PSMA-PET in prostate cancer management*. Nature Reviews Urology, 2016). Prostate-specific membrane antigen is an extracellular hydrolase whose catalytic center comprises two zinc(II) ions with a bridging hydroxido ligand. It is highly upregulated in metastatic and hormone-refractory prostate carcinomas, but its physiologic expression has also been reported in kidneys, salivary glands, small intestine, brain and, to a low extent, also in healthy prostate tissue. In the intestine, PSMA facilitates absorption of folate by conversion of pteroylpoly-γ-glutamate to the pteroylglutamate (folate). In the brain, it hydrolyses N-acetyl-L-aspartyl-L-glutamate (NAAG) to N-acetyl-L-aspartate and glutamate.

PSMA-Targeting Active Agents

PSMA targeting molecules usually comprise a binding unit that encompasses a zinc-binding group (such as urea (Zhou, J., et al., *NAAG peptidase inhibitors and their potential for diagnosis and therapy*. Nature Reviews Drug Discovery, 2005. 4(12): p. 1015-1026), phosphinate or phosphoramidate) connected to a P1' glutamate moiety, which warrants high affinity and specificity to PSMA and is typically further connected to an effector functionality (Machulkin, A. E., et al., *Small-molecule PSMA ligands. Current state, SAR and perspectives*. Journal of drug targeting, 2016: p. 1-15). The effector part is more flexible and to some extent tolerant towards structural modifications. The entrance funnel to the binding site of PSMA accommodates two other prominent structural features, which are important for ligand binding. The first one is an arginine patch, a positively charged area at the wall of the entrance funnel and the structural explanation for the preference of negatively charged functionalities at the P1 position of PSMA. Upon binding the concerted repositioning of the arginine side chains can lead to the opening of an S1 hydrophobic accessory pocket, the second important structure, that has been shown to accommodate an iodo-benzyl group of several urea based inhibitors, thus contributing to their high affinity for PSMA (Barinka, C., et al., *Interactions between Human Glutamate Carboxypeptidase II and Urea-Based Inhibitors: Structural Characterization*. Journal of medicinal chemistry, 2008. 51(24): p. 7737-7743).

Zhang et al. discovered a remote binding site of PSMA, which can be employed for bidentate binding mode (Zhang, A. X., et al., *A remote arene-binding site on prostate specific membrane antigen revealed by antibody-recruiting small molecules*. Journal of the American Chemical Society, 2010. 132(36): p. 12711-12716). The so called arene-binding site is a simple structural motif shaped by the side chains of Arg463, Arg511 and Trp541, and is part of the PSMA entrance lid. The engagement of the arene-binding site by a distal inhibitor moiety can result in a substantial increase in the inhibitor affinity for PSMA due to avidity effects. PSMA I&T was developed with the intention to interact this way with PSMA, albeit no crystal structure analysis of binding mode is available. A necessary feature according to Zhang et al. is a linker unit (suberic acid in the case of PSMA I&T) which facilitates an open conformation of the entrance lid of PSMA and thereby enabling the accessibility of the arene-binding site. It was further shown that the structural composition of the linker has a significant impact on the tumor-targeting and biologic activity as well as on imaging contrast and pharmacokinetics (Liu, T., et al., *Spacer length effects on in vitro imaging and surface accessibility of fluorescent inhibitors of prostate specific membrane antigen*. Bioorganic & medicinal chemistry letters, 2011. 21(23): p. 7013-7016), properties which are crucial for both high imaging quality and efficient targeted endoradiotherapy.

Two categories of PSMA targeting inhibitors are currently used in clinical settings. On the one side are tracer with chelating units for radionuclide complexation as PSMA I&T or related compounds (Kiess, A. P., et al., *Prostate-specific membrane antigen as a target for cancer imaging and therapy*. The quarterly journal of nuclear medicine and molecular imaging: 2015. 59(3): p. 241). On the other side are small molecules, comprising a targeting unit and effector molecules. Depending on the used radionuclide/halogen, the radiolabeled PSMA inhibitors may be used for imaging or endoradiotherapy. Among small molecule inhibitors with chelators for imaging, the most often used agents for selective PSMA imaging are PSMA HBED-CC (Eder, M., et al., *$^{68}$Ga-complex lipophilicity and the targeting property of a urea-based PSMA inhibitor for PET imaging*. Bioconjugate chemistry, 2012. 23(4): p. 688-697), PSMA-617 (Benešová, M., et al., *Preclinical Evaluation of a Tailor-Made DOTA-Conjugated PSMA Inhibitor with Optimized Linker Moiety for Imaging and Endoradiotherapy of Prostate Cancer*. Journal of Nuclear Medicine, 2015. 56(6): p. 914-920) and PSMA I&T (Weineisen, M., et al., *Development and first in human evaluation of PSMA I&T-A ligand for diagnostic imaging and endoradiotherapy of prostate cancer*. Journal of Nuclear Medicine, 2014. 55 (supplement 1): p. 1083-1083). PSMA HBED-CC, or PSMA-11 was one of the first PSMA inhibitors and is currently used for imaging since therapeutic applications are not possible with the chelator HBED-CC. However, due to the unique physical characteristics and the advantages of $^{18}$F for PET imaging, like the longer half-life, the low positron energy, which results in higher image resolution and the possibility for largescale production in a cyclotron, several groups have focused on the development of $^{18}$F-labeled urea-based inhibitors for PCa imaging.

The $^{18}$F-labelled urea-based PSMA inhibitor $^{18}$F-DCFPyl demonstrated promising results in the detection of primary and metastatic PCa (Rowe et al., Molecular Imaging and Biology, 1-9 (2016)) and superiority to $^{68}$Ga-PSMA-HBED-CC in a comparative study (Dietlein et al., Molecular Imaging and Biology 17, 575-584 (2015)). Based on the structure of PSMA-617, the $^{18}$F-labelled analogue PSMA-1007 was recently developed, which showed comparable tumor-to-organ ratios (Cardinale et al., Journal of nuclear medicine: official publication, Society of Nuclear Medicine 58, 425-431 (2017); Giesel et al., European journal of nuclear medicine and molecular imaging 43, 1929-1930 (2016)). A comparative study with $^{68}$Ga-PSMA-HBED-CC revealed similar diagnostic accuracy of both tracers and a reduced urinary clearance of $^{18}$F-PSMA-1007, enabling a better assessment of the prostate (Giesel et al., European journal of nuclear medicine and molecular imaging 44, 678-688 (2017)).

An attractive approach for introducing $^{18}$F labels is the use of silicon fluoride acceptors (SiFA). Silicon fluoride acceptors are described, for example, in Lindner et al., Bioconjugate Chemistry 25, 738-749 (2014). It has been demonstrated in the literature that $^{18}$F-labeled SiFA compounds can be produced by $^{18}$F-for-$^{19}$F isotopic exchange reaction, but also by $^{18}$F-for-OH and even $^{18}$F-for-H substitution reactions, e.g. in Mu L et al., Angew Chem Int Ed Engl. 2008; 47(26):4922-5 and Höhne A et al., Bioconjug Chem. 2008 September; 19(9):1871-9, respectively. In order to preserve the silicon-fluoride bond, the use of silicon fluoride acceptors, however, introduces the necessity of sterically demanding groups, e.g. two tert-butyl groups at the Si—F and Si—$^{18}$F silicone group, e.g. as Si(tert-butyl)$_2$ X, where X is F or $^{18}$F. This in turn renders silicon fluoride acceptors highly hydrophobic. In terms of binding to the target molecule, in particular to the target protein which is PSMA, the hydrophobic moiety provided by the silicone fluoride acceptor may be exploited for the purpose of establishing interactions of the radio-diagnostic or -therapeutic compound with the hydrophobic pocket described in Zhang et al., Journal of the American Chemical Society 132, 12711-12716 (2010). Yet, prior to binding, the higher degree of lipophilicity introduced into the molecule poses a severe problem with respect to the development of radiopharmaceuticals with suitable in vivo biodistribution, i.e. low unspecific binding in non-target tissue.

Failure to Solve the SiFA-Associated Hydrophobicity Problem

Despite many attempts, the hydrophobicity problem caused by silicon fluoride acceptors has not been satisfactorily solved in the prior art.

To explain further, Schirrmacher E. et al. (Bioconjugate Chem. 2007, 18, 2085-2089) synthesized different $^{18}$F-labelled peptides using the highly effective labelling synthon p-(di-tert-butylfluorosilyl) benzaldehyde ([$^{18}$F]SiFA-A), which is one example of a silicon fluoride acceptor. The SiFA technique resulted in an unexpectedly efficient $^{18}$F-for-$^{19}$F isotopic exchange and yielded the $^{18}$F-synthon in almost quantitative yields in high specific activities between 225 and 680 GBq/μmol (6081-18 378 Ci/mmol) without applying HPLC purification. [$^{18}$F]SiFA-benzaldehyde was finally used to label the N-terminal amino-oxy (N-AO) derivatized peptides AO-Tyr3-octreotate (AO-TATE), cyclo (fK(AO-N)RGD) and N-AO-PEG$_2$-[D-Tyr-Gln-Trp-Ala-Val-Ala-His-Thi-Nle-NH$_2$] (AO-BZH3, a bombesin derivative) in high radiochemical yields. Nevertheless, the labelled peptides are highly lipophilic (as can be taken from the HPLC retention times using the conditions described in this paper) and thus unsuitable for further evaluation in animal models or humans.

In Wangler C. et al. (Bioconjugate Chem., 2009, 20 (2), pp 317-321), the first SiFA-based kit-like radiofluorination of a protein (rat serum albumin, RSA) has been described. As a labelling agent, 4-(di-tert-butyl[$^{18}$F]fluorosilyl)benzenethiol ([$^{18}$F]SiFA-SH) was produced by simple isotopic exchange in 40-60% radiochemical yield (RCY) and coupled directly to maleimide derivatized serum albumin in an overall RCY of 12% within 20-30 min. The technically simple labelling procedure does not require any elaborated purification procedures and is a straightforward example of a successful application of Si—$^{18}$F chemistry for in vivo imaging with PET. The time-activity curves and μPET images of mice showed that most of the activity was localized in the liver, thus demonstrating that the labelling agent is too lipophilic and directs the in vivo probe to hepatobiliary excretion and extensive hepatic metabolism.

Wangler C. et al. (Bioconjug Chem. 2010 Dec. 15; 21(12):2289-96) subsequently tried to overcome the major drawback of the SiFA technology, the high lipophilicity of the resulting radiopharmaceuticals, by synthesizing and evaluating new SiFA-octreotate analogues (SiFA-Tyr$^3$-octreotate, SiFA-Asn(AcNH-β-Glc)-Tyr$^3$-octreotate and SiFA-Asn(AcNH-β-Glc)-PEG-Tyr$^3$-octreotate). In these compounds, hydrophilic linkers and pharmacokinetic modifiers were introduced between the peptide and the SiFA-moiety, i.e. a carbohydrate and a PEG linker plus a carbohydrate. As a measure of lipophilicity of the conjugates, the log $P_{(ow)}$ was determined and found to be 0.96 for SiFA-Asn(AcNH-β-Glc)-PEG-Tyr$^3$-octreotate and 1.23 for SiFA-Asn(AcNH-β-Glc)-Tyr$^3$-octreotate. These results show that the high lipophilicity of the SiFA moiety can only be marginally compensated by applying hydrophilic moieties. A first imaging study demonstrated excessive hepatic clearance/liver uptake and thus has never been transferred into a first human study.

Kostikov et al. (J. Fluorine Chem., 2011, 132, 27-34) presented a charged SiFA bearing molecule which has tetraalkylammonium group as part of the SiFA moiety.

Bernard-Gauthier et al. (Biomed Res Int. 2014; 2014: 454503) reviews a great plethora of different SiFA species that have been reported in the literature ranging from small prosthetic groups and other compounds of low molecular weight to labelled peptides and most recently affibody molecules. In view of these data the problem of lipophilicity of SiFA-based prosthetic groups has not been solved so far; i.e. a methodology that reduces the overall lipophilicity of a SiFA conjugated peptide to a log D lower than approximately (approx.) −2.0 has not been described.

In Lindner S. et al. (Bioconjug Chem. 2014 Apr. 16; 25(4):738-49) it is described that PEGylated bombesin (PESIN) derivatives as specific GRP receptor ligands and RGD (one-letter codes for arginine-glycine-aspartic acid) peptides as specific αvβ3 binders were synthesized and tagged with a SiFA moiety. To compensate the high lipophilicity of the SiFA moiety various hydrophilic structure modifications were introduced leading to reduced log D values. SiFA-Asn(AcNH-β-Glc)-PESIN, SiFA-Ser(β-Lac)-PESIN, SiFA-Cya-PESIN, SiFA-LysMe$_3$-PESIN, SiFA-γ-carboxy-D-Glu-PESIN, SiFA-Cya$_2$-PESIN, SiFA-LysMe$_3$-γ-carboxy-D-Glu-PESIN, SiFA-(γ-carboxy-D-Glu)$_2$-PESIN, SiFA-RGD, SiFA-γ-carboxy-D-Glu-RGD, SiFA-(γ-carboxy-D-Glu)$_2$-RGD, SiFA-LysMe$_3$-γ-carboxy-D-Glu-RGD. All of these peptides—already improved and derivatized with the aim to reduce the lipophilicity—showed a log D value in the range between +2 and −1.22.

In Niedermoser S. et al. (J Nucl Med. 2015 July; 56(7): 1100-5), newly developed [$^{18}$F]SiFA- and [$^{18}$F]SiFAlin-modified TATE derivatives were compared with the current clinical gold standard $^{68}$Ga-DOTATATE for high-quality imaging of somatostatin receptor-bearing tumors. For this purpose, [$^{18}$F]SiFA-TATE and two quite complex analogues, [$^{18}$F]SiFA-Glc-PEG$_1$-TATE, [$^{18}$F]SiFAlin-Glc-Asp$_2$-PEG$_1$-TATE were developed. None of the agents showed a log D<−1.5.

US 2017/0246327 A1 relates to $^{18}$F-tagged inhibitors of PSMA.

S. Litau et al. (Bioconjug. Chem., 2015 Dec. 16; 26(12): 2350-59) disclose SiFA based TATE derivatives for PET imaging of SSTR-positive tumors.

L. O. Dialer et al., (J. Med. Chem., 2013 Oct. 10; 56(19): 7552-63 disclose the results of studies toward the development of silicon-containing building blocks for the $^{18}$F-labeling of peptides.

Considering the above-cited prior art, the technical problem of the present invention is to provide improved radiodiagnostics and radiotherapeutics.

Definitions

"Amino acid" refers to compounds carrying an amino group and a carboxylic acid group in the same molecule. Unless indicated otherwise in a specific context, it includes proteinogenic and non-proteinogenic amino acids. In either case, preference is given to α-amino acids. Also, preferred are D-amino acids.

The terms "natural amino acid" and "proteinogenic amino acid" are used equivalently herein. Preferably, said proteinogenic amino acids are: Ala, Asn, Asp, Arg, Cys, Gln, Glu, Gly, His, Ile, Leu, Lys, Met, Phe, Pro, Ser, Thr, Trp, Tyr and Val. Optionally, selenocysteine may be used. While the proteinogenic amino acids are in the L-form, it is understood that the present invention preferably makes use of the corresponding D-form.

As will be appreciated by the skilled person, the term pharmaceutically acceptable salt refers to salts which are suitable for use in a pharmaceutical composition for administration to a patient. They may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline-earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Further examples of pharmaceutically acceptable salts include, but are not limited to, acetate, adipate, alginate, ascorbate, aspartate, benzenesulfonate, benzoate, bicarbonate, bisulfate, bitartrate, borate, bromide, butyrate, calcium edetate, camphorate, camphorsulfonate, camsylate, carbonate, chloride, citrate, clavulanate, cyclopentanepropionate, digluconate, dihydrochloride, dodecylsulfate, edetate, edisylate, estolate, esylate, ethanesulfonate, formate, fumarate, gluceptate, glucoheptonate, gluconate, glutamate, glycerophosphate, glycolylarsanilate, hemisulfate, heptanoate, hexanoate, hexylresorcinate, hydrabamine, hydrobromide, hydrochloride, hydroiodide, 2-hydroxy-ethanesulfonate, hydroxynaphthoate, iodide, isothionate, lactate, lactobionate, laurate, lauryl sulfate, malate, maleate, malonate, mandelate, mesylate, methanesulfonate, methylsulfate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, 3-phenylpropionate, phosphate/diphosphate, picrate, pivalate, polygalacturonate, propionate, salicylate, stearate, sulfate, subacetate, succinate, tannate, tartrate, teoclate, tosylate, triethiodide, undecanoate, valerate, and the like (see, for example, S. M. Berge et al., "Pharmaceutical Salts", J. Pharm. Sci., 66, pp. 1-19 (1977)).

It is understood that throughout the present specification the term "compound" encompasses solvates, polymorphs, prodrugs, codrugs, cocrystals, tautomers, racemates, enantiomers, or diastereomers or mixtures thereof unless mentioned otherwise.

When the compounds of the present invention are provided in crystalline form, the structure can contain solvent molecules. The solvents are typically pharmaceutically acceptable solvents and include, among others, water (hydrates) or organic solvents. Examples of possible solvates include ethanolates and iso-propanolates.

The term "codrug" refers to two or more therapeutic compounds bonded via a covalent chemical bond. A detailed definition can be found, e.g., in N. Das et al., European Journal of Pharmaceutical Sciences, 41, 2010, 571-588.

The term "cocrystal" refers to a multiple component crystal in which all components are solid under ambient conditions when in their pure form. These components co-exist as a stoichiometric or non-stoichometric ratio of a target molecule or ion (i.e., compound of the present invention) and one or more neutral molecular cocrystal formers. A detailed discussion can be found, for example, in Ning Shan et al., Drug Discovery Today, 13(9/10), 2008, 440-446 and in D. J. Good et al., Cryst. Growth Des., 9(5), 2009, 2252-2264.

While, being less preferred, the compounds of the present invention can also be provided in the form of a prodrug, namely a compound which is metabolized in vivo to the active metabolite. Suitable prodrugs are, for instance, esters. Specific examples of suitable groups are given, among others, in US 2007/0072831 in paragraphs [0082] to [0118] under the headings prodrugs and protecting groups.

To the extent compounds of the invention exhibit a pH-dependent charged state, it is understood that all possible charged states are embraced. A preferred pH range in this regard is from 0 to 14.

To the extent a compound according to the invention bears a net charge, it is understood that the compound is provided in electroneutral form. This is achieved by one or more counterions, preferred counterions being defined in relation to the term "salt" herein above.

The preferred definitions given in the "Definition"-section apply to all of the embodiments described below unless stated otherwise.

SUMMARY OF THE INVENTION

Figure 1:
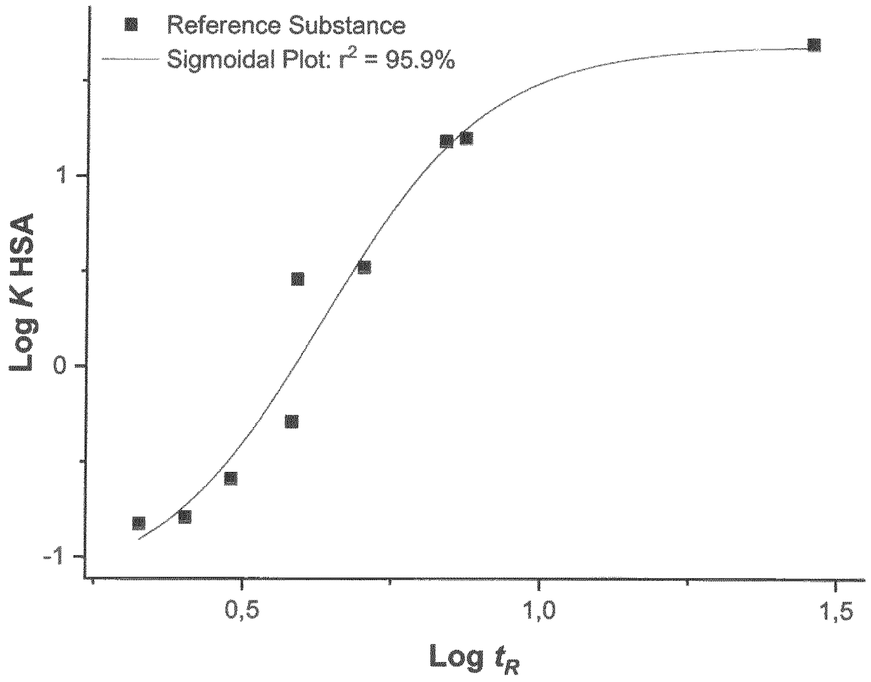
FIG. 1. Exemplary sigmoidal plot of the reference substance logarithmic K of HSA binding literature value versus respective logarithm of the retention time on the Chiralpak HSA column FIG. 2. Biodistribution profile of [$^{18}$F]01 a at 1 h p.i. in LNCaP tumor-bearing CB17-SCID mice. Data is expressed as mean % ID/g±SD (n=4).

The present invention provides a ligand-SiFA conjugate compound represented by formula (1)

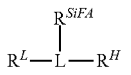

(1)

wherein:

$R^L$ is a ligand moiety which is capable of binding to prostate-specific membrane antigen (PSMA);

$R^{SiFA}$ is a silicon-fluoride acceptor (SiFA) moiety selected from:

(i) a SiFA moiety which comprises a silicon atom and a fluorine atom, wherein the fluorine atom is linked via a covalent bond directly to the silicon atom, and which SiFA moiety can be labeled with $^{18}$F by isotopic exchange of $^{19}$F by $^{18}$F or which is labeled with $^{18}$F; and (ii) a SiFA moiety which comprises a silicon atom and a hydroxy group, wherein the hydroxy group is linked via a covalent bond directly to the silicon atom, and which SiFA moiety can be labeled with $^{18}$F by nucleophilic substitution of OH by $^{18}$F;

(iii) a SiFA moiety which comprises a silicon atom and a hydrogen atom, wherein the hydrogen atom is linked via a covalent bond directly to the silicon atom, and which SiFA moiety can be labeled with $^{18}$F by nucleophilic substitution of H by $^{18}$F;

L is a linking moiety;

$R^H$ is a hydrophilic moiety which comprises (i) a linear or branched sequence of 2 to 10 hydrophilic amino acid units $A^H$, each of which is independently derived from a natural or non-natural amino acid carrying a hydrophilic side chain, and optionally one amino acid unit $A^H$ derived from a natural or non-natural amino acid which is devoid of a hydrophilic side chain, wherein the hydrophilic amino acid units and, if present, the unit $A^H$, are bound to each other via a direct covalent bond or via a coupling unit;

and which optionally further comprises (ii) one or more hydrophilic residues $R^T$, each of which may be bound to an amino group, a carboxylic acid group, or to a hydrophilic side chain of an amino acid unit;

or a pharmaceutically acceptable salt thereof.

A further aspect of the invention relates to a pharmaceutical or diagnostic composition comprising or consisting of one or more conjugate compounds or salts as defined herein. In accordance with still a further aspect, the invention provides a conjugate compound or salt as defined herein for use in a method of diagnosing, treating, or diagnosing and treating (a) cancer including prostate cancer; or (b) neoangiogenesis/angiogenesis.

DETAILED DESCRIPTION OF THE INVENTION

The ligand-SiFA conjugate compound provided by the present invention (which may be referred to herein as the compound or the conjugate compound in accordance with the invention, or as the compound or conjugate compound "defined herein") combines, in a single compound, a ligand moiety which allows the compound to bind to prostate-specific membrane antigen (PSMA), and a silicon-fluoride acceptor (SiFA) moiety which allows the compound to be labeled with the fluorine isotope $^{18}F$ and to be detected, e.g. after it has bound to PSMA in the body of a patient. With a view to this combination (or conjugation) of moieties fulfilling different functions, the compounds in accordance with the invention can be considered as conjugates or conjugate compounds.

In addition to the ligand moiety and the SiFA moiety, the compounds in accordance with the invention comprise a hydrophilic moiety $R^H$ which fulfills the function of a hydrophilic pharmacokinetic modifier, i.e. a moiety which has a beneficial effect on the pharmacokinetic characteristics of the compounds in accordance with the invention. This will be explained in more detail below.

Hydrophilic Moiety $R^H$

The hydrophilic moiety $R^H$ comprises a linear or branched sequence (also referred to herein as a sequence of amino acid units) comprising 2 to 10 hydrophilic amino acid units $A^H$, each of which is independently derived from an amino acid carrying a hydrophilic side chain and optionally one amino acid unit $A^N$ derived from an amino acid which is devoid of a hydrophilic side chain. In addition to the amino acid units, the linear or branched sequence may comprise one or more coupling units.

The amino acid carrying a hydrophilic side chain (which may also be referred to as hydrophilic amino acid) may be a natural amino acid, but may also be a non-natural (e.g. synthetic) amino acid. As will be understood, an amino acid carrying a hydrophilic side chain contains an amino group $—NH_2$, a carboxylic acid group —COOH (or a salt thereof), and in addition to the amino group and the carboxylic acid group, a hydrophilic side chain which comprises one or more hydrophilic functional groups, including the possibility that the hydrophilic side chain consists of the hydrophilic functional group. Preferably, the hydrophilic side chain comprises or consists of at least one hydrophilic functional group selected from an amino group $—NH_2$ or N-methylated derivatives thereof, a carboxylic acid group —COOH, a hydroxy group —OH, a guanidino group $—NH—C(NH)—NH_2$ or N-methylated derivatives thereof, an amido group $—C(O)—NH_2$ or —NH—C(O)—OH or N-methylated derivatives thereof, and a urea group $—NH—C(O)—NH_2$ or N-methylated derivatives thereof, and from isosters of these groups. More preferably, the hydrophilic side chain comprises or consists of at least one hydrophilic functional group selected from an amino group $—NH_2$, a carboxylic acid group —COOH, a hydroxy group, a guanidino group $—NH—C(NH)—NH_2$ and a urea group $—NH—C(O)—NH_2$, and from isosters of these groups. Still more preferably, at least one of the hydrophilic amino acid units is derived from an amino acid with a hydrophilic side chain which comprises or consists of a carboxylic acid group as a hydrophilic functional group.

In the amino acid carrying a hydrophilic side chain, the hydrophilic side chain is generally a group which is attached to a chain of atoms which extends between an amino group and a carboxylic acid group of the hydrophilic amino acid, and is therefore referred to as a side chain. It should be understood that this does not impose any restrictions of the relative length of the side chain compared to the chain of atoms which extends between the amino group and the carboxylic acid group (the latter being also referred to as a main chain). For example, a preferred amino acid carrying a hydrophilic side chain for use in the context of the present invention may suitably have a structure $HOOC—(CH_2)_{h1}—NH_2$, wherein h1 is an integer selected from 1, 2, 3, 4, 5 and 6, and a hydrophilic side chain replaces one of the hydrogen atoms in one of the methylene groups $—CH_2—$. A more preferred example of such an amino acid carrying a hydrophilic side chain for use in the context of the present invention has the structure $HOOC—CH_2—NH_2$, wherein a hydrophilic side chain replaces one of the hydrogen atoms in the methylene group $—CH_2—$.

The hydrophilic side chain is preferably selected from a group $—(CH_2)_c—COOH$, a group $—(CH_2)_c—NH_2$ or N-methylated derivatives thereof, a group $—(CH_2)_c—CH(NH_2)—COOH$, a group $—(CH_2)_c—NH—C(O)—NH_2$ or N-methylated derivatives thereof and a group $—(CH_2)_c—NH—C(NH)—NH_2$ or N-methylated derivatives thereof, wherein c is an integer of 0 to 6, preferably of 1 to 6. More preferably, the hydrophilic side chain is selected from a group $—(CH_2)_c—COOH$, a group $—(CH_2)_c—NH_2$, a group $—(CH_2)_c—CH(NH_2)—COOH$, a group $—(CH_2)_c—NH—C(O)—NH_2$ and a group $—(CH_2)_c—NH—C(NH)—NH_2$, wherein c is an integer of 0 to 6, preferably of 1 to 6. Still more preferably, at least one of the hydrophilic amino acid units is derived from an amino acid carrying a group $—(CH_2)_c—COOH$, wherein c is an integer of 0 to 6, preferably of 1 to 6, as the hydrophilic side chain;

Preferred is that the hydrophilic amino acid units in $R^H$ are each independently derived from an amino acid selected from 2,3-diaminopropionic acid (Dap), 2,4-diaminobutanoic acid (Dab), ornithine (Orn), lysine (Lys), 4-aminopiperidine-4-carboxylic acid (Apc4), 3-aminopiperidine-3-carboxylic acid (Apc3), 2-aminopiperidine-2-carboxylic acid (Apc2), aspartic acid (Asp), homoglutamic acid (Hgl), glutamic acid (Glu), 2,3-diaminosuccinic acid, diaminopentanedioic acid, diaminohexanedioic acid, diaminoheptanedioic acid, diaminooctanedioic acid, threonine (Thr) and citrulline (Cit). It is further preferred that the amino acids are in D-configuration. More preferably, the hydrophilic amino acid units in $R^H$ are each independently derived from an amino acid selected from 2,3-diaminopropionic acid (Dap), ornithine (Orn), lysine (Lys), aspartic acid (Asp), glutamic acid (Glu), and citrulline (Cit). Also in this context, the amino acids are preferably in D-configuration.

Each of the hydrophilic amino acid units comprised by $R^H$ is derived from an amino acid carrying a hydrophilic side chain by the formation of one or more bonds using the functional groups provided by the amino acid to incorporate the amino acid into a linear or branched sequence of amino acid units.

Thus, from a formal point of view, a hydrophilic amino acid unit is obtained from an amino acid by converting a functional group such that a free valence is obtained. As will be understood, this free valence is used to provide a bond with another group in the compounds in accordance with the invention. For example, a main chain or side chain —COOH is converted into —C(O)—, and a main chain or side chain $—NH_2$ is converted into —NH—. If the hydrophilic amino acid unit is a branching point in the linear or branched sequence of $R^H$, three functional groups are converted accordingly. If the hydrophilic amino acid unit is located in a linear segment of the linear or branched sequence of $R^H$, two functional groups provide free valences. If the hydrophilic amino acid unit is a terminal unit in the linear or branched sequence of $R^H$, one functional group provides a free valence.

As will be understood, the functional groups provided by the amino acid carrying a hydrophilic side chain which allow a bond to be formed with an adjacent unit (or further with the linking moiety L comprised by the compounds in accordance with the invention or with an optional hydrophilic residue $R^T$) are the amino group, the carboxylic acid group, and a hydrophilic functional group comprised by the hydrophilic side chain. In this regard, reliance can be put on coupling reactions established in synthetic chemistry in general, and in protein synthesis in particular, such as the formation of an amide bond (—NH—C(O)—) or the formation of a urea bond (—NH—C(O)—NH—). Thus, the hydrophilic amino acid units in the linear or branched sequence form at least one bond with an adjacent unit (which may be a direct bond with another adjacent amino acid unit, or a bond with an adjacent coupling unit), and may form one or two further bonds which, independently, may also be a bond with an adjacent unit or with the linking moiety L comprised by the compounds in accordance with the invention or with an optional hydrophilic residue $R^T$. If a bond is formed using a functional group comprised by the hydrophilic side chain of the amino acid, it may be preferable if the respective hydrophilic amino acid unit is derived from an amino acid which carries a hydrophilic side chain comprising a terminal amino group or a terminal carboxylic acid group.

Optionally, the linear or branched sequence of amino acids comprises one amino acid unit $A^N$ which is derived from an amino acid which is devoid of a hydrophilic side chain. As will be understood, the amino acid unit $A^N$ optionally comprised by $R^H$ is derived from an amino acid devoid of a hydrophilic side chain by the formation of one or more bonds using the functional groups provided by the amino acid to incorporate the amino acid into a linear or branched sequence of amino acid units. The amino acid which is devoid of a hydrophilic side chain (which may also be referred to as non-hydrophilic amino acid) may be a natural amino acid, but may also be a non-natural (e.g. synthetic) amino acid. The amino acid devoid of a hydrophilic side chain may be devoid of any side chain attached to the chain of atoms which extends between an amino group and a carboxylic acid group of the amino acid, or may contain such a a side chain, provided that it is not a hydrophilic side chain. Examples of an amino acid unit derived from an amino acid devoid of a hydrophilic side chain include a unit derived from an amino acid carrying no side chain attached to the chain of atoms which extends between an amino group and a carboxylic acid group of the amino acid, or an amino acid carrying a hydrocarbyl group as a side chain, e.g. an alkyl group or an aralkyl group, such as an amino acid unit derived from glycine (Gly), a unit derived from phenylalanine (Phe), a unit derived from β-alanine (β-Ala) or a unit derived from aminohexanoic acid (Ahx).

While the hydrophilic amino acid units $A^H$ are a means to solve the hydrophobicity problem caused by the SiFA moiety as explained in the introduction, the non-hydrophilic unit $A^N$ is a means of adjusting or fine-tuning the degree of hydrophilicity introduced into the compound of the invention by said units $A^H$. Such adjusting or fine-tuning preferably serves to establish (i) a preferred log $D_{7.4}$ value and/or (ii) preferred pharmacokinetics.

To explain further, compounds of the invention preferably have log $D_{7.4}$ values between about −1.5 and −4.0, preferably between −2.0 and −3.5, more preferably between −2.5 and −3.5. A compound with a log $D_{7.4}$ in these ranges inherently has the pharmacokinetics explained in the following.

In view of the preferred use of imaging during a surgical intervention (see further below), a premature occurrence of the compounds in the bladder or in the urethra is not desirable, given that this would interfere the detection of neoplastic tissue, in particular in the prostate, but also lymph node metastases in the pelvic region. Premature occurrence is the occurrence of significant amounts of compound at about 0 to about 240 min, preferably at about 40 to about 120 min, and more preferably at about 60 to about 90 min after administration of the radiopharmaceuticals in patients. Such occurrence is premature in the sense that it would take place within the time window normally needed to acquire a positron emission tomography (PET) scan of a patient. Preferred is accordingly that no significant amounts of the labeled compound occur in the urinary tract within these preferred time spans. Significant amounts are amounts which interfere with a confident detection of neoplastic tissue in the prostate and metastases in the pelvic region.

To the extent a longer duration of the PET imaging procedure is envisaged, a further or different fine-tuning of the overall hydrophilicity of the compound of the invention may be performed without further ado and based on the above disclosure.

Accordingly, the present invention also provides, in a further aspect, a plurality of compounds which compounds share the same moieties $R^L$, $R^{SiFA}$ and L, but differ with regard to their $R^H$. A "plurality" preferably means 2, 3, 4, 5, 6, 7, 8, 9 or 10 compounds. Each compound strikes a balance between undisturbed detection of neoplastic tissue during the imaging and subsequent clearance via the urinary tract, wherein different degrees of hydrophilicity allow for distinct time windows of imaging procedure.

As defined above, the hydrophilic moiety $R^H$ comprises a linear or branched sequence of 2 to 10 hydrophilic amino acid units and optionally one amino acid unit $A^N$.

It is generally preferred for $R^H$ in the context of the invention that the sequence is a linear sequence.

It is generally preferred for $R^H$ in the context of the invention that $R^H$ and the sequence of amino acid units comprises a total number of 3 to 10, more preferably 3 to 5, and still more preferably 3 hydrophilic amino acid units.

In another preferred embodiment, $R^H$ comprises one amino acid unit $A^N$ derived from an amino acid devoid of a hydrophilic side chain and 2 hydrophilic amino acid units.

In the sequence comprised by $R^H$, the hydrophilic amino acid units and, if present, the unit $A^N$, are bound to each other via a direct covalent bond or via a coupling unit. Moreover, a coupling unit may also be present between the linking moiety L and a first amino acid unit of the sequence comprised by $R^H$.

As noted above, the hydrophilic amino acid units may be bound to an adjacent unit (i.e. an adjacent amino acid unit or an adjacent coupling unit) (i) by a bond formed using an amino group of the amino acid from which the hydrophilic amino acid unit is derived, (ii) by a bond formed via a carboxylic acid group of the amino acid from which the hydrophilic amino acid unit is derived, and/or (iii) by a bond formed via a hydrophilic functional group contained in the hydrophilic side chain of the amino acid from which the hydrophilic amino acid unit is derived. In other words, the linkage between any of the hydrophilic amino acid units and an adjacent amino acid unit or coupling unit may be formed via functional group of the hydrophilic side chain. Suitable examples of the hydrophilic functional group in option (iii) for providing such a bond include an amino group or a carboxylic acid group. As also noted above, preferred examples for the bonds (i), (ii) and (iii) are an amide bond and a urea bond. Accordingly, what is commonly designated "isopeptide bond" is envisaged as being included as a bond connecting adjacent amino acid units.

As will be understood, in cases where two amino acid units are bound to each other via a direct covalent bond, one functional group of a first amino acid is reacted with a compatible functional group of a second amino acid. Preferably, these functional groups are an amino group and a carboxylic acid group, so that the direct bond between two amino acid units is provided by an amide bond.

Suitable coupling units which may be used to couple amino acid units are known to the skilled person in the field of organic synthetic chemistry. In the context of the present invention, a particularly suitable coupling unit is the a coupling unit —C(O)—, which coupling unit forms a urea bond (—NH—C(O)—NH—) with amino groups of two adjacent amino acid units comprised by $R^H$, or with an amino group of the linking moiety L and an amino group of an amino acid unit comprised by $R^H$. In fact, it is preferred that the group $R^H$ comprises at least one coupling unit —C(O)— forming a urea bond —NH—C(O)—NH— with amino groups of two adjacent amino acid units comprised by $R^H$ or with an amino group of the linking moiety L and an amino group of an amino acid unit comprised by $R^H$.

Moreover, the hydrophilic moiety of the conjugate compound in accordance with the invention optionally comprises one or more hydrophilic residues $R^T$ each of which may be bound to an amino group, a carboxylic acid group, or to a functional group (i.e. a hydrophilic functional group) in a hydrophilic side chain of an amino acid unit. Thus, as will be understood by the skilled person, in a moiety $R^H$ comprising a hydrophilic residue $R^T$, the amino group, carboxylic acid group, or a functional group in a hydrophilic side chain of an amino acid unit will have been reacted to form a bond with $R^T$, e.g. an amide bond or an ester bond. As will be further understood, the hydrophilic residue would be bound to an amino group, a carboxylic acid group, or to a functional group in a hydrophilic side chain of an amino acid unit which remains as a free group in the sequence of amino acid units, i.e. which is not involved in a bond between adjacent amino acid units, in a bond of an amino acid unit with the linking moiety L, or a bond between an amino acid unit and a coupling unit.

Preferred examples of such hydrophilic residues, which may be present singly or in combination, are a chelator group, a chelate group with a complexed metal or radiometal, a carbohydrate residue, a polyethylene glycol residue, a reduced amino acid (i.e. a residue of an amino acid wherein the carboxylic acid has been reduced to an alcohol) and an amino acid analogue with a carboxylic acid isoster (i.e. a group which is not a carboxylic acid, but has a structure which is isosteric with a carboxylic acid group).

However, it is noted that the conjugate compounds in accordance with the invention are highly suitable as radiopharmaceuticals or precursors thereof, in particular for diagnostic purposes, also in the absence of a chelator group and a chelate group, such that these groups do not need to be present.

Preferably, the hydrophilic moiety comprises not more than one hydrophilic residue $R^T$, and it is more preferred that the optional hydrophilic residue $R^T$ is absent.

Preferred structures of the hydrophilic moiety $R^H$ are discussed in the following. It will be understood that, unless indicated otherwise, the explanation given above applies likewise for these preferred structures.

A preferred structure of the moiety $R^H$ is represented by formula (2):

$$—R^{1H}(—R^T)_{a1} \quad (2)$$

wherein $R^{1H}$ represents a linear or branched, preferably linear, sequence of 2 to 10 hydrophilic amino acid units, each of which is independently derived from a natural or non-natural amino acid carrying a hydrophilic side chain, and optionally one amino acid unit $A^N$ derived from a natural or non-natural amino acid which is devoid of a hydrophilic side chain, wherein the hydrophilic amino acid units and, if present, the unit $A^N$, are bound to each other via a direct covalent bond or via a coupling unit;

$R^T$ represents a hydrophilic residue which may be bound to an amino group, a carboxylic acid group, or to a functional group of the hydrophilic side chain of an amino acid unit in the sequence $R^{1H}$; and a1 is 0 or 1, preferably 0.

As noted above, the definitions (and preferred definitions) for the hydrophilic amino acid units e.g. in terms of structure, number and linkage, for the amino acid carrying a hydrophilic side chain, for the amino acid unit $A^H$, and for $R^T$ provided above continue to apply for this preferred structure of $R^H$.

If a1 in formula (2) is 1, it is preferred that $R^T$ is bound to a terminal amino acid unit in the sequence $R^{1H}$, and it is more preferred that $R^T$ is a linear sequence and $R^T$ is bound to the terminal amino acid unit.

It is more preferred that the moiety —$R^H$ has the structure represented by formula (3A) or (3B), or by formula (3C) or (3D):

$$—\left[X^{1H}—A^{1H}\right]_{b1}X^{2H}—A^{2H} \quad (3A)$$

$$—\left[X^{1H}—A^{1H}\right]_{b1}X^{3H}—A^{3H}—R^T \quad (3B)$$

wherein b1 is an integer of 1 to 9; preferably 2 to 9, and more preferably 2 to 4;

$A^{1H}$, independently for each occurrence, is a hydrophilic amino acid unit derived from a (natural or non-natural) amino acid carrying a hydrophilic side chain;

$A^{2H}$ and $A^{3H}$ are each independently a hydrophilic amino acid unit derived from a (natural or non-natural) amino acid carrying a hydrophilic side chain;

$X^{1H}$, independently for each occurrence, is a bond or a coupling unit, $X^{2H}$ and $X^{3H}$ are each independently a bond or a coupling unit, and $R^T$ represents a hydrophilic residue which may be bound to an amino group, a carboxylic acid group, or to a functional group of a hydrophilic side chain of the amino acid unit $A^{3H}$;

$$—A^{1N}\left[X^{1H}—A^{1H}\right]_{c1}X^{2H}—A^{2H} \quad (3C)$$

$$—A^{1N}\left[X^{1H}—A^{1H}\right]_{c1}X^{3H}—A^{3H}—R^T \quad (3D)$$

wherein c1 is an integer of 1 to 9; and preferably 1 to 4;

$A^{1N}$ is an amino acid unit derived from an amino acid which is devoid of a hydrophilic side chain;

$A^{1H}$, independently for each occurrence, is a hydrophilic amino acid unit derived from a (natural or non-natural) amino acid carrying a hydrophilic side chain;

$A^{2H}$ and $A^{3H}$ are each independently a hydrophilic amino acid unit derived from a (natural or non-natural) amino acid carrying a hydrophilic side chain;

$X^{1H}$, independently for each occurrence, is a bond or a coupling unit, $X^{2H}$ and $X^{3H}$ are each independently a bond or a coupling unit, and $R^T$ represents a hydrophilic residue which may be bound to an amino group, a carboxylic acid group, or to a functional group of a hydrophilic side chain of the amino acid unit $A^{3H}$.

Also in this context, the definitions (and preferred definitions) for the hydrophilic amino acid units e.g. in terms of structure, number and linkage, for the amino acid carrying a hydrophilic side chain, for the amino acid unit derived from the amino acid devoid of a hydrophilic side chain, for the coupling unit, and for $R^T$ provided above continue to apply.

It is still more preferred that the moiety $R^H$ has the structure represented by formula (3E) or formula (3F):

$$-A^{4H}-X^{4H}-A^{5H}-X^{5H}-A^{6H}- \quad (3E),$$

$$-A^{1N}-X^{4H}-A^{5H}-X^{5H}-A^{6H} \quad (3F)$$

wherein $A^{4H}$, $A^{5H}$ and $A^{6H}$ are each independently a hydrophilic amino acid unit derived from a (natural or non-natural) amino acid carrying a hydrophilic side chain;

$X^{4H}$ and $X^{5H}$ are each independently a direct bond or a coupling unit and optionally a hydrophilic residue $R^T$ may be bound to an amino group, a carboxylic acid group, or to a functional group of a hydrophilic side chain of the amino acid unit $A^{6H}$; and $A^{1N}$ is an amino acid unit derived from an amino acid devoid of a hydrophilic side chain.

Also in this context, the definitions (and preferred definitions) for the hydrophilic amino acid units e.g. in terms of structure and linkage, for the amino acid carrying a hydrophilic side chain, for the amino acid unit derived from the amino acid devoid of a hydrophilic side chain, for the hydrophilic residue and for the coupling unit provided above continue to apply.

Thus, as an example, in a group —$R^H$ encompassed by preferred formula (3E), each of $A^{4H}$ $A^{H}$, and $A^{6H}$ may be independently derived from an amino acid selected from 2,3-diaminopropionic acid (Dap), ornithine (Orn), lysine (Lys), threonine (Thr), aspartic acid (Asp), glutamic acid (Glu), and citrulline (Cit), and each of $X^{4H}$ and $X^{5H}$ is independently a bond or a coupling unit —C(O)—, which coupling unit forms a urea bond with amino groups of two adjacent amino acid units. In one more preferred example of a group —$R^H$ encompassed by preferred formula (3E), the amino acid unit $A^{4H}$ is derived from an amino acid selected from 2,3-diaminopropionic acid (Dap), ornithine (Orn), lysine (Lys), threonine (Thr), aspartic acid (Asp), glutamic acid (Glu), and citrulline (Cit), $A^{5H}$ and $A^{6H}$ are amino acid units derived from glutamic acid, $X^{4H}$ is a bond and $X^{5H}$ is selected from a bond and a coupling unit —C(O)—, which coupling unit forms a urea bond with amino groups of two adjacent amino acid units. In another more preferred example of a group —$R^H$ encompassed by preferred formula (3E), the amino acid unit $A^{4H}$ is derived from an amino acid selected from 2,3-diaminopropionic acid (Dap), ornithine (Orn), lysine (Lys), threonine (Thr), aspartic acid (Asp), glutamic acid (Glu), and citrulline (Cit), $A^{5H}$ and $A^{6H}$ are amino acid units derived from citrulline, and $X^{4H}$ and $X^{5H}$ are each a bond.

In an exemplary group —$R^H$ encompassed by the preferred formula (3F), $A^{1N}$ is an amino acid unit derived from glycine (Gly), phenylalanine (Phe), β-alanine (β-Ala) and aminohexanoic acid (Ahx), $A^{5H}$ and $A^{6H}$ are independently derived from an amino acid selected from 2,3-diaminopropionic acid (Dap), ornithine (Orn), lysine (Lys), threonine (Thr), aspartic acid (Asp), glutamic acid (Glu), and citrulline (Cit), and each of $X^{4H}$ and $X^{5H}$ is independently a bond or a coupling unit —C(O)—, which coupling unit forms a urea bond with amino groups of two adjacent amino acid units. In one more preferred example of a group —$R^H$ encompassed by preferred formula (3F), the amino acid unit $A^{1N}$ is derived from glycine (Gly), phenylalanine (Phe), β-alanine (β-Ala) and aminohexanoic acid (Ahx), $A^{5H}$ and $A^{6H}$ are amino acid units derived from glutamic acid, $X^{4H}$ is a bond and $X^{5H}$ is selected from a bond and a coupling unit —C(O)—, which coupling unit forms a urea bond with amino groups of two adjacent amino acid units.

In an alternative preferred embodiment, the moiety $R^H$ has the structure represented by formula (3G):

(3G)

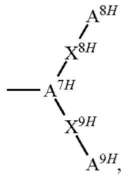

wherein $A^{7H}$, $A^{8H}$ and $A^{9H}$ are each independently a hydrophilic amino acid unit derived from a (natural or non-natural) amino acid carrying a hydrophilic side chain; and $X^{8H}$ and $X^{9H}$ are each independently a direct bond or a coupling unit;

and optionally a hydrophilic residue RT may be bound to an amino group, a carboxylic acid group, or to a functional group of a hydrophilic side chain of one or both of the amino acid units $A^{8H}$ and $A^{9H}$.

Also in this context, the definitions (and preferred definitions) for the hydrophilic amino acid units, e.g. in terms of structure and linkage, for the amino acid carrying a hydrophilic side chain, for the hydrophilic residue and for the coupling unit provided above continue to apply.

Among the above preferred groups (3A) to (3G), particular preference is given to (3E) and (3F).

Preferred structures of hydrophilic amino acid units which are present in $R^H$, and which can form part of the structures of formulae (1), (2) and in particular in (3A) to (3G) are discussed in the following.

For example, the hydrophilic amino acid units $A^{1H}$ in formula (3A), (3B), (3C) and (3D), independently for each occurrence, and the hydrophilic amino acid unit $A^{3H}$ in formula (3B) and (3D) are preferably represented by formula (4A) or (4B):

$$—NH—(CH_2)_a—(CHR^{2H})—(CH_2)_b—C(O)— \quad (4A)$$

$$—C(O)—(CH_2)_a—(CHR^{2H})—(CH_2)_b—NH— \quad (4B).$$

The hydrophilic amino acid unit $A^{2H}$ in formula (3A) and (3C) preferably has the structure represented by formula (4C) or (4D):

$—NH—(CH_2)_a—(CHR^{2H})—(CH_2)_b—C(O)OH$ (4C)

$—C(O)—(CH_2)_a—(CHR^{2H})—(CH_2)_b—NH_2$ (4D).

In formulae (4A) to (4D), independently for each amino acid unit, a is an integer of 0 to 6, b is an integer of 0 to 6, with the proviso that the sum a+b is not higher than 6; and $R^{2H}$ is a hydrophilic substituent.

In formula (3E) and (3F), the hydrophilic amino acid units $A^{4H}$ and $A^{5H}$ preferably have the structure represented by formula (4A) or (48):

$—NH—(CH_2)_a—(CHR^{2H})—(CH_2)_b—C(O)—$ (4A)

$—C(O)—(CH_2)_a—(CHR^{2H})—(CH_2)_b—NH—$ (4)

and the hydrophilic amino acid unit $A^{6H}$ preferably has the structure represented by formula (4C) or (4D):

$—NH—(CH_2)_a—(CHR^{2H})—(CH_2)_b—C(O)OH$ (40)

$—C(O)—(CH_2)_a—(CHR^{2H})—(CH_2)_b—NH_2$ (4D)

wherein, independently for each amino acid unit, a is an integer of 0 to 6, b is an integer of 0 to 6, with the proviso that the sum a+b is not higher than 6; and $R^{2H}$ is a hydrophilic substituent.

In formulae (3C), (3D) and (3F), the unit $A^{IN}$ derived from an amino acid devoid of a hydrophilic side chain preferably has the structure represented by formula (4E) or (4F):

$—NH—(CH_2)_a—(CHR^{2N})—(CH_2)_b—C(O)—$ (4E)

$—C(O)—(CH_2)_a—(CHR^{2N})—(CH_2)_b—NH—$ (4F).

In formulae (4E) and (4F), independently for each amino acid unit, a is an integer of 0 to 6, b is an integer of 0 to 6, with the proviso that the sum a+b is not higher than 6; and $R^{2N}$ is H or a non-hydrophilic substituent.

Finally, as further preferred structures of the hydrophilic moiety $R^H$, reference can be made to the structures represented by formula (5A), (5B), (5C) or (5D):

$—C(O)—(CH_2)_d—CHR^{3H}—(CH_2)_e—NH—C(O)—(CH_2)_f—CHR^{4H}—(CH_2)_g—NH—C(O)—NH—(CH_2)_h—CHR^{5H}—(CH_2)_i—COOH$ (5A), wherein $R^{3H}$ to $R^{5H}$ are independently a hydrophilic substituent;

d is an integer of 0 to 3, e is an integer of 0 to 3, with the proviso that the sum d+e is not higher than 3;

f is an integer of 0 to 3, g is an integer of 0 to 3, with the proviso that the sum f+g is not higher than 3;

h is an integer of 0 to 3, i is an integer of 0 to 3, with the proviso that the sum h+i is not higher than 3;

$—C(O)—(CH_2)_j—CHR^{6H}—(CH_2)_k—NH—C(O)—(CH_2)_m—CHR^{7H}—(CH_2)_n—NH—C(O)—(CH_2)_p—CHR^{8H}—(CH_2)_q—NH_2$ (5B), wherein $R^{6H}$ to $R^{8H}$ are independently a hydrophilic substituent;

j is an integer of 0 to 3, k is an integer of 0 to 3, with the proviso that the sum j+k is not higher than 3;

m is an integer of 0 to 3, n is an integer of 0 to 3, with the proviso that the sum m+n is not higher than 3;

p is an integer of 0 to 3, q is an integer of 0 to 3, with the proviso that the sum p+q is not higher than 3.

$—C(O)—(CH_2)_d—CHR^{3N}—(CH_2)_e—NH—C(O)—(CH_2)_f—CHR^{4H}—(CH_2)_g—NH—C(O)—NH—(CH_2)_h—CHR^{5H}—(CH_2)_i—COOH$ (5C), wherein $R^{3N}$ is H or a non-hydrophilic substituent;

$R^{4H}$ and $R^{5H}$ are independently a hydrophilic substituent;

d is an integer of 0 to 3, e is an integer of 0 to 3, with the proviso that the sum d+e is not higher than 3;

f is an integer of 0 to 3, g is an integer of 0 to 3, with the proviso that the sum f+g is not higher than 3;

h is an integer of 0 to 3, i is an integer of 0 to 3, with the proviso that the sum h+i is not higher than 3;

$—C(O)—(CH_2)_j—CHR^{6N}—(CH_2)_k—NH—C(O)—(CH_2)_m—CHR^{7H}—(CH_2)_n—NH—C(O)—(CH_2)_p—CHR^{8H}—(CH_2)_q—NH_2$ (5D), wherein $R^{6N}$ is H or a non-hydrophilic substituent;

$R^{7H}$ and $R^{8H}$ are independently a hydrophilic substituent;

j is an integer of 0 to 3, k is an integer of 0 to 3, with the proviso that the sum j+k is not higher than 3;

m is an integer of 0 to 3, n is an integer of 0 to 3, with the proviso that the sum m+n is not higher than 3;

p is an integer of 0 to 3, q is an integer of 0 to 3, with the proviso that the sum p+q is not higher than 3.

Formulae (4A) to (4D) and (5A) to (5D) contain one or more hydrophilic substituents. It will be understood that these hydrophilic substituents can be provided by the hydrophilic side chain of the amino acids from which the hydrophilic amino acid units are derived. However, depending on the way in which the units are linked, this is not necessarily the case.

Each of the hydrophilic substituents as defined for formulae (4A) to (4D) and (5A) to (5D) preferably comprises, independently for each occurrence, at least one hydrophilic functional group selected from an amino group or N-methylated derivatives thereof, a carboxylic acid group, a hydroxy group, a guanidino group or N-methylated derivatives thereof, an amido group, and a urea group or N-methylated derivatives thereof, or from isosters of these groups. More preferably, each of the hydrophilic substituents defined for formulae (4A) to (4D), and (5A) to (5D) comprises, independently for each occurrence, at least one hydrophilic functional group selected from an amino group, a carboxylic acid group, a hydroxy group, a guanidino group, an amido group, and a urea group, or from isosters of these groups.

Still more preferably, each hydrophilic substituent as defined for formulae (4A) to (4D) and (5A) to (5D) is independently selected from a group $—(CH_2)_c—COOH$, a group $—(CH_2)_c—NH_2$ or N-methylated derivatives thereof, a group $—(CH_2)_c—CH(NH_2)—COOH$, a group $—(CH_2)_c—NH—C(O)—NH_2$ or N-methylated derivatives thereof and a group $—(CH_2)_c—NH—C(NH)—NH_2$ or N-methylated derivatives thereof, wherein c is an integer of 0 to 6. More preferably, the hydrophilic substituents are independently selected from a group $—(CH_2)_c—COOH$, a group $—(CH_2)_c—NH_2$, a group $—(CH_2)_c—CH(NH_2)—COOH$, a group $—(CH_2)_c—NH—C(O)—NH_2$ and a group $—(CH_2)_c—NH—C(NH)—NH_2$, wherein c is an integer of 0 to 6.

In line with the above, it is particularly preferred that in each of formulae (4A) to (4D) and (5A) to (5D) at least one hydrophilic substituent is a group $—(CH_2)_c—COOH$, wherein c is an integer of 0 to 6.

Formulae (4E), (4F), (5C) and (5D) may contain a non-hydrophilic substituent. The non hydrophilic substituent is preferably an alkyl group (e.g. a C1-C6 alkyl group) or an aralkyl group (e.g. a benzyl group).

Ligand Moiety $R^L$

In the conjugate compounds in accordance with the invention, $R^L$ is a ligand moiety which is capable of binding to prostate-specific membrane antigen (PSMA). As discussed above, suitable ligand structures are known to the skilled person.

In the context of the present invention, the ligand moiety $R^L$ preferably has a structure represented by formula (6):

(6)

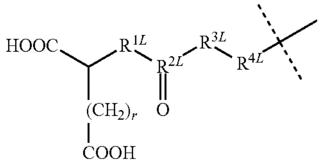

wherein r is an integer of 2 to 6, preferably 2 to 4, more preferably 2;

$R^{1L}$ is $CH_2$, NH or O, preferably NH;

$R^{2L}$ is C or P(OH), preferably C;

$R^{3L}$ is $CH_2$, NH or O, preferably NH;

$R^{4L}$ is a linear C1 to C7 alkanediyl group which carries a —COOH substituent; and wherein the dashed line marks the bond which attaches the moiety to the remainder of the conjugate compound.

More preferably, the ligand moiety $R^L$ has a structure represented by any one of formulae (6A) to (6D):

(6A)

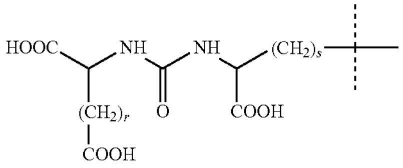

(6B)

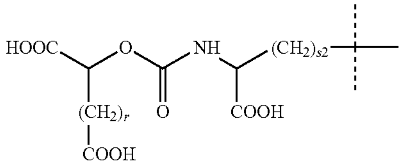

(6C)

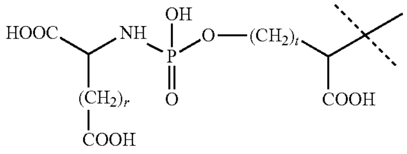

6D)

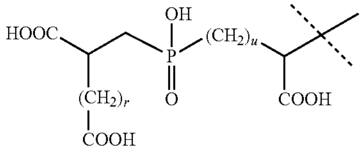

wherein r is an integer of 2 to 6, preferably 2 to 4, more preferably 2;

s is an integer of 2 to 6, preferably 2 to 4, more preferably 2 or 4;

s2 is an integer of 2 to 6, preferably 2 to 4, more preferably 4;

t is an integer of 1 to 4, preferably 1 to 3, more preferably 1 or 3;

u is an integer of 1 to 4, preferably 1 to 3, more preferably 1;

and wherein the dashed line marks the bond which attaches the moiety to the remainder of the conjugate compound.

Still more preferably, the ligand moiety $R^L$ has a structure represented by formula (6E):

(6E)

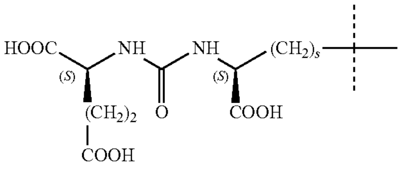

wherein s is an integer of 2 to 6, preferably 2 to 4, more preferably 2 or 4;

and wherein the dashed line marks the bond which attaches the moiety to the remainder of the conjugate compound. In one particularly preferred embodiment of the ligand moiety of formula (6E), s is 2 and the dashed line marks a bond which is attached to the carbon atom of an amide bond. In another particularly preferred embodiment of the ligand moiety of formula (6E), s is 4 and the dashed line marks a bond which is attached to the nitrogen atom of an amide bond.

Silicon-Fluoride Acceptor (SiFA) Moiety $R^{SiFA}$

As discussed above, the use of silicon fluoride acceptors (SiFA) for introducing $^{18}F$ labels is also known to the skilled person, and suitable SiFA groups have been described in the literature. In the compounds in accordance with the present invention, the SiFA moiety $R^{SiFA}$ preferably has a structure represented by formula (7):

(7)

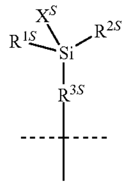

wherein $X^S$ is F, OH or H, preferably F;

$R^{1S}$ and $R^{2S}$ are independently a linear or branched C3 to C10 alkyl group, preferably $R^{1S}$ and $R^{2S}$ are independently selected from isopropyl and tert-butyl, and more preferably $R^{1S}$ and $R^{2S}$ are tert-butyl;

$R^{3S}$ is a C1 to C20 hydrocarbon group, wherein up to 3 carbon atoms may be replaced by a heteroatom selected from N, O and S; preferably $R^{3S}$ is a C6 to C10 hydrocarbon group which comprises an aromatic ring, and which may comprise one or more aliphatic units and wherein one carbon atom, also in the aromatic ring, may be replaced by a nitrogen atom; more preferably $R^{3S}$ is a phenyl ring, and most preferably, $R^{3S}$ is a phenyl ring wherein the Si-containing substituent and the bond marked by the dashed line are in a para-position, and wherein the dashed line marks the bond which attaches the moiety to the remainder of the conjugate compound.

More preferably, the SiFA moiety $R^{SiFA}$ has a structure represented by formula (7A):

(7A)

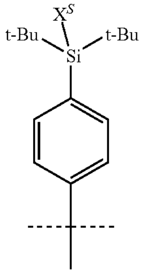

wherein
$X^S$ is F, OH or H, preferably F;
t-Bu indicates a tert-butyl group; and
the dashed line marks the bond which attaches the moiety to the remainder of the conjugate compound.

Most preferably, the SiFA moiety $R^{SiFA}$ has a structure represented by formula (7B):

(7B)

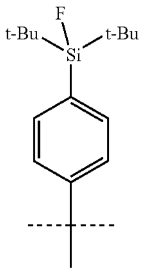

wherein
t-Bu indicates a tert-butyl group; and
the dashed line marks the bond which attaches the moiety to the remainder of the conjugate compound.

Linking Moiety L

Linking moieties which can be used to attach further functional moieties to a PSMA ligand are also known to the person skilled in the art.

For example, in the conjugate compound in accordance with the present invention, the linking moiety L preferably has a structure represented by formula (8A) or (8B):

(8A)

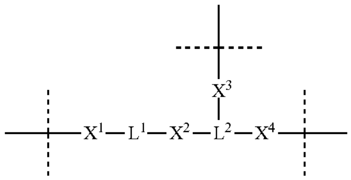

(8B)

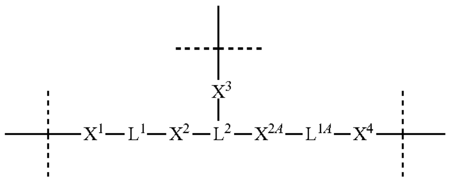

wherein
the bond marked with a dashed line at $X^1$ is formed with $R^L$, the bond marked with a dashed line at $X^3$ is formed with $R^{SiFA}$, and the bond marked with a dashed line at $X^4$ is formed with $R^H$;
$X^1$ is selected from an amide bond, an ether bond, a thioether bond, an ester bond, a thioester bond, a urea bond, a thiourea bond and an amine bond, and is preferably an amide bond;
$X^2$ is selected from an amide bond, an ether bond, a thioether bond, an ester bond, a thioester bond, a urea bond, a thiourea bond and an amine bond, and is preferably an amide bond;
$X^{2A}$ is selected from an amide bond, an ether bond, a thioether bond, an ester bond, a thioester bond, a urea bond, a thiourea bond and an amine bond, and is preferably an amide bond;
$X^3$ is selected from an amide bond, an ester bond, an ether bond, an amine bond, and a linking group of the formula:

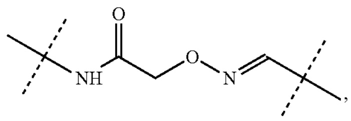, wherein the bond marked with a dashed line at the NH group is formed with $L^2$ and the other bond marked with a dashed line is formed with $R^{SiFA}$, preferably $X^3$ is an amide bond;
$X^4$ is a group which forms, in combination with a —NH— group or —C(O)— group contained in an amino acid unit of —$R^H$, or taken in combination with a coupling unit contained in $R^H$, an amide bond, an ester bond, a thioester bond, or a urea bond; more preferably $X^4$ is —C(O)— or —NH— and forms an amide bond with a corresponding group —NH— or —C(O)— of the first amino acid unit in the sequence of amino acid units of $R^H$ which is attached via $X^4$;
$L^1$ is a divalent linking group comprising a continuous chain of 6 to 36 atoms, preferably 6 to 24 atoms extending from $X^1$ to $X^2$, wherein said chain is formed by carbon atoms and optional heteroatoms which are selected, independently for each occurrence if more than one heteroatom is present, from N, O and S, and wherein the chain may comprise one or more divalent cyclic or heterocyclic groups, in which case all of the ring atoms are counted as atoms of the continuous chain;
$L^{1A}$ is a divalent linking group comprising a continuous chain of 6 to 24 atoms, preferably 6 to 18 atoms, extending from $X^{2A}$ to $X^4$, wherein said chain is formed by carbon atoms and optional heteroatoms which are selected, independently for each occurrence if more than one heteroatom is present, from N, O and S, and wherein the chain may comprise one or more divalent cyclic or heterocyclic groups, in which case all of the ring atoms are counted as atoms of the continuous chain; and
$L^2$ is a trivalent moiety.

As regards the above definition of $L^1$ as a divalent linking group comprising a continuous chain of 6 to 36 atoms extending from $X^1$ to $X^2$, it will be understood that the number of atoms refers exclusively to those atoms which are bound to each other to form the chain extending from $X^1$ to $X^2$. Thus, for example, for a C6 alkanediyl group —$(CH_2)_6$— linking $X^1$ and $X^2$, the number of atoms in the continuous chain would be 6. Equally, if $L^1$ is a divalent linking group comprising functional groups, such as an amide bond, only those atoms in the functional groups which form part of the chain (e.g. —C—N— in the case of an amide bond) are counted. The same considerations apply with respect to $L^{1A}$ and the number of atoms defined for this group.

In the linking moiety of formula (8A), $L^2$ is preferably represented by formula (9):

(9)

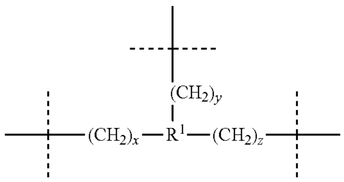

wherein $R^1$ is selected from N, $CR^2$, wherein $R^2$ is H or C1-C6 alkyl, and from a 5 to 7 membered carbocyclic or heterocyclic group; preferably $R^1$ is selected from N and CH, and more preferably $R^1$ is CH;

the bond marked by the dashed line at $(CH_2)_z$ is formed with $X^{2A}$, and z is an integer of 0 to 4, preferably of 0 to 2, and more preferably 0 or 1.

Moreover, $X^1$ is preferably an amide bond.

Similarly, $X^2$ and $X^{2A}$ are preferably an amide bond; $X^3$ is preferably an amide bond; and $X^4$ is preferably —C(O)— or —NH— and forms an amide bond with a corresponding group —NH— or —C(O)— of the first amino acid unit in the sequence of amino acid units of $R^H$ which is attached to $X^4$.

The trivalent moiety $L^2$ and functional groups required for forming the preferred amide bond $X^2$ and the preferred amide bond $X^3$, and for forming the preferred amide bond with a corresponding group —NH— or —C(O)— of the first amino acid unit in the sequence of amino acid units of $R^H$ or the preferred amide bond $X^{2A}$, is preferably provided by an amino acid selected from 2,3-diaminopropionic acid (Dap), 2,4-diaminobutanoic acid (Dab), ornithine (Orn), lysine (Lys), aspartic acid (Asp), glutamic acid (Glu) and homoglutamic acid (Hgl). This amino acid is preferably in D-configuration.

It is more preferred that the linking moiety L has a structure represented by formula (10A) or (10B):

(10)

(10A)

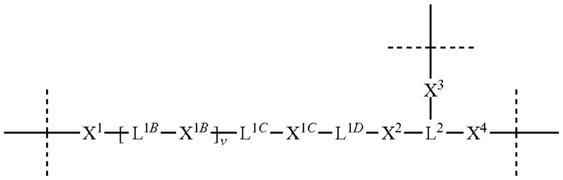

(10B)

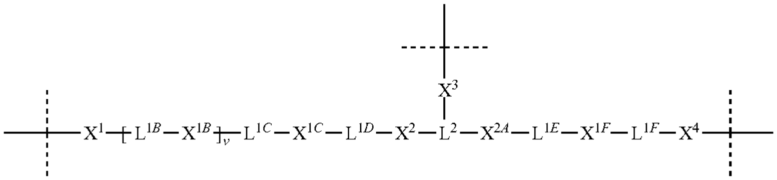

the bond marked by the dashed line at $(CH_2)_x$ is formed with $X^2$, and x is an integer of 0 to 4, preferably 0 or 1, and most preferably 0;

the bond marked by the dashed line at $(CH_2)_y$ is formed with $X^3$, and y is an integer of 0 to 4, preferably of 0 to 2, and more preferably 0 or 1; and the bond marked by the dashed line at $(CH_2)_z$ is formed with $X^4$, and z is an integer of 0 to 4, preferably of 0 to 2, and more preferably 0 or 1.

In the linking moiety of formula (8B), $L^2$ is preferably represented by formula (9) as shown above, wherein $R^1$ is selected from N, $CR^2$, wherein $R^2$ is H or C1-C6 alkyl, and from a 5 to 7 membered carbocyclic or heterocyclic group; preferably $R^1$ is selected from N and CH, and more preferably $R^1$ is CH;

the bond marked by the dashed line at $(CH_2)_x$ is formed with $X^2$, and x is an integer of 0 to 4, preferably 0 or 1, and most preferably 0;

the bond marked by the dashed line at $(CH_2)_y$ is formed with $X^3$, and y is an integer of 0 to 4, preferably of 0 to 2, and more preferably 0 or 1; and wherein:

$X^1$, $X^2$, $X^{2A}$, $X^3$, $X^4$ and $L^2$ are as defined for formula (8A) and (8B) and their preferred embodiments above;

v is 0 or 1;

$L^{1B}$ is an optionally substituted C1-C8 alkanediyl group, preferably a linear alkanediyl group, which may be interrupted by an ether bond and wherein, if the alkanediyl group comprises a chain of 4 or more carbon atoms, 4 consecutive carbon atoms in the chain may be replaced by a benzenediyl group or a cyclohexanediyl group;

$L^{1C}$ and $L^{1F}$ are independently an optionally substituted C1-C8 alkanediyl group, preferably a linear alkanediyl group, which may be interrupted by an ether bond and wherein, if the alkanediyl group comprises a chain of 4 or more carbon atoms, 4 consecutive carbon atoms in the chain may be replaced by a benzenediyl group or a cyclohexanediyl group;

$L^{1D}$ and $L^{1E}$ are independently an optionally substituted C1-C8 alkanediyl group, preferably a linear alkanediyl group, which may be interrupted by an ether bond and wherein, if the alkanediyl group comprises a chain of 4 or more carbon atoms, 4 consecutive carbon atoms in the chain may be replaced by a benzenediyl group or a cyclohexanediyl group;

$X^{1B}$ is selected from an amide bond, an ether bond, a thioether bond, an ester bond, a thioester bond, a urea bond, a thiourea bond and an amine bond, and are preferably an amide bond; and $X^{1C}$ and $X^{1F}$ are independently selected from an amide bond, an ether bond, a thioether bond, an ester bond, a thioester bond, a urea bond, a thiourea bond and an amine bond, and are preferably an amide bond.

Preferably, the optional substituent(s) of $L^{1B}$, $L^{1C}$ and $L^{1D}$ in formula (10A) and (10B) and the optional substituents of $L^{1E}$, and $L^{1F}$ in formula (10B) is (are) independently selected from —OH, —$OCH_3$, —COOH, —$COOCH_3$, —$NH_2$, —NHR; —NHC(NH)$NH_2$, phenyl, pyridinyl, naphthyl, —$CH_2$-phenyl, —$CH_2$-pyridinyl and —$CH_2$-naphtyl, wherein the group R in the substituent —NHR is an acyl group, and wherein any phenyl group may be further substituted by one or more substituents selected from halogen, preferably —F or —I, and —OH. An example of an acyl group suitable as R is an acyl group derived from trimesic acid.

More preferably, the optional substituent(s) of $L^{1B}$ is (are) independently selected from —COOH, —$NH_2$, —$CH_2$-phenyl, —$CH_2$-pridinyl and —$CH_2$-naphtyl, wherein any phenyl group may be further substituted by one or more substituents selected from halogen, preferably —F or —I, and —OH;

and the optional substituent(s) of $L^{1C}$, $L^{1F}$ $L^{1D}$ and $L^{1E}$ is (are) independently selected from —COOH, —NHR and —$NH_2$.

It is further preferred that the groups $L^{1B}$, $L^{1C}$, $L^{1D}$, $L^{1E}$, and $L^{1F}$ are, independently, unsubstituted or comprise one substituent.

Furthermore, it is preferred for the linking moiety of formula (10A) and (10B) that $X^{1B}$ is selected from an amide bond and a urea bond, and is more preferably an amide bond; and $X^{1C}$ and $X^{1F}$ are independently selected from an amide bond and a urea bond, and are more preferably an amide bond.

For example, in the linking group of formula (10A) or (10B), v may be 1 and —$X^1$-$L^{1B}$-$X^{1B}$-$L^{1C}$-$X^{1C}$-$L^{1D}$-$X^2$— may be represented by the divalent group of formula (11A) or (11B):

*—C(O)—NH—$R^3$—NH—C(O)—$R^4$—C(O)—NH—$R^5$—NH—C(O)— (11A)

*—C(O)—NH—$R^6$—NH—C(O)—$R^7$—NH—C(O)—$R^8$—NH—C(O)— (11B)

wherein $R^3$ to $R^8$ are independently selected from C2 to C8 alkanediyl, preferably linear C2 to C8 alkanediyl, which alkanediyl groups may each be substituted by one or more substitutents independently selected from —OH, —$OCH_3$, —COOH, —$COOCH_3$, —$NH_2$, —NHR and —NHC(NH)$NH_2$, wherein R is an acyl group as defined above;

and wherein * marks the $X^1$ terminal of the group.

Similarly, in the linking group of formula (10B), —$X^{2A}$-$L^{1E}$-$X^{1F}$-$L^{1F}$-$X^4$— may be represented by the divalent group of formula (11C), (11D) or (11E):

—C(O)—NH—$R^9$—NH—C(O)—$R^{10}$—C(O)—NH—* (11C)

—C(O)—NH—$R^{11}$—C(O)—NH—$R^{12}$—C(O)—NH—* (11D)

—NH—C(O)—$R^{13}$—NH—C(O)—$R^{14}$—NH—C(O)—* (11E)

wherein $R^9$ to $R^{14}$ are independently selected from C1 to C8 alkanediyl, preferably linear C1 to C8 alkanediyl, which alkanediyl groups may each be substituted by one or more substitutents independently selected from —OH, —$OCH_3$, —COOH, —$COOCH_3$, —$NH_2$, —NHR and —NHC(NH)$NH_2$, wherein R is an acyl group as defined above;

and wherein * marks the $X^4$ terminal of the group.

In another, more preferred example, in the linking group of formula (10A) or (10B), v may be 1 and —$X^1$-$L^{1B}$-$X^{1B}$-$L^{1C}$-$X^{1C}$-$L^{1D}$-$X^2$— may be represented by the divalent group of formula (12A) or (12B)

*—C(O)—NH—CH(COOH)—$R^{15}$—NH—C(O)—$R^{16}$—C(O)—NH—$R^{17}$—CH(COOH)—NH—C(O)— (12A)

*—C(O)—NH—CH(COOH)—$R^{18}$—NH—C(O)—$R^{19}$—NH—C(O)—$R^{20}$—CH(COOH)—NH—C(O)— (12B)

wherein $R^{15}$ to $R^{20}$ are independently selected from C2 to C8 alkanediyl, preferably linear C2 to C8 alkanediyl, and $R^{16}$ or $R^{19}$ is optionally substituted by —NHR, wherein R is an acyl group as defined above, and wherein * marks the $X^1$ terminal of the group.

Similarly, in the linking group of formula (10B), —$X^{2A}$-$L^{1E}$-$X^{1F}$-$L^{1F}$-$X^4$— may be represented by the divalent group of formula (12C), (12D) or (12E) as more preferred examples thereof:

—C(O)—NH—CH(COOH)—$R^{21}$—NH—C(O)—$R^{22}$—C(O)—NH—* (12C)

—C(O)—NH—CH(COOH)—$R^{23}$—C(O)—NH—$R^{24}$—C(O)—NH—* (12D)

—NH—C(O)—$R^{25}$—NH—C(O)—$R^{26}$—NH—C(O)—* (12E)

wherein $R^{21}$ to $R^{22}$ are independently selected from C1 to C8 alkanediyl, preferably linear C1 to C8 alkanediyl, and $R^{22}$ or $R^{24}$ is optionally substituted by —NHR, wherein R is an acyl group as defined above, $R^{25}$ and $R^{26}$ are independently selected from C1 to C3 alkanediyl, preferably linear C1 to C3 alkanediyl, and wherein * marks the $X^4$ terminal of the group.

As will be apparent from the above, a preferred formula for the conjugate compound in accordance with the invention is formula (1A) or pharmaceutically acceptable salts thereof, wherein the variables have the meanings defined above, including preferred embodiments thereof:

(1A)

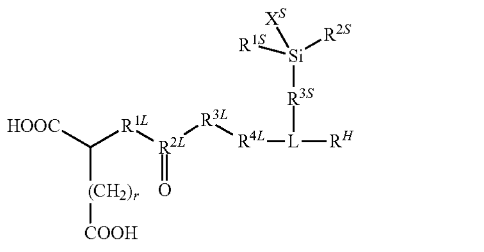

Moreover, further preferred conjugate compounds in accordance with the invention are those of formulae (1B) to (1F) or pharmaceutically acceptable salts thereof, wherein the variables have the meanings defined above, including their preferred embodiments.

(1B)

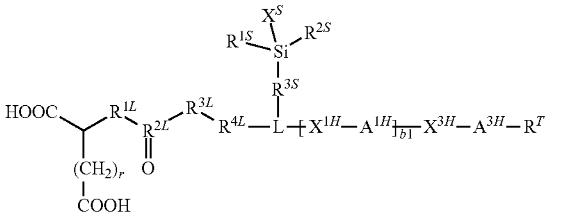

(1C)

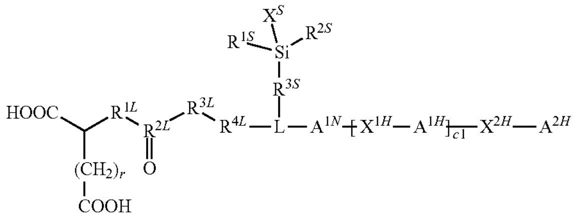

(1D)

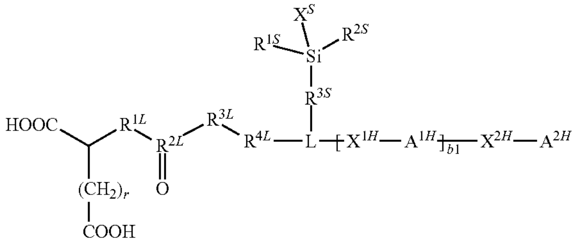

(1E)

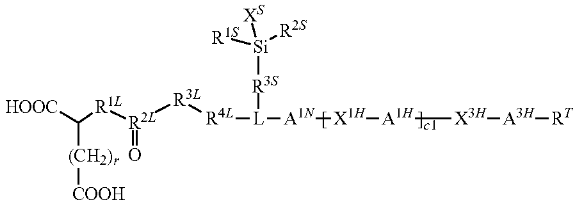

(IF)

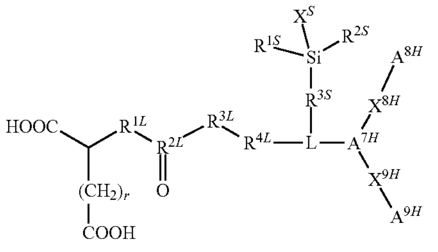

Even further preferred conjugate compounds in accordance with the invention are those of formulae (1G) and (1H) or pharmaceutically acceptable salts thereof, wherein the variables have the meanings defined above, including their preferred embodiments.

(1G)

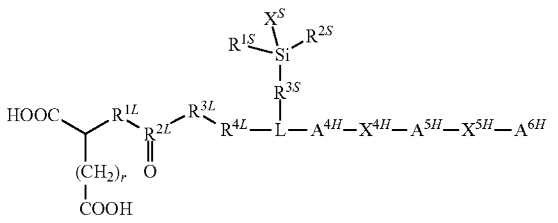

(1H)

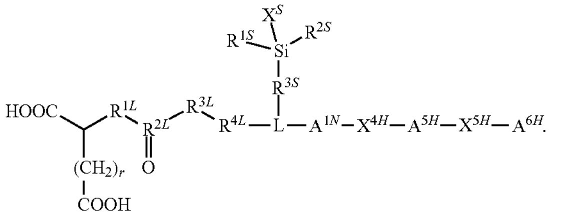

Moreover, in line with the above, it will be understood that still further preferred conjugate compounds in accordance with the invention are those of formulae (1I) and (1J) or pharmaceutically acceptable salts thereof, wherein the variables have the meanings defined above, including their preferred embodiments.

(1I)

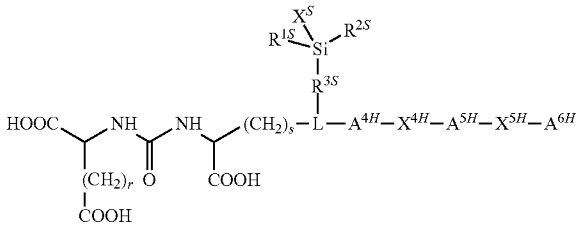

(1J)

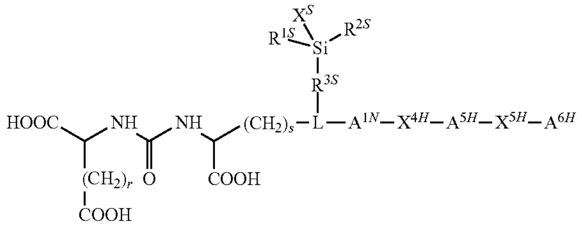

In a further aspect, the present invention provides a diagnostic composition comprising or consisting of one or more compounds or salts of the invention as disclosed herein above. It is understood that the term “radiopharmaceutical” as used herein embraces diagnostically active agents as well as diagnostic compositions comprising or consisting of diagnostically active agents. Compounds of the invention are useful as diagnostically active agents.

In a further aspect, the present invention provides a pharmaceutical composition comprising or consisting of one or more compounds or salts of the invention as disclosed herein above.

In a further aspect, the present invention provides a therapeutic composition comprising or consisting of one or more compounds or salts of the invention as disclosed herein above.

The pharmaceutical, diagnostic or therapeutic composition may further comprise pharmaceutically acceptable carriers, excipients and/or diluents. Examples of suitable pharmaceutical carriers, excipients and/or diluents are well known in the art and include phosphate buffered saline solutions, isotonic saline, or other buffer solutions for intravenous injections, water, emulsions, such as oil/water emulsions, various types of wetting agents, sterile solutions, suitable and commonly used stabilizers to avoid and minimize radiolytic decomposition, such as ethanol, other alcohols, gentisic acid, ascorbic acid etc. Compositions comprising such carriers can be formulated by well known conventional methods. These pharmaceutical compositions can be administered to the subject at a suitable dose. Administration of the suitable compositions may be effected by different ways, e.g., by intravenous, intraperitoneal, subcutaneous, intramuscular, topical, intradermal, intranasal or intrabronchial administration. It is particularly preferred that said administration is carried out by injection, in particular intravenous injection for diagnostic preparations and intravenous injection or continuous infusions for therapeutic preparations. The compositions may also be administered directly to the target site. The dosage regimen will be determined by the attending physician/surgeon and clinical factors. As is well known in the medical arts, dosages for any one patient depends upon many factors, including the patient's size, body surface area, age, tumor load, organ function, individual dosimetry, the particular compound to be administered, sex, time and route of administration, general health, and other drugs being administered concurrently. Pharmaceutically active matter may be present in amounts between 0.1 ng and 10 mg/kg, preferably between 0.1 ng and 500 μg, more preferably between 0.1 ng and 200 μg per dose per patient; however, doses below or above this exemplary range are envisioned, especially considering the aforementioned factors.

To the extent the above disclosed pharmaceutical composition, diagnostic composition and therapeutic composition comprises one or more compounds of the invention, it is preferred that no further pharmaceutically active compounds, diagnostically active compounds or therapeutically active compounds are present. In the alternative, further therapeutically active, diagnostically active or pharmaceutically active compounds may be present, for example, anticancer agents.

In a further aspect, the present invention provides one or more conjugate compounds or salts of the invention as disclosed herein above for use in medicine.

Uses in medicine are in nuclear medicine such as nuclear diagnostic imaging, also named nuclear molecular imaging, and/or targeted radiotherapy of diseases associated with an overexpression of PSMA on the diseased tissue. Said imaging includes imaging during a surgical intervention, wherein compounds of the invention as comprised in a diagnostic composition of the invention are employed to guide the surgeon to neoplastic tissue. Preferably, the surgical intervention is not comprised by the invention.

In a further aspect, the present invention provides a compound or salt of the invention as defined herein above for use in a method of diagnosing and/or staging cancer, preferably prostate cancer.

Preferred indications are the detection or staging of cancer, such as, but not limited high grade gliomas, lung cancer and especially prostate cancer and metastasized prostate cancer, the detection of metastatic disease in patients with primary prostate cancer of intermediate-risk to high-risk, and the detection of metastatic sites, even at low serum PSA values in patients with biochemically recurrent prostate cancer. Another preferred indication is the imaging and visualization of neoangiogensis.

In terms of medical indications to be subjected to therapy, especially radiotherapy, cancer is a preferred indication. Prostate cancer is a particularly preferred indication.

In a further aspect, the present invention provides a compound or salt of the invention as defined herein above for use in a method of diagnosing and/or staging cancer, preferably prostate cancer.

As regards the embodiments characterized in this specification, in particular in the claims, it is intended that each embodiment mentioned in a dependent claim is combined with each embodiment of each claim (independent or dependent) said dependent claim depends from. For example, in case of an independent claim 1 reciting 3 alternatives A, B and C, a dependent claim 2 reciting 3 alternatives D, E and F and a claim 3 depending from claims 1 and 2 and reciting 3 alternatives G, H and I, it is to be understood that the specification unambiguously discloses embodiments corresponding to combinations A, D, G; A, D, H; A, D, I; A, E, G; A, E, H; A, E, I; A, F, G; A, F, H; A, F, I; B, D, G; B, D, H; B, D, I; B, E, G; B, E, H; B, E, I; B, F, G; B, F, H; B, F, I; C, D, G; C, D, H; C, D, I; C, E, G; C, E, H; C, E, I; C, F, G; C, F, H; C, F, I, unless specifically mentioned otherwise.

Similarly, and also in those cases where independent and/or dependent claims do not recite alternatives, it is understood that if dependent claims refer back to a plurality of preceding claims, any combination of subject-matter covered thereby is considered to be explicitly disclosed. For example, in case of an independent claim 1, a dependent claim 2 referring back to claim 1, and a dependent claim 3 referring back to both claims 2 and 1, it follows that the combination of the subject-matter of claims 3 and 1 is clearly and unambiguously disclosed as is the combination of the subject-matter of claims 3, 2 and 1. In case a further dependent claim 4 is present which refers to any one of claims 1 to 3, it follows that the combination of the subject-matter of claims 4 and 1, of claims 4, 2 and 1, of claims 4, 3 and 1, as well as of claims 4, 3, 2 and 1 is clearly and unambiguously disclosed.

The following items provide a summary of the invention and its preferred embodiments.

1. A ligand-SiFA conjugate compound represented by formula (1)

(1)

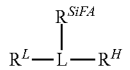

wherein:

$R^L$ is a ligand moiety which is capable of binding to prostate-specific membrane antigen (PSMA);

$R^{SiFA}$ is a silicon-fluoride acceptor (SiFA) moiety selected from:

(i) a SiFA moiety which comprises a silicon atom and a fluorine atom, wherein the fluorine atom is linked via a covalent bond directly to the silicon atom, and which SiFA moiety can be labeled with $^{18}F$ by isotopic exchange of $^{19}F$ by $^{18}F$ or which is labeled with $^{18}F$; and (ii) a SiFA moiety which comprises a silicon atom and a hydroxy group, wherein the hydroxy group is linked via a covalent bond directly to the silicon atom, and which SiFA moiety can be labeled with $^{18}F$ by nucleophilic substitution of OH by $^{18}F$;

(iii) a SiFA moiety which comprises a silicon atom and a hydrogen atom, wherein the hydrogen atom is linked via a covalent bond directly to the silicon atom, and which SiFA moiety can be labeled with $^{18}F$ by nucleophilic substitution of H by $^{18}F$;

L is a linking moiety;

$R^H$ is a hydrophilic moiety which comprises (i) a linear or branched sequence of 2 to 10 hydrophilic amino acid units $A^H$, each of which is independently derived from a natural or non-natural amino acid carrying a hydrophilic side chain, and optionally one amino acid unit AN derived from a natural or non-natural amino acid which is devoid of a hydrophilic side chain, wherein the hydrophilic amino acid units and, if present, the unit $A^N$, are bound to each other via a direct covalent bond or via a coupling unit;

and which optionally further comprises (ii) one or more hydrophilic residues $R^T$, each of which may be bound to an amino group, a carboxylic acid group, or to a functional group of a hydrophilic side chain of an amino acid unit;

or a pharmaceutically acceptable salt thereof.

2. The conjugate compound in accordance with item 1, wherein the moiety —$R^H$ has a structure represented by formula (2):

$$—R^{1H}(—R^T)_{a1} \quad (2)$$

wherein $R^{1H}$ represents a linear or branched, preferably linear, sequence of 2 to 10 hydrophilic amino acid units, each of which is independently derived from a natural or non-natural amino acid carrying a hydrophilic side chain, and optionally one amino acid unit $A^N$ derived from a natural or non-natural amino acid which is devoid of a hydrophilic side chain, wherein the hydrophilic amino acid units and, if present, the unit $A^N$, are bound to each other via a direct covalent bond or via a coupling unit;

$R^T$ represents a hydrophilic residue which may be bound to an amino group, a carboxylic acid group, or to a functional group of a hydrophilic side chain of an amino acid unit, and a1 is 0 or 1;

or a pharmaceutically acceptable salt thereof.

3. The conjugate compound in accordance with item 1 or 2, wherein the moiety —$R^H$ has the structure represented by formula (3A), (3B), (3C) or (3D):

$$—[X^{1H}—A^{1H}]_{b1}—X^{2H}—A^{2H} \quad (3A)$$

$$—[X^{1H}—A^{1H}]_{b1}—X^{3H}—A^{3H}—R^T \quad (3B)$$

wherein b1 is an integer of 1 to 9;

$A^{1H}$, independently for each occurrence, is a hydrophilic amino acid unit derived from a natural or non-natural amino acid carrying a hydrophilic side chain;

$A^{2H}$ and $A^{3H}$ are each independently a hydrophilic amino acid unit derived from a natural or non-natural amino acid carrying a hydrophilic side chain;

$X^{1H}$, independently for each occurrence, is a bond or a coupling unit, $X^{2H}$ and $X^{3H}$ are each independently a bond or a coupling unit, and $R^T$ represents a hydrophilic residue which may be bound to an amino group, a carboxylic acid group, or to a functional group of a hydrophilic side chain of the amino acid unit $A^{3H}$ $$—A^{1N}—[X^{1H}—A^{1H}]_{c1}—X^{2H}—A^{2H} \quad (3C)$$

$$—A^{1N}—[X^{1H}—A^{1H}]_{c1}—X^{3H}—A^{3H}—R^T \quad (3D)$$

wherein c1 is an integer of 1 to 9; and preferably 1 to 4;

$A^{1N}$ is an amino acid unit derived from an amino acid which is devoid of a hydrophilic side chain;

$A^{1H}$, independently for each occurrence, is a hydrophilic amino acid unit derived from a (natural or non-natural) amino acid carrying a hydrophilic side chain;

$A^{2H}$ and $A^{3H}$ are each independently a hydrophilic amino acid unit derived from a (natural or non-natural) amino acid carrying a hydrophilic side chain;

$X^{1H}$, independently for each occurrence, is a bond or a coupling unit, $X^{2H}$ and $X^{3H}$ are each independently a bond or a coupling unit, and $R^T$ represents a hydrophilic residue which may be bound to an amino group, a carboxylic acid group, or to a functional group of a hydrophilic side chain of the amino acid unit $A^{3H}$;

or a pharmaceutically acceptable salt thereof.

4. The conjugate compound of item 3, wherein the moiety —$R^H$ has the structure represented by formula (3E) or (3F):

$$-A^{4H}-X^{4H}-A^{5H}-X^{5H}-A^{6H} \quad (3E),$$

$$-A^{1N}-X^{4H}-A^{5H}-X^{5H}-A^{6H} \quad (3F)$$

wherein $A^{4H}$, $A^{5H}$ and $A^{6H}$ are each independently a hydrophilic amino acid unit derived from a (natural or non-natural) amino acid carrying a hydrophilic side chain;

$X^{4H}$ and $X^{5H}$ are each independently a direct bond or a coupling unit and optionally a hydrophilic residue $R^T$ may be bound to an amino group, a carboxylic acid group, or to a functional group of a hydrophilic side chain of the amino acid unit $A^{6H}$; and $A^{1N}$ is an amino acid unit derived from an amino acid devoid of a hydrophilic side chain;

or a pharmaceutically acceptable salt thereof.

5. The conjugate compound of item 1, wherein the moiety —$R^H$ has the structure represented by formula (3G):

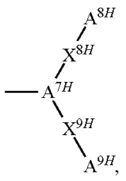

(3G)

wherein $A^{7H}$, $A^{8H}$ and $A^{9H}$ are each independently a hydrophilic amino acid unit derived from a natural or non-natural amino acid carrying a hydrophilic side chain; and $X^{8H}$ and $X^{9H}$ are each independently a direct bond or a coupling unit;

and optionally a hydrophilic residue $R^T$ may be bound to an amino group, a carboxylic acid group, or to a functional group of a hydrophilic side chain of one or both of the amino acid units $A^{8H}$ and $A^{9H}$;

or a pharmaceutically acceptable salt thereof.

6. The conjugate compound in accordance with any of items 1 to 5, wherein the hydrophilic moiety $R^T$ is selected from a chelator group, a chelate group with a complexed metal or radiometal, a carbohydrate residue, a polyethylene glycol residue, a reduced amino acid and an amino acid analogue with a carboxylic acid isoster;

or a pharmaceutically acceptable salt thereof.

7. The conjugate compound in accordance with any of items 1 to 6, wherein the hydrophilic amino acid units are, each independently, derived from an amino acid carrying a hydrophilic side chain which comprises at least one hydrophilic functional group selected from an amino group, a carboxylic acid group, a hydroxy group, a guanidino group, an amido group and a urea group or from isosters of these groups; or a pharmaceutically acceptable salt thereof.

8. The conjugate compound in accordance with any of items 1 to 6, wherein the hydrophilic amino acid units are, each independently, derived from an amino acid carrying a hydrophilic side chain selected from a group $-(CH_2)_c-COOH$, a group $-(CH_2)_c-NH_2$ or N-methylated derivatives thereof, a group $-(CH_2)_c-CH(NH_2)-COOH$, a group $-(CH_2)_c-NH-C(O)-NH_2$ or N-methylated derivatives thereof and a group $-(CH_2)_c-NH-C(NH)-NH_2$ or N-methylated derivatives thereof, wherein c is an integer of 0 to 6, preferably of 1 to 6;

or a pharmaceutically acceptable salt thereof.

9. The conjugate compound in accordance with any of items 1 to 8, wherein at least one of the hydrophilic amino acid units is derived from an amino acid carrying a group $-(CH_2)_c-COOH$, wherein c is an integer of 0 to 6, preferably of 1 to 6, as the hydrophilic side chain;

or a pharmaceutically acceptable salt thereof.

10. The conjugate compound in accordance with item 3 or 6, wherein the hydrophilic amino acid units $A^{1H}$, independently for each occurrence, and $A^{3H}$ have the structure represented by formula (4A) or (4B):

$$-NH-(CH_2)_a-(CHR^{2H})-(CH_2)_b-C(O)- \quad (4A)$$

$$-C(O)-(CH_2)_a-(CHR^{2H})-(CH_2)_b-NH- \quad (4B)$$

and the hydrophilic amino acid unit $A^{2H}$ has the structure represented by formula (4C) or (4D):

$$-NH-(CH_2)_a-(CHR^{2H})-(CH_2)_b-C(O)OH \quad (4C)$$

$$C(O)-(CH_2)_a-(CHR^{2H})-(CH_2)_b-NH_2 \quad (4D)$$

wherein, independently for each amino acid unit, a is an integer of 0 to 6, b is an integer of 0 to 6, with the proviso that the sum a+b is not higher than 6; and $R^{2H}$ is a hydrophilic substituent;

or a pharmaceutically acceptable salt thereof.

11. The conjugate compound in accordance with item 4, wherein the hydrophilic amino acid units $A^{4H}$ and $A^{5H}$ have the structure represented by formula (4A) or (4B):

$$-NH-(CH_2)_a-(CHR^{2H})-(CH_2)_b-C(O)- \quad (4A)$$

$$-C(O)-(CH_2)_a-(CHR^{2H})-(CH_2)_b-NH- \quad (4B)$$

and the hydrophilic amino acid unit $A^{6H}$ has the structure represented by formula (4C) or (4D):

$$-NH-(CH_2)_a-(CHR^{2H})-(CH_2)_b-C(O)OH \quad (4C)$$

$$-C(O)-(CH_2)_a-(CHR^{2H})-(CH_2)_b-NH_2 \quad (4D)$$

wherein, independently for each amino acid unit, a is an integer of 0 to 6, b is an integer of 0 to 6, with the proviso that the sum a+b is not higher than 6; and $R^{2H}$ is a hydrophilic substituent;

or a pharmaceutically acceptable salt thereof.

12. The conjugate compound according to any of items 3, 4 and 6 to 11, wherein the amino acid unit $A^{1N}$ derived from an amino acid devoid of a hydrophilic side chain preferably has the structure represented by formula (4E) or (4F):

$$-NH-(CH_2)_a-(CHR^{2N})-(CH_2)_b-C(O)- \quad (4E)$$

$$-C(O)-(CH_2)_a-(CHR^{2N})-(CH_2)_b-NH- \quad (4F).$$

wherein a is an integer of 0 to 6, b is an integer of 0 to 6, with the proviso that the sum a+b is not higher than 6; and $R^{2N}$ is H or a non-hydrophilic substituent.

13. The conjugate compound according to any of items 1 to 3 and 6 to 12, wherein $R^H$ comprises a total number of 3 to 10, more preferably 3 to 5, and still more preferably 3 hydrophilic amino acid units;

or a pharmaceutically acceptable salt thereof.

14. The conjugate compound according to any of items 1 to 13, wherein the hydrophilic amino acid units and, if present, the unit $A^N$, are bound to each other via a direct covalent bond or via a coupling unit —C(O)—, which coupling unit forms a urea bond —NH—C(O)—NH— with amino groups of two adjacent amino acid units comprised by $R^H$ or with an amino group of the linking moiety L and an amino group of an amino acid unit comprised by $R^H$;

or a pharmaceutically acceptable salt thereof.

15. The conjugate compound according to any of items 1 to 14, wherein the moiety —$R^H$ comprises at least one coupling unit —C(O)— forming a urea bond —NH—C(O)—NH— with amino groups of two adjacent amino acid units comprised by $R^H$ or with an amino group of the linking moiety L and an amino group of an amino acid unit comprised by $R^H$;

or a pharmaceutically acceptable salt thereof.

16. The conjugate compound in accordance with any of items 1 to 4 and 6 to 12, wherein the moiety $—R^H$ has a structure represented by formula (5A), (5B), (5C) or (5D):

$$—C(O)—(CH_2)_d—CHR^{3H}—(CH_2)_e—NH—C(O)—(CH_2)_f—CHR^{4H}—(CH_2)_g—NH—C(O)—NH—(CH_2)_h—CHR^{5H}—(CH_2)_i—COOH \quad (5A),$$

wherein
$R^{3H}$ to $R^{5H}$ are independently a hydrophilic substituent;
d is an integer of 0 to 3, e is an integer of 0 to 3, with the proviso that the sum d+e is not higher than 3;
f is an integer of 0 to 3, g is an integer of 0 to 3, with the proviso that the sum f+g is not higher than 3;
h is an integer of 0 to 3, i is an integer of 0 to 3, with the proviso that the sum h+i is not higher than 3;

$$—C(O)—(CH_2)—CHR^{6H}—(CH_2)_k—NH—C(O)—(CH_2)_m—CHR^{7H}—(CH_2)_n—NH—C(O)—(CH_2)_p—CHR^{8H}—(CH_2)_q—NH_2 \quad (5B),$$

wherein
$R^{6H}$ to $R^{8H}$ are independently a hydrophilic substituent;
j is an integer of 0 to 3, k is an integer of 0 to 3, with the proviso that the sum j+k is not higher than 3;
m is an integer of 0 to 3, n is an integer of 0 to 3, with the proviso that the sum m+n is not higher than 3;
p is an integer of 0 to 3, q is an integer of 0 to 3, with the proviso that the sum p+q is not higher than 3:

$$—C(O)—(CH_2)_d—CHR^{3N}—(CH_2)_e—NH—C(O)—(CH_2)_f—CHR^{4H}—(CH_2)_g—NH—C(O)—NH—(CH_2)_h—CHR^{5H}—(CH_2)_i—COOH \quad (5C),$$

wherein
$R^{3N}$ is H or a non-hydrophilic substituent;
$R^{4H}$ and $R^{5H}$ are independently a hydrophilic substituent;
d is an integer of 0 to 3, e is an integer of 0 to 3, with the proviso that the sum d+e is not higher than 3;
f is an integer of 0 to 3, g is an integer of 0 to 3, with the proviso that the sum f+g is not higher than 3;
h is an integer of 0 to 3, i is an integer of 0 to 3, with the proviso that the sum h+i is not higher than 3;

$$—C(O)—(CH_2)_j—CHR^{6N}—(CH_2)_k—NH—C(O)—(CH_2)_m—CHR^{7H}—(CH_2)_n—NH—C(O)—(CH_2)_p—CHR^{8H}—(CH_2)_q—NH_2 \quad (5D),$$

wherein
$R^{6N}$ is H or a non-hydrophilic substituent;
$R^{7H}$ and $R^{8H}$ are independently a hydrophilic substituent;
j is an integer of 0 to 3, k is an integer of 0 to 3, with the proviso that the sum j+k is not higher than 3;
m is an integer of 0 to 3, n is an integer of 0 to 3, with the proviso that the sum m+n is not higher than 3;
p is an integer of 0 to 3, q is an integer of 0 to 3, with the proviso that the sum p+q is not higher than 3;
or a pharmaceutically acceptable salt thereof.

17. The conjugate compound in accordance with any of items 11 to 16, wherein each hydrophilic substituent comprises, independently for each occurrence, at least one hydrophilic functional group selected from an amino group, a carboxylic acid group, a hydroxy group, a guanidino group, an amido group and a urea group, or from isosters of these groups;
or a pharmaceutically acceptable salt thereof.

18. The conjugate compound in accordance with any of items 11 to 16, wherein each hydrophilic substituent is independently selected from a group $—(CH_2)—COOH$, a group $—(CH_2)_c—NH_2$ or N-methylated derivatives thereof, a group $—(CH_2)_c—CH(NH_2)—COOH$, a group $—(CH_2)_c—NH—C(O)—NH_2$ or N-methylated derivatives thereof and a group $—(CH_2)_c—NH—C(NH)—NH_2$ or N-methylated derivatives thereof, wherein c is an integer of 0 to 6;
or a pharmaceutically acceptable salt thereof.

19. The conjugate compound in accordance with any of items 11 to 18, wherein at least one hydrophilic substituent is a group $—(CH_2)_c—COOH$, wherein c is an integer of 0 to 6; or a pharmaceutically acceptable salt thereof.

20. The conjugate compound in accordance with any of items 12 to 19, wherein the non hydrophilic substituent is an alkyl group or an aralkyl group;
or a pharmaceutically acceptable salt thereof.

21. The conjugate compound according to any of items 1 to 19, wherein the hydrophilic amino acid units in the moiety $—R^H$ are each independently derived from an amino acid selected from 2,3-diaminopropionic acid (Dap), 2,4-diaminobutanoic acid (Dab), ornithine (Orn), lysine (Lys), 4-aminopiperidine-4-carboxylic acid (Apc4), 3-aminopiperidine-3-carboxylic acid (Apc3), 2-aminopiperidine-2-carboxylic acid (Apc2), aspartic acid (Asp), homoglutamic acid (Hgl), glutamic acid (Glu), 2,3-diaminosuccinic acid, diaminopentanedioic acid, diaminohexanedioic acid, diaminoheptanedioic acid, diaminooctanedioic acid, threonine (Thr) and citrulline (Cit), and wherein the amino acids are preferably in D-configuration;
or a pharmaceutically acceptable salt thereof.

22. The conjugate compound according to item 21, wherein the hydrophilic amino acid units in the moiety $—R^H$ are each independently derived from an amino acid selected from 2,3-diaminopropionic acid (Dap), ornithine (Orn), lysine (Lys), threonine (Thr), aspartic acid (Asp), glutamic acid (Glu), and citrulline (Cit), and wherein the amino acids are preferably in D-configuration;
or a pharmaceutically acceptable salt thereof.

23. The conjugate compound according to any of items 1 to 4 and 6 to 22, wherein any amino acid unit derived from an amino acid devoid of a hydrophilic side chain in the moiety $—R^H$ is derived from an amino acid selected from glycine (Gly), phenylalanine (Phe), β-alanine (β-Ala) and aminohexanoic acid (Ahx);
or a pharmaceutically acceptable salt thereof.

24. The conjugate compound of item 4, wherein, in formula (3E), each of $A^{4H}$, $A^{5H}$, and $A^{6H}$ is independently an amino acid unit derived from an amino acid selected from 2,3-diaminopropionic acid (Dap), ornithine (Orn), lysine (Lys), threonine (Thr), aspartic acid (Asp), glutamic acid (Glu), and citrulline (Cit), and each of $X^{4H}$ and $X^{5H}$ is independently a bond or a coupling unit —C(O)—, which coupling unit forms a urea bond with amino groups of two adjacent amino acid units;
or a pharmaceutically acceptable salt thereof.

25. The conjugate compound of item 24, wherein the amino acid unit $A^{4H}$ is derived from an amino acid selected from 2,3-diaminopropionic acid (Dap), ornithine (Orn), lysine (Lys), threonine (Thr), aspartic acid (Asp), glutamic acid (Glu), and citrulline (Cit), $A^{5H}$ and $A^{6H}$ are amino acid units derived from glutamic acid, $X^{4H}$ is a bond and $X^{5H}$ is selected from a bond and a coupling unit —C(O)—, which coupling unit forms a urea bond with amino groups of two adjacent amino acid units; or the amino acid unit $A^{4H}$ is derived from an amino acid selected from 2,3-diaminopropionic acid (Dap), ornithine (Orn), lysine (Lys), threonine (Thr), aspartic acid (Asp), glutamic acid (Glu), and citrulline (Cit), $A^{5H}$ and $A^{6H}$ are amino acid units derived from citrulline, and $X^{4H}$ and $X^{5H}$ are each a bond;

or a pharmaceutically acceptable salt thereof.

26. The conjugate compound of item 4, wherein, in formula (3F), $A^{1N}$ is an amino acid unit derived from glycine (Gly), phenylalanine (Phe), β-alanine (β-Ala) and aminohexanoic acid (Ahx), $A^{5H}$ and $A^{6H}$ are independently derived from an amino acid selected from 2,3-diaminopropionic acid (Dap), ornithine (Orn), lysine (Lys), threonine (Thr), aspartic acid (Asp), glutamic acid (Glu), and citrulline (Cit), and each of $X^{4H}$ and $X^{5H}$ is independently a bond or a coupling unit —C(O)—, which coupling unit forms a urea bond with amino groups of two adjacent amino acid units;

or a pharmaceutically acceptable salt thereof.

27. The conjugate compound in accordance with any of items 1 to 26, wherein the ligand moiety $R^L$ has a structure represented by formula (6):

(6)

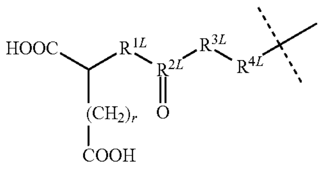

wherein r is an integer of 2 to 6, preferably 2 to 4, more preferably 2;

$R^{1L}$ is $CH_2$, NH or O, preferably NH;

$R^{2L}$ is C or P(OH), preferably C;

$R^{3L}$ is $CH_2$, NH or O, preferably NH;

$R^{4L}$ is a linear C1 to C7 alkanediyl group which carries a —COOH substituent; and wherein the dashed line marks the bond which attaches the moiety to the remainder of the conjugate compound;

or a pharmaceutically acceptable salt thereof.

28. The conjugate compound in accordance with item 27, wherein the ligand moiety $R^L$ has a structure represented by formula (6A), (6B), (6C) or (6D):

(6A)

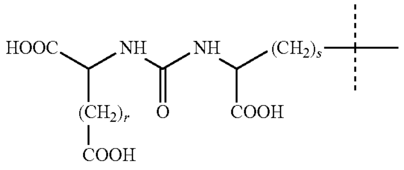

(6B)

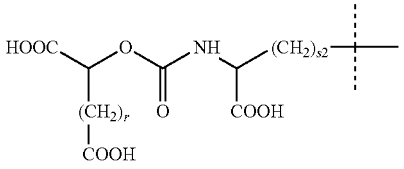

-continued (6C)

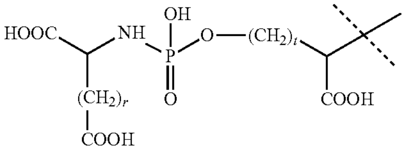

(6D)

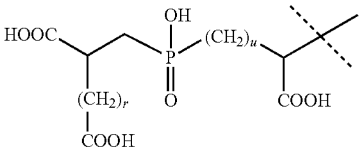

wherein r is an integer of 2 to 6, preferably 2 to 4, more preferably 2;

s is an integer of 2 to 6, preferably 2 to 4, more preferably 2 or 4;

s2 is an integer of 2 to 6, preferably 2 to 4, more preferably 4;

t is an integer of 1 to 4, preferably 1 to 3, more preferably 1 or 3;

u is an integer of 1 to 4, preferably 1 to 3, more preferably 1;

and wherein the dashed line marks the bond which attaches the moiety to the remainder of the conjugate compound;

or a pharmaceutically acceptable salt thereof.

29. The conjugate compound in accordance with item 27, wherein the ligand moiety $R^L$ has a structure represented by formula (6E):

(6E)

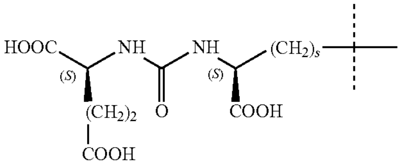

wherein s is an integer of 2 to 6, preferably 2 to 4, more preferably 2 or 4;

and wherein the dashed line marks the bond which attaches the moiety to the remainder of the conjugate compound;

or a pharmaceutically acceptable salt thereof.

30. The conjugate compound in accordance with any of items 1 to 29, wherein the SiFA moiety $R^{SiFA}$ has a structure represented by formula (7):

(7)

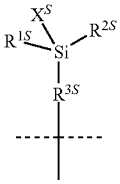

wherein $X^{S}$ is F, OH or H, preferably F;

$R^{1S}$ and $R^{2S}$ are independently a linear or branched C3 to C10 alkyl group, preferably $R^{1S}$ and $R^{2S}$ are independently selected from isopropyl and tert-butyl, and more preferably $R^{1S}$ and $R^{2S}$ are tert-butyl;

$R^{3S}$ is a C1 to C20 hydrocarbon group, wherein up to 3 carbon atoms may be replaced by a heteroatom selected from N, O and S; preferably $R^{3S}$ is a C6 to C10 hydrocarbon group which comprises an aromatic ring, and which may comprise one or more aliphatic units and wherein one carbon atom, also in the aromatic ring, may be replaced by a nitrogen atom; more preferably $R^{3S}$ is a phenyl ring, and most preferably, $R^{3S}$ is a phenyl ring wherein the Si-containing substituent and the bond marked by the dashed line are in a para-position, and wherein the dashed line marks the bond which attaches the moiety to the remainder of the conjugate compound;

or a pharmaceutically acceptable salt thereof.

31. The conjugate compound in accordance with item 30, wherein the SiFA moiety $R^{SiFA}$ has a structure represented by formula (7A):

(7A)

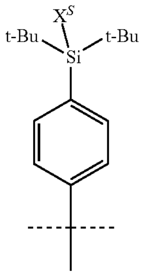

wherein $X^{S}$ is F, OH or H, preferably F;

t-Bu indicates a tert-butyl group; and the dashed line marks the bond which attaches the moiety to the remainder of the conjugate compound;

or a pharmaceutically acceptable salt thereof.

32. The conjugate compound in accordance with any of items 1 to 31, which is represented by formula (1A):

(1A)

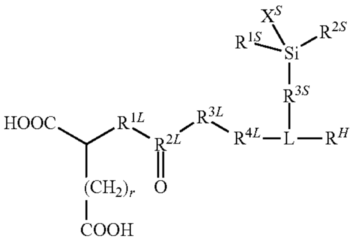

wherein the variables are defined as in the preceding items; or a pharmaceutically acceptable salt thereof.

33. The conjugate compound in accordance with item 32, which is represented by formula (1G) or (1H):

(1G)

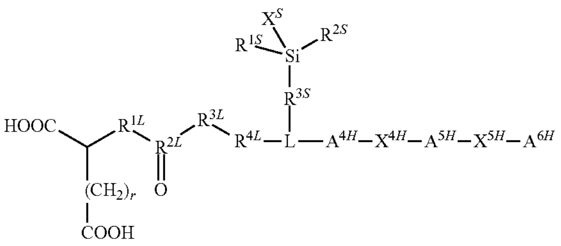

(1H)

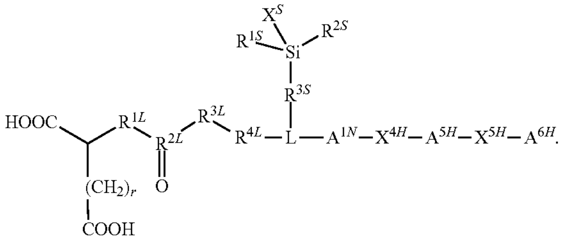

wherein the variables are defined as in the preceding items; or a pharmaceutically acceptable salt thereof.

34. The conjugate compound in accordance with item 33, which is represented by formula (11) or (1J):

(1I)

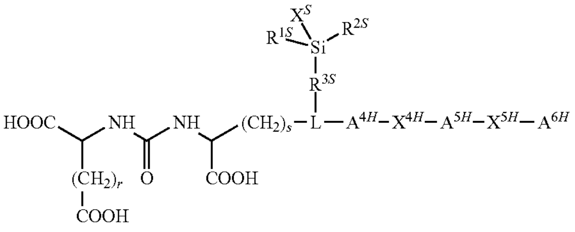

(1J)

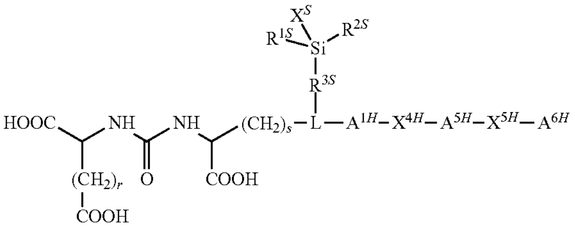

wherein the variables are defined as in the preceding items; or a pharmaceutically acceptable salt thereof.

35. The conjugate compound in accordance with any of items 1 to 34, wherein the linking moiety L has a structure represented by formula (8A) or (8B):

(8A)

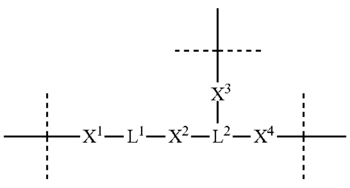

-continued (8B)

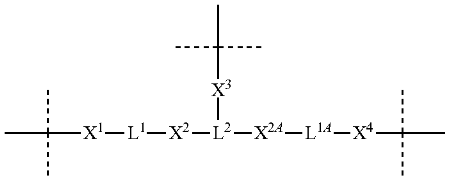

wherein the bond marked with a dashed line at $X^1$ is formed with $R^L$, the bond marked with a dashed line at $X^3$ is formed with $R^{SiFA}$, and the bond marked with a dashed line at $X^4$ is formed with $R^H$.

$X^4$ is selected from an amide bond, an ether bond, a thioether bond, an ester bond, a thioester bond, a urea bond, a thiourea bond and an amine bond, and is preferably an amide bond;

$X^2$ is selected from an amide bond, an ether bond, a thioether bond, an ester bond, a thioester bond, a urea bond, a thiourea bond and an amine bond, and is preferably an amide bond;

$X^{2A}$ is selected from an amide bond, an ether bond, a thioether bond, an ester bond, a thioester bond, a urea bond, a thiourea bond and an amine bond, and is preferably an amide bond;

$X^3$ is selected from an amide bond, an ester bond, an ether bond, an amine bond, and a linking group of the formula:

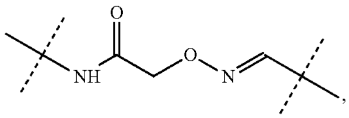

, wherein the bond marked with a dashed line at the NH group is formed with $L^2$ and the other bond marked with a dashed line is formed with $R^{SiFA}$, preferably $X^3$ is an amide bond;

$X^4$ is a group which forms, in combination with a —NH— group or —C(O)— group contained in an amino acid unit of —$R^H$, or taken in combination with a coupling unit contained in $R^H$, an amide bond, an ester bond, a thioester bond, or a urea bond; more preferably $X^4$ is —C(O)— or —NH— and forms an amide bond with a corresponding group —NH— or —C(O)— of the first amino acid unit in the sequence of amino acid units of $R^H$ which is attached via $X^4$;

$L^1$ is a divalent linking group comprising a continuous chain of 6 to 36 atoms extending from $X^1$ to $X^2$, wherein said chain is formed by carbon atoms and optional heteroatoms which are selected, independently for each occurrence if more than one heteroatom is present, from N, O and S, and wherein the chain may comprise one or more divalent cyclic or heterocyclic groups, in which case all of the ring atoms are counted as atoms of the continuous chain;

$L^{1A}$ is a divalent linking group comprising a continuous chain of 6 to 24 atoms extending from $X^{2A}$ to $X^4$, wherein said chain is formed by carbon atoms and optional heteroatoms which are selected, independently for each occurrence if more than one heteroatom is present, from N, O and S, and wherein the chain may comprise one or more divalent cyclic or heterocyclic groups, in which case all of the ring atoms are counted as atoms of the continuous chain; and $L^2$ is a trivalent moiety;

or a pharmaceutically acceptable salt thereof.

36. The conjugate compound in accordance with item 35, wherein $L^2$ is represented by formula (9):

(9)

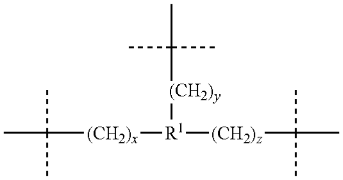

wherein $R^1$ is selected from N, $CR^2$, wherein $R^2$ is H or C1-C6 alkyl, and from a 5 to 7 membered carbocyclic or heterocyclic group; preferably $R^1$ is selected from N and CH, and more preferably $R^1$ is CH;

the bond marked by the dashed line at $(CH_2)_x$ is formed with $X^2$, and x is an integer of 0 to 4, preferably 0 or 1, and most preferably 0;

the bond marked by the dashed line at $(CH_2)_y$ is formed with $X^3$, and y is an integer of 0 to 4, preferably of 0 to 2, and more preferably 0 or 1; and the bond marked by the dashed line at $(CH_2)_z$ is formed with $X^4$ or $X^{2A}$, respectively, and z is an integer of 0 to 4, preferably of 0 to 2, and more preferably 0 or 1;

or a pharmaceutically acceptable salt thereof.

37. The conjugate compound in accordance with any of item 35 or 36, wherein $X^1$ is an amide bond;

or a pharmaceutically acceptable salt thereof.

38. The conjugate compound in accordance with any of items 35 to 37, wherein $X^2$ is an amide bond; $X^{2A}$ is an amide bond; $X^3$ is an amide bond; and $X^4$ is —C(O)— or —NH— and forms an amide bond with a corresponding group —NH— or —C(O)— of the first amino acid unit in the sequence of amino acid units of $R^H$ which is attached via $X^4$;

or a pharmaceutically acceptable salt thereof.

39. The conjugate compound in accordance with item 38, wherein the trivalent moiety $L^2$ and functional groups required for forming the amide bond $X^2$ and the amide bond $X^3$, and for forming an amide bond with a corresponding group —NH— or —C(O)— of the first amino acid unit in the sequence of amino acid units of $R^H$ or the amide bond $X^{2A}$ is provided by an amino acid selected from Dap, Dab, Orn, Lys, Asp, Glu and Hgl; and wherein the amino acid is preferably in D-configuration;

or a pharmaceutically acceptable salt thereof.

40. The conjugate compound in accordance with any of items 1 to 39, wherein the linking moiety L has a structure represented by formula (10A) or (10B):

(10A)

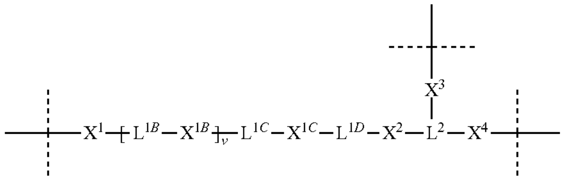

(10B)

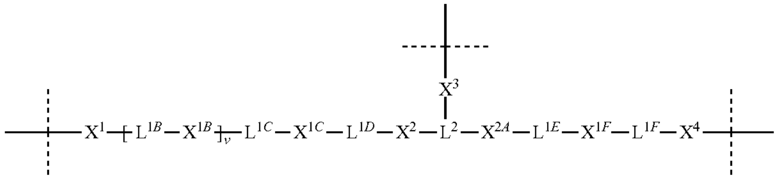

wherein:

$X^1$, $X^2$, $X^{2A}$, $X^3$, $X^4$ and $L^2$ are as defined in any of items 35 to 39;

v is 0 or 1;

$L^{1B}$ is an optionally substituted C1-C8 alkanediyl group, preferably a linear alkanediyl group, which may be interrupted by an ether bond and wherein, if the alkanediyl group comprises a chain of 4 or more carbon atoms, 4 consecutive carbon atoms in the chain may be replaced by a benzenediyl group or a cyclohexanediyl group;

$L^{1C}$ and $L^{1F}$ are independently an optionally substituted C1-C8 alkanediyl group, preferably a linear alkanediyl group, which may be interrupted by an ether bond and wherein, if the alkanediyl group comprises a chain of 4 or more carbon atoms, 4 consecutive carbon atoms in the chain may be replaced by a benzenediyl group or a cyclohexanediyl group;

$L^{1D}$ and $L^{1E}$ are independently an optionally substituted C1-C8 alkanediyl group, preferably a linear alkanediyl group, which may be interrupted by an ether bond and wherein, if the alkanediyl group comprises a chain of 4 or more carbon atoms, 4 consecutive carbon atoms in the chain may be replaced by a benzenediyl group or a cyclohexanediyl group;

$X^{1B}$ is selected from an amide bond, an ether bond, a thioether bond, an ester bond, a thioester bond, a urea bond, a thiourea bond and an amine bond, and is preferably an amide bond; and $X^{1C}$ and $X^{1F}$ are independently selected from an amide bond, an ether bond, a thioether bond, an ester bond, a thioester bond, a urea bond, a thiourea bond and an amine bond, and are preferably an amide bond;

or a pharmaceutically acceptable salt thereof.

41. The conjugate compound in accordance with item 40, wherein the optional substituent(s) of $L^{1B}$, $L^{1C}$, $L^{1D}$, $L^{1E}$ and $L^{1F}$ is (are) independently selected from —OH, —$OCH_3$, —COOH, —$COOCH_3$, —$NH_2$, —NHR, —$NHC(NH)NH_2$, phenyl, pyridinyl, naphthyl, —$CH_2$-phenyl, —$CH_2$-pyridinyl and —$CH_2$-naphtyl, wherein the group R in the substituent —NHR is an acyl group, and wherein any phenyl group may be further substituted by one or more substituents selected from halogen, preferably —F or —I, and —OH;

or a pharmaceutically acceptable salt thereof.

42. The conjugate compound in accordance with item 41, wherein the optional substituent(s) of $L^{1B}$ is (are) independently selected from —COOH, —$NH_2$, —$CH_2$-phenyl, —$CH_2$-pridinyl and —$CH_2$-naphtyl, wherein any phenyl group may be further substituted by one or more substituents selected from halogen, preferably —F or —I, and —OH; and wherein the optional substituent(s) of $L^{1C}$, $L^{1D}$, $L^{1E}$ and $L^{1F}$ is (are) independently selected from —COOH, —NHR and —$NH_2$ wherein the group R is an acyl group;

or a pharmaceutically acceptable salt thereof.

43. The conjugate compound in accordance with any of items 40 to 43, wherein $X^{1B}$ is selected from an amide bond and a urea bond, and is preferably an amide bond; and $X^{1C}$ and $X^{1F}$ are independently selected from an amide bond and a urea bond, and are preferably an amide bond;

or a pharmaceutically acceptable salt thereof.

44. The conjugate compound in accordance with item 40, wherein v is 1 and —$X^1$-$L^{1B}$-$X^{1B}$-$L^{1C}$-$X^{1C}$-$L^{1D}$-$X^2$— is represented by the divalent group of formula (11A) or (11B)

$$*—C(O)—NH—R^3—NH—C(O)—R^4—C(O)—NH—R^5—NH—C(O)— \quad (11A)$$

$$*—C(O)—NH—R^6—NH—C(O)—R^7—NH—C(O)—R^8—NH—C(O)— \quad (11B)$$

wherein $R^3$ to $R^8$ are independently selected from C2 to C8 alkanediyl, preferably linear C2 to C8 alkanediyl, which alkanediyl groups may each be substituted by one or more substitutents independently selected from —OH, —$OCH_3$, —COOH, —$COOCH_3$, —$NH_2$, —NHR and —$NHC(NH)NH_2$, wherein R is an acyl group as defined above, and wherein * marks the $X^1$ terminal of the group;

or a pharmaceutically acceptable salt thereof.

45. The conjugate compound in accordance with item 40 or 44, wherein —$X^{2A}$-$L^{1E}$-$X^{1F}$-$L^{1F}$-$X^4$— may be represented by the divalent group of formula (11C), (11D) or (11E):

$$—C(O)—NH—R^9—NH—C(O)—R^{10}—C(O)—NH—* \quad (11C)$$

$$—C(O)—NH—R^{11}—C(O)—NH—R^{12}—C(O)—NH—* \quad (11D)$$

—NH—C(O)—$R^{13}$—NH—C(O)—$R^{14}$—NH—C(O)—* (11E)

wherein $R^9$ to $R^{14}$ are independently selected from C1 to C8 alkanediyl, preferably linear C1 to C8 alkanediyl, which alkanediyl groups may each be substituted by one or more substitutents independently selected from —OH, —$OCH_3$, —COOH, —$COOCH_3$, —$NH_2$, —NHR and —NHC(NH)$NH_2$, wherein R is an acyl group;

and wherein * marks the $X^4$ terminal of the group.

46. The conjugate compound or salt in accordance with item 44 or 45, wherein v is 1 and —$X^1$-$L^{1B}$-$X^{1B}$-$L^{1C}$-$X^{1C}$-$L^{1D}$-$X^2$— is represented by the divalent group of formula (12A) or (12B):

*—C(O)—NH—CH(COOH)—$R^{15}$—NH—C(O)—$R^{16}$—C(O)—NH—$R^{17}$—CH(COOH)—NH—C(O)— (12A)

*—C(O)—NH—CH(OOH)—$R^{18}$—NH—C(O)—$R^{19}$—NH—C(O)—$R^{20}$—CH(COOH)—NH—C(O)— (12B)

wherein $R^{15}$ to $R^{20}$ are independently selected from C2 to C8 alkanediyl, preferably linear C2 to C8 alkanediyl, and $R^{16}$ or $R^{19}$ is optionally substituted by —NHR, wherein R is an acyl group as defined above, and wherein * marks the $X^1$ terminal of the group;

or a pharmaceutically acceptable salt thereof.

47. The conjugate compound in accordance with any of items 44 to 46, wherein —$X^{2A}$-$L^{1E}$-$X^{1F}$-$L^{1F}$-$X^4$— is represented by the divalent group of formula (12C), (12D) or (12E):

—C(O)—NH—CH(COOH)—$R^{21}$—NH—C(O)—$R^{22}$—C(O)—NH—* (12C)

—C(O)—NH—CH(COOH)—$R^{23}$—C(O)—NH—$R^{24}$—C(O)—NH—* (12D)

—NH—C(O)—$R^{25}$—NH—C(O)—$R^{26}$—NH—C(O)—* (12E)

wherein $R^{21}$ to $R^{22}$ are independently selected from C1 to C8 alkanediyl, preferably linear C1 to C8 alkanediyl, and $R^{22}$ or $R^{24}$ is optionally substituted by —NHR, wherein R is an acyl group, $R^{25}$ and $R^{26}$ are independently selected from C1 to C3 alkanediyl, preferably linear C1 to C3 alkanediyl, and wherein * marks the $X^4$ terminal of the group.

48. The conjugate compound or salt in accordance with any of items 1 to 47, which has a log $D_{7.4}$ value in the range of −1.5 to −4, more preferably −2.0 to −3.5, still more preferably −2.5 to −3.5.

49. A pharmaceutical or diagnostic composition comprising or consisting of one or more conjugate compounds or salts in accordance with any one of items 1 to 48.

50. A conjugate compound or salt in accordance with any of items 1 to 48 for use in medicine.

51. A conjugate compound or salt in accordance with any one of items 1 to 48 for use in a method of diagnosing, treating, or diagnosing and treating (a) cancer including prostate cancer; or (b) neoangiogenesis/angiogenesis.

EXAMPLES

The Examples illustrate the invention. Due to the presence of a SiFA moiety and a PSMA-binding moiety, the conjugate compounds of the present invention are also referred to as "SiFA-PSMA ligands" in the context of the examples.

1. Materials and Methods

1.1 Synthesis and Characterization of Compounds

For solid phase peptide synthesis (SPPS), 2-chlorotrityl chloride- (2-CTC) resin was purchased from Sigma-Aldrich Chemie GmbH (Steinheim, Germany) while protected amino acids were obtained from Iris Biotech GmbH (Marktredwitz, Germany), Carbolution Chemicals GmbH (St. Ingbert, Germany) or Bachem AG (Bubendorf, Switzerland). Further reagents and solvents were purchased from either Sigma-Aldrich Chemie GmbH, VWR International GmbH (Darmstadt, Germany), Alfa Aesar GmbH & Co. KG (Karlsruhe, Germany), Merck KGaA (Darmstadt, Germany) or ACROS Organics BVBA (Geel, Belgium) in the quality grade "for synthesis". Di-tert-butyldifluorosilane as starting material for the synthesis of SiFA-building blocks had been delivered by Fluorochem Ltd. (Hadfield, United Kingdom).

For analytical (anal.) thin-layer chromatography (TLC) of reaction mixtures a sample was chromatographed on a silica gel 60 $F_{254}$ plate (Merck KGaA), which was afterwards analyzed under ultraviolet (UV) light (λ=254 nm) or exposed to basic $KMnO_4$.

Manual flash column chromatography was carried out using silica gel (60 Å, 230-400 mesh particle size, 40-63 μm particle size) obtained from Sigma-Aldrich Chemie GmbH while automated flash chromatography was performed on a Biotage SP1 HPFC system equipped with a SNAP KPC18-HS column (12 g, 93 Å, 382 $m^2$/g, 12 mL/min) from Biotage AB (Uppsala, Sweden).

Anal. characterization and preparative (prep.) purification of organic compounds were performed on high-performance liquid chromatography (HPLC) systems from Shimadzu Deutschland GmbH (Neufahrn bei Freising, Germany) consisting of gradient pumps (two LC-20AD or a LC-20AT), a system controller (CBM-20A), a column oven (CTO-20A) and an UV/Vis detector (SPD-20A). LabSolutions software by Shimadzu Deutschland GmbH was used for visualization and analysis of chromatograms. Columns for anal. and prep. reversed-phase- (RP) HPLC were purchased from Macherey-Nagel GmbH & Co. KG (Düren, Germany), including a Nucleosil 100-5 C18 (column I, 125×4.6 mm, 5 μm, 1 mL/min), and from CS-Chromatographie Service GmbH (Langerwehe, Germany), including a MultoKrom 100-5 C18 (column II, 125×4.6 mm, 5 μm, 1 mL/min), a Multospher 100 RP 18-5p (column III, 125×4.6 mm, 5 μm, 1 mL/min), a MultoKrom 100-5 C18 (column IV, 250×10 mm, 5 μm, 5 mL/min), a MultoHigh 100 RP 18-5p (column V, 250×10 mm, 5 μm, 5 mL/min) and a Multospher 100 RP 18-5μ (column VI, 250×10 mm, 5 μm, 5 mL/min). Analyzed organic compounds were eluted applying different gradients of 0.1% trifluoroacetic acid (TFA) in water (v/v, solvent A) and 0.1% TFA as well as 5% water in acetonitrile (MeCN, v/v/v, solvent B) at a constant flow. Electrospray ionization (ESI) mass spectrometry (MS) analysis of organic compounds was conducted on an expression$^L$ CMS mass spectrometer (Advion Inc., Ithaca, United States).

1.2 Radiolabeling Equipment

[$^{125}$I]NaI as a basic solution (74 TBq/mmol, 3.1 GBq/mL, 40 mM NaOH) was purchased from Hartmann Analytic GmbH (Braunschweig, Germany) while aqueous (aq.) [$^{18}$F]

fluoride (approx. 0.6-2.0 GBq/mL) was provided by Klinikum rechts der Isar (Munich, Germany).

For fixation of $[^{11}F]$fluoride, a Sep-Pak Accell Plus QMA Carbonate Plus Light cartridge (46 mg sorbent/cartridge, 40 μm particle size) from Waters GmbH (Eschborn, Germany) was used. With $[^{18}F]$fluoride loaded QMA were dried by rinsing the cartridges with anhydrous (anhyd.) MeCN in the quality grade "≥99.9%, for DNA synthesis" (VWR International GmbH). The elution of dried $[^{18}F]$fluoride from the QMA was achieved using a solution of Kryptofix®222 in the quality grade "for synthesis" (Merck KGaA) and KOH in the quality "99.99%, semiconductor grade" (Sigma-Aldrich Chemie GmbH) in anhyd. MeCN ("≥99.9%, for DNA synthesis"). Partial neutralization of the $[^{18}F]$fluoride-containing eluate was carried out with a solution of oxalic acid in the quality grade "99.999%, trace metals basis" (Sigma-Aldrich Chemie GmbH) in anhyd. MeCN ("99.9%, for DNA synthesis"). The SiFA-PSMA ligands to be labeled were added as solutions in anhyd. dimethyl sulfoxide (DMSO) in the quality grade "99.9%" (Sigma-Aldrich Chemie GmbH). For solid phase extraction (SPE) of $^{18}F$-labeled SiFA-PSMA ligands, an Oasis HLB Plus Light cartridge (30 mg sorbent/cartridge, 30 μm particle size) from Waters GmbH was used. The $^{125}I$-labeled reference ligand XII was purified via SPE with a Sep-Pak C18 Plus Short cartridge (360 mg sorbent/cartridge, 55-105 μm particle size) also purchased from Waters GmbH.

Anal. characterization and prep. purification of radiolabeled compounds were performed on a Multospher 100 RP $1^{8}$-5μ (column III, 125×4.6 mm, 5 μm, 1 mL/min) in a HPLC system (Shimadzu Deutschland GmbH) consisting of gradient pumps (two LC-20AD), an autosampler (SIL-20AHT), a system controller (CBM-20A), a column oven (CTO-10ASVP), an UV/Vis detector (SPD-20A) and a LB 500 HERM radio flow monitor with NaI detector (Berthold Technologies GmbH & Co.KG, Bad Wildbad, Germany). LabSolutions software by Shimadzu Deutschland GmbH was again used for visualization and analysis of chromatograms. For the elution of radiolabeled compounds, the same solvents as previously introduced (solvent A and solvent B) were applied at different gradients and at a constant flow. Activity quantification was performed using a 2480 WIZARD$^{2}$ automatic gamma counter (PerkinElmer Inc., Waltham, United States).

1.3 Cell Culture and Animals

PSMA-expressing LNCaP cells (human prostate carcinoma cell line) were purchased from the Leibniz-Institute German Collection of Microorganisms and Cell Cultures (Braunschweig, Germany).

1.4 Radiolabeling

1.4.1 $^{18}F$-Labeling of SiFA-Bearing Compounds $^{18}F$-Labeling of SiFA-bearing compounds was performed following a previously published protocol with minor changes (C. Wangler, S. Niedermoser, J. Chin, K. Orchowski, E. Schirrmacher, K. Jurkschat, L. Iovkova-Berends, A. P. Kostikov, R. Schirrmacher, B. Wangler, nature protocols 2012, 7, 1946). Prior to $^{18}F$-labeling, a $[K^{+}@2.2.2]OH^{-}$ elution cocktail kit had been prepared by dissolving Kryptofix® 222 (51.25 mg, 136 μmol, 1.1 eq.) with 1 M KOH (125 μL, 125 μmol, 1.1 eq.) in water (1 mL) and freeze-drying the mixture. In order to obtain dry labeling conditions for radiofluorination, aq. $[^{18}F]$fluoride was loaded onto a Sep-Pak Accell Plus QMA Carbonate Plus Light cartridge, preconditioned (precon.) with water (10 mL). After drying with air (2×20 mL), the cartridge was slowly rinsed with anhyd. MeCN (10 mL) and subsequently dried with air (2×20 mL) again. The prepared $[K^{+}@2.2.2]OH^{-}$ kit was dissolved in anhyd. MeCN (750 μL) and a part of this cocktail (500 μL) was used to elute dried $[^{18}F]$fluoride from the cartridge. Afterwards, the eluate was partially neutralized by the addition of 1 M oxalic acid in anhyd. MeCN (30 μL, 30 μmol). The whole mixture or aliquots hereof were incubated with the SiFA-bearing compound in anhyd. DMSO (1 mM, 20-30 μL, 20-30 nmol) for 5 min at room temperature (rt). The reaction mixture was further diluted with phosphate-buffered saline (PBS, pH=3 with aq. HCl, 10 mL) and passed through an Oasis HLB Plus Light cartridge, precon. with absolute (abs.) ethanol (EtOH, 10 mL) and water (10 mL). Finally, the cartridge was rinsed with water (10 mL) or PBS (10 mL), dried with air (20 mL) and the radiofluorinated compound was eluted with a mixture of abs. EtOH/water (1:1, v/v, 200-350 μL). Radiochemical purity of the $^{18}F$-labeled SiFA-bearing compound was determined by radio-RP-HPLC and/or radio-TLC.

1.4.2 $^{125}I$-Labeling of the Reference Compound Precursor X

XII

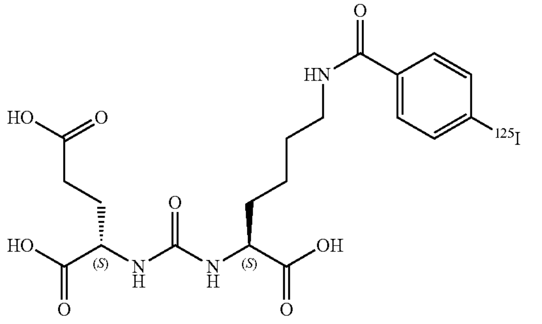

Chemical Formula: $C_{19}H_{24}{}^{125}IN_3O_8$
Molecular Weight: 547.32 g/mol

For in vitro studies, the radioiodinated reference ligand $[^{125}I]$L-Glu-u-L-Lys(p-I-BA) (XII) was generated according to a previously published protocol (M. Weineisen, J. Simecek, M. Schottelius, M. Schwaiger, H.-J. Wester, EJNMMI research 2014, 4, 63). Initial preparation of peracetic acid was achieved by mixing 30% $H_2O_2$(130 μL) with acetic acid (50 μL) and incubating the mixture for 2 h at rt. Afterwards, the reference compound precursor X (approx. 0.1 mg) was dissolved in a solution of peracetic acid (20 μL), acetic acid (10 μL), MeCN (20 μL) and basic $[^{125}I]$NaI (5 μL, 40 mM NaOH, 13.8 MBq, 74 TBq/mmol). The reaction mixture was incubated for 15 min at rt and subsequently loaded onto a Sep-Pak C18 Plus Short cartridge, precon. with methanol (MeOH, 10 mL) and water (10 mL). After rinsing the cartridge with water (10 mL) and air (2×20 mL), the radioiodinated product was eluted with a mixture of abs. EtOH/MeCN (1:1, v/v, 1.5 mL) and evaporated to dryness under a gentle stream of nitrogen. The residue was redissolved in TFA (400 μL) and incubated for 30 min at rt. Finally, the solvent was evaporated to dryness, the residue dissolved in MeCN/water (1:5, v/v, 400 μL) and purified via radio-RP-HPLC affording a solution of the radioiodinated reference ligand XII (3.85 MBq). After activity determination of a defined volume, a 2 nM solution of the reference compound XII was prepared by dilution with Hanks' Balanced Salt Solution (HBSS, add. 1% bovine serum albumin (BSA), v/v).

prep. radio-RP-HPLC (column Ill, 20-40% B in A, 20 min): $t_R$=12.1 min.

1.5 In Vitro-Evaluation

1.5.1 $IC_{50}$-Determination

LNCaP cells were grown in Dulbecco's Modified Eagle Medium/Nutrient Mixture F-12 (DMEM/F-12, add. 10% fetal calf serum (FCS), v/v) and maintained at 37° C. in a humidified 5% $CO_2$ atmosphere. For determination of the PSMA binding affinity ($IC_{50}$), cells were harvested 24±2 h before the experiment and seeded in 24-well plates (1.5×$10^5$ cells in 1 mL/well). After removal of the culture medium, LNCaP cells were treated with HBSS (add. 1% BSA, v/v, 4° C., 500 μL) and subsequently left 15 min on ice for equilibration in HBSS (add. 1% BSA, v/v, 4° C., 200 μL). Afterwards, the SiFA-PSMA ligand solution in HBSS at the appropriate concentration ($10^{-4}$-$10^{-10}$ M, 25 μL) as well as a 2 nM solution of the radioiodinated reference compound XII in HBSS (add. 1% BSA, v/v, 25 μL) were added, giving $10^{-5}$-$10^{-11}$ M solutions of the SiFA-PSMA inhibitor in the well supernatants. For the control series, HBSS (add. 1% BSA, v/v, 25 μL) was used instead of the SiFA-PSMA ligand solution. Each concentration and the control were prepared in triplicate. After 1 h incubation on ice, the assay medium was removed and cells were washed with HBSS (200 μL, 4° C.). The wash fraction was combined with the supernatant, representing the unbound fraction of competitor XII. Subsequently, LNCaP cells were treated with 1 M aq. NaOH (200 μL) for at least 10 min and the resulting cell lysate was removed. The wells were treated again with 1 M aq. NaOH (200 μL) and the wash fraction was combined with the previous lysate, affording the PSMA-bound fraction of radioligand XII. Finally, both the supernatant and the lysate were measured for activity in a gamma counter. The experiment was repeated for at least three times and the $IC_{50}$ value calculated using the GraphPad PRISM 8.0.2 software (Graphpad Software Inc., La Jolla, United States).

1.5.2 Internalization

LNCaP cells were grown in DMEM/F-12 (add. 10% FCS, v/v) and maintained at 37° C. in a humidified 5% $CO_2$ atmosphere. For internalization studies, LNCaP cells were harvested 24±2 hours before the experiment and seeded in 24-well plates (1.25×$10^5$ cells in 1 mL/well). Subsequent to the removal of the culture medium, cells were washed with DMEM-F12 (add. 5% BSA, v/v, 500 μL) and left to equilibrate in DMEM-F12 (add. 5% BSA, v/v, 200 μL) at 37° C. for 15 min. Each well was treated with either DMEM-F12 (add. 5% BSA, v/v, 25 μL) or a 2-(phosphonomethyl)-pentandioic acid (PMPA) solution (100 μM in PBS, 25 μL) for blockade. Afterwards, the $^{18}$F-labeled SiFA-PSMA ligand (5 nM in PBS, 25 μL) was added and the cells were incubated for 1 h at 37° C. The experiment was terminated by placing the 24-well plate on ice for 3 min and removal of the assay medium. Each well was rinsed with HBSS (4° C., 250 μL) and the fractions were combined with the previous assay medium, representing the amount of unbound radioligand. For removal of surface bound activity, LNCaP cells were incubated with PMPA solution (10 μM in PBS, 4° C., 250 μL) for 5 min and rinsed again with PBS (250 μL, 4° C.). The internalized activity was determined by incubation of LNCaP cells with 1 M aq. NaOH (250 μL) for at least 10 min and combination with the fraction of a subsequent wash step with 1 M aq. NaOH (200 μL). Each experiment (control and blockade) was performed in triplicate. Finally, the supernatant, the surface bound fraction and the lysate were measured for activity in a gamma counter. All internalization studies were accompanied by reference studies using the reference compound XII (2 nM in HBSS add. 1% BSA, v/v), which were performed analogously. Data were corrected for non-specific internalization and normalized to the specific-internalization observed for the radioiodinated reference compound.

1.5.3 n-Octanol-PBS Partition Coefficient

Approx. 0.5 MBq of the $^{18}$F-labeled SiFA-PSMA ligand were added into a test tube containing n-octanol (500 μL) and PBS (500 μL, pH=7.4). After vigorously shaking the two-phase mixture for 3 min at rt, the test tube was centrifuged at 9.000 rpm for 5 min to achieve quantitative phase separation. Finally, 150 μL of each layer were pipetted off and measured for activity using a gamma counter. After repeating the experiment for at least five times, the n-octanol-PBS partition coefficient log $D_{7.4}$ was calculated according to following formula.

$$\log D_{7.4} = \log\left(\frac{\text{cpm } (n\text{-octanol})}{\text{cpm } (PBS)}\right)$$

1.5.4 Binding to HSA

For the determination of human serum albumin (HSA) binding, a Chiralpak HSA column (50×3 mm, 5 μm, H13H-2433) was used at a constant flow rate of 0.5 mL/min. The mobile phase composed of a 50 mM $NH_4OAc$ solution in water with pH=7 (solvent C) and isopropanol (solvent D) was freshly prepared for each experiment and used only once. The reference substances (Table 1) as well as the analyzed SiFA-PSMA ligands were dissolved in a mixture of solvent C/solvent D (1:1, v/v, 0.5 mg/mL) and eluted from the HSA column (0-3 min: 100% C, 3-20 min: 20% D in C, λ=254 nm). The column was kept at rt and each run was stopped after detection of the signal to reduce the acquisition time. The nine reference substances display an HSA binding range of 13% to 99% and were injected consecutively in order to establish a sigmoidal calibration curve with the software OriginPro 2018b (FIG. 1).

TABLE 1

Reference substances used for the calibration of the Chiralpak HSA column with determined retention times $t_R$ corresponding to an exemplary conducted experiment, respective HSA binding literature values (K. Yamazaki, M. Kanaoka, *Journal of pharmaceutical sciences* 2004, 93, 1480-1494) and logarithmic K of HSA binding literature values.

| Reference | $t_R$ [min] | Log $t_R$ | Lit. HSA binding [%] | Log K HSA |
|---|---|---|---|---|
| Benzyl alcohol | 2.119 | 0.32613 | 13.15 | −0.82482 |
| Aniline | 2.533 | 0.40364 | 14.06 | −0.79123 |

TABLE 1-continued

Reference substances used for the calibration of the Chiralpak HSA column with determined retention times $t_R$ corresponding to an exemplary conducted experiment, respective HSA binding literature values (K. Yamazaki, M. Kanaoka, *Journal of pharmaceutical sciences* 2004, 93, 1480-1494) and logarithmic K of HSA binding literature values.

| Reference | $t_R$ [min] | Log $t_R$ | Lit. HSA binding [%] | Log K HSA |
|---|---|---|---|---|
| Phenol | 3.021 | 0.48015 | 20.69 | −0.58901 |
| Benzoic acid | 3.825 | 0.58263 | 34.27 | −0.28941 |
| Carbamazepine | 3.898 | 0.59084 | 75.00 | 0.46009 |
| 4-Nitrophenol | 5.043 | 0.70269 | 77.65 | 0.52185 |
| Estradiol | 6.918 | 0.83998 | 94.81 | 1.18516 |
| Probenecid | 7.474 | 0.87355 | 95.00 | 1.19957 |
| Glibenclamide | 28.624 | 1.45673 | 99.00 | 1.69461 |

FIG. 1 shows an exemplary sigmoidal plot of the reference substance logarithmic K of HSA binding literature value versus respective logarithm of the retention time on the Chiralpak HSA column.

1.6 In Vivo-Evaluation

All animal experiments were conducted in accordance with general animal welfare regulations in Germany and the institutional guidelines for the care and use of animals. To establish tumor xenografts, LNCaP cells (approx. 107) were resuspended in a mixture of DMEM-F12/Matrigel (200 μL, 1:1, v/v) and inoculated subcutaneously on the right shoulder of 6-8 weeks old CB-17 SCID male mice. Animals were used for experiments when the tumor volume reached 4-7 mm in diameter (approx. 3-4 weeks after inoculation).

1.6.1 Biodistribution Studies

For biodistribution studies, isoflurane-anesthetized LNCaP tumor-bearing CB-17 SCID male mice were injected via the tail vein with approx. 1-4 MBq (0.2 nmol) of the $^{18}$F-labeled SiFA-PSMA ligand and sacrificed 1 h p.i. (n=4-5). Selected organs, tissues and body fluids (blood, heart, lung, liver, spleen, pancreas, stomach without contents, intestine with contents, kidney, adrenal gland, muscle, bone, tumor, salivary gland and tail) were removed, weighted and measured for activity using a gamma counter.

1.6.2 Small-Animal μPET/CT Imaging

For μPET/CT imaging studies, LNCaP tumor-bearing CB-17 SCID male mice under isoflurane anesthesia were injected via the tail vein with approx. 6 MBq (0.2 nmol) of the $^{18}$F-labeled SiFA-PSMA ligand. Static images were recorded 1 h p.i. on a VECTor$^4$CT scanner (M/Labs B. V., Utrecht, Netherlands) with an acquisition time of 15 min and reconstructed using the software PMOD 4.0 (PMOD Technologies LLC, Zurich, Switzerland).

2. Synthesis Protocols

2.1 Synthesis of SiFA-Building Blocks

The synthesis of SiFA-building blocks was carried out according to a previously published protocol with minor modifications (Scheme 1). The final reaction affording compound IV was achieved by direct oxidation of the respective alcohol Ill. Reported spectroscopic data are in accordance with the literature (L. Iovkova, B. Wangler, E. Schirrmacher, R. Schirrmacher, G. Quandt, G. Boening, M. Schürmann, K. Jurkschat, Chemistry-A European Journal 2009, 15, 2140-2147; D. P. Smith, J. Anderson, J. Plante, A. E. Ashcroft, S. E. Radford, A. J. Wilson, M. J. Parker, Chemical Communications 2008, 5728-5730).

Scheme 1. Synthesis of 4-(di-tert-butylfluorosilyl)benzoic acid (IV)

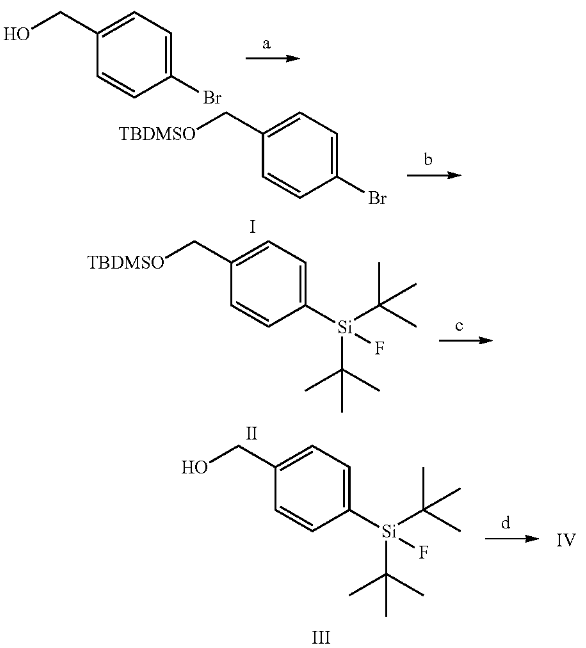

a) imidazole, tert-butyldimethylsilyl chloride, (DCM); b) 1.7M tBuLi in pentane, di-tert-butyldifluorosilane, (THF); c) 37% aq. HCl, (MeOH); d) 1M aq. $KMnO_4$, 1.25M aq. $NaH_2PO_4$, (DCM).

2.1.1 Synthesis Example 1: ((4-Bromobenzyl)oxy)(tert-butyl)dimethylsilane (I)

I

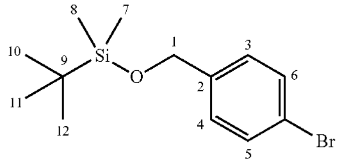

Chemical Formula: $C_{13}H_{21}BrOSi$
Molecular Weight: 301.30 g/mol

Imidazole (2.04 g, 30.0 mmol, 1.2 eq.) and tert-butyldimethylsilyl chloride (4.52 g, 30.0 mmol, 1.2 eq.) were added to a solution of 4-bromobenzylalcohol (4.68 g, 25.0 mmol, 1.0 eq.) in anhyd. dimethylformamide (DMF, 70 mL). The resulting mixture was stirred for 16 h at rt, subsequently poured into ice-cold water (250 mL) and extracted with diethyl ether ($Et_2O$, 5×50 mL). The combined organic layers were washed with sat. aq. $NaHCO_3$ (2×100 mL) and sat. aq. NaCl (100 mL), dried over $MgSO_4$, filtered, and concentrated in vacuo. The resulting crude product was purified by flash column chromatography (silica, 5% ethyl acetate (EtOAc) in petroleum ether (PE), v/v) yielding I as a colorless oil (7.27 g, 24.1 mmol, 96%).

Anal. RP-HPLC (column I, 50-100% B in A, 15 min, λ=220 nm): $t_R$=14.0 min; TLC: $R_f$ (5% EtOAc in PE, v/v)=0.87 [UV]; MS (ESI, positive): m/z calc. m.i. mass ($C_{13}H_{21}BrOSi$): 300.1, m/z found: not detectable.

$^1$H-NMR (300 MHz, $CDCl_3$): δ [ppm]=0.11 (s, 6H, C7-$H_3$, C8-$H_3$), 0.96 (s, 9H, C10-$H_3$, C11-$H_3$, C12-$H_3$), 4.77 (s, 2H, C1-$H_2$), 7.34 (d, J=7.9 Hz, 2H, C3-H, C4-H), 7.57 (d, J=8.0 Hz, 2H, C5-H, C6-H).

2.1.2 Synthesis Example 2: Di-tert-butyl(4-(((tert-butyldimethylsilyl)oxy)methyl) phenyl)-fluorosilane (II)

II

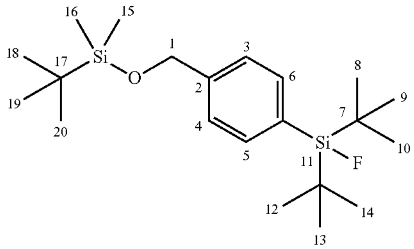

Chemical Formula: $C_{21}H_{39}FOSi_2$
Molecular Weight: 382.71 g/mol

A solution of tert-butyllithium (tBuLi) in pentane (9.37 mL, 1.7 m, 15.9 mmol, 2.4 eq.) was added to a solution of ((4-bromobenzyl)oxy)(tert-butyl)dimethylsilane (I) (2.00 g, 6.64 mmol, 1.0 eq.) in anhyd. tetrahydrofuran (THF, 20 mL) at −78° C. The resulting yellow reaction mixture was stirred for 30 min at −78° C. and afterwards added dropwise to a stirred solution of di-tert-butyldifluorosilane (1.43 g, 1.60 mL, 7.97 mmol, 1.2 eq.) in anhyd. THE (15 ml) at −78° C. Subsequently, the mixture was allowed to warm up to rt over 18 h, hydrolyzed with sat. aq. NaCl (120 mL) and extracted with $Et_2O$ (4×100 mL). The combined organic phases were dried over $MgSO_4$, filtered, and concentrated in vacuo affording II (2.77 g) as a pale-yellow oil. The product was used for the next reaction step without further purification.

Anal. RP-HPLC (column I, 80-100% B in A, 20 min, λ=220 nm): $t_R$=16.9 min; MS (ESI, positive): m/z calc. m.i. mass ($C_{21}H_{39}FOSi_2$): 382.3, m/z found: not detectable.

2.1.3 Synthesis Example 3: (4-(Di-tert-butylfluorosilyl)phenyl)methanol (III)

III

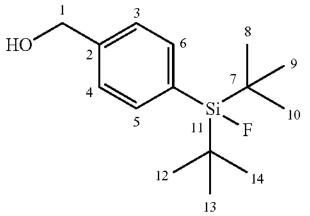

Chemical Formula: $C_{15}H_{25}FOSi$
Molecular Weight: 268.45 g/mol

A catalytic amount of 37% aq. HCl (0.8 mL) was added to a solution of di-tert-butyl(4-(((tert-butyldimethylsilyl)oxy)methyl)phenyl)fluorosilane (II) (1.88 g, 4.92 mmol, 1.0 eq.) in MeOH (75 mL). The reaction mixture was stirred for 20 h at rt and afterwards concentrated in vacuo. Subsequently, the residue was redissolved in $Et_2O$ (50 mL), washed with sat. aq. $NaHCO_3$ (50 mL) and extracted with $Et_2O$ (3×50 mL). The combined organic fractions were dried over $MgSO_4$, filtered, and concentrated in vacuo yielding III as a yellowish oil (1.96 g). The product was used for the next reaction step without further purification.

Anal. RP-HPLC (column I, 50-100% B in A, 15 min, λ=220 nm): $t_R$=9.3 min; MS (ESI, positive): m/z calc. m.i. mass ($C_{15}H_{25}FOSi$): 268.2, m/z found: not detectable.

$^1$H-NMR (300 MHz, $CDCl_3$): δ [ppm]=1.06 (d, 18H, J=1.2 Hz, C8-$H_3$, C9-$H_3$, C10-$H_3$, C12-$H_3$, C13-$H_3$, C14-$H_3$), 4.71 (s, 2H, C1-$H_2$), 7.38 (d, 2H, J=7.8 Hz C5-H, C6-H), 7.61 (d, 2H, J=8.0 Hz, C3-H, C4-H).

2.1.4 Synthesis Example 4: 4-(Di-tert-butylfluorosilyl)benzoic acid (IV)

IV

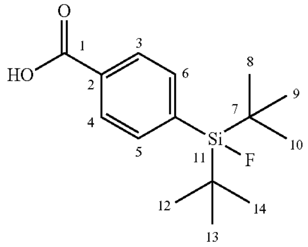

Chemical Formula: $C_{15}H_{23}FO_2Si$
Molecular Weight: 282.43 g/mol (4-(Di-tert-butylfluorosilyl)phenyl)methanol (III) (6.61 g, 24.6 mmol, 1.0 eq.) was dissolved in a mixture of 1 M aq. $KMnO_4$ (37 mL, 36.7 mmol, 1.5 eq.), tert-butyl alcohol (tBuOH, 65 mL), dichlormethane (DCM, 9 mL), and 1.25 M aq. $NaH_2PO_4$ (65 mL, 81.5 mmol, 3.3 eq.). After stirring the reaction mixture for 45 min at rt and cooling it afterwards to 0° C., an excess of $KMnO_4$ (7.78 g, 49.2 mmol, 2.0 eq.) was added and the mixture stirred for another 2 h at 0° C. The reaction was subsequently quenched by the addition of sat. aq. $Na_2SO_3$ (150 mL). Precipitated $MnO_2$ was dissolved with 37% aq. HCl (20 mL) and the resulting solution extracted with $Et_2O$ (3×300 mL). The combined organic fractions were washed with sat. aq. $NaHCO_3$ (300 mL), dried over $MgSO_4$, filtered, and concentrated in vacuo yielding a white solid that was purified by recrystallization from $Et_2O$/n-hexane (1:3, v/v) to afford IV (2.57 g, 9.10 mmol, 37%).

Anal. RP-HPLC (column I, 50-100% B in A, 15 min, λ=220 nm): $t_R$=8.5 min; MS (ESI, positive): m/z calc. m.i. mass ($C_{15}H_{23}FO_2Si$): 282.2, m/z found: not detectable.

2.2 Synthesis of the PSMA-Binding Motif

The PSMA-binding motif tBuO-L-Glu(OtBu)-u-L-Glu-OtBu (VII) was obtained following the synthesis protocol of an analogous compound previously published (Scheme 2) (M. Weineisen, J. Simecek, M. Schottelius, M. Schwaiger, H.-J. Wester, EJNMMI research 2014, 4, 63).

Scheme 2. Synthesis of tBuO-L-Glu(OtBu)-u-L-Glu-OtBu (VII)

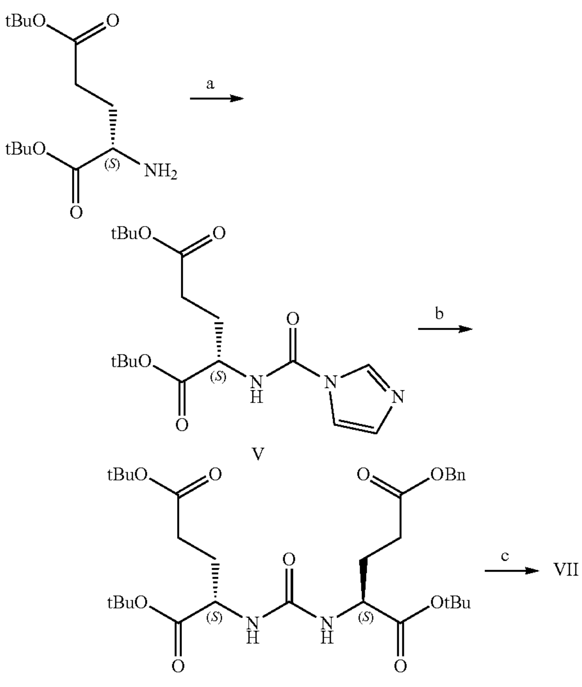

a) CDI, DMAP, TEA, (DCM);
b) H-L-Glu(OBn)-OtBu•HCl, TEA, (DCE);
c) 10% Pd/C, (EtOH).

2.2.1 Synthesis Example 5: (S)-di-tert-butyl 2-(1H-imidazole-1-carboxamido)pentanedioate (V)

V

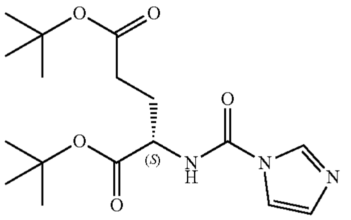

Chemical Formula: $C_{17}H_{27}N_3O_5$
Molecular Weight: 353.42 g/mol

Under argon atmosphere, triethylamine (TEA, 3.90 mL, 28.0 mmol, 2.5 eq.) was added dropwise at rt to a solution of H-L-Glu(OtBu)-OtBu-HCl (2.91 g, 11.2 mmol, 1.0 eq.) and 4-dimethylaminopyridine (DMAP, 54.7 mg, 0.450 mmol, 0.04 eq.) in anhyd. DCM (25 mL) forming a white precipitate. The suspension was cooled to 0° C. and added dropwise to an ice-cold solution of 1,1'-carbonyldiimidazole (CDI, 2.00 g, 12.3 mmol, 1.1 eq.) in anhyd. DCM (25 mL). After stirring the resulting colorless solution overnight at rt, DCM (25 mL) was added and the organic phase was extracted with sat. $NaHCO_3$ (30 mL), water (2×30 mL) and sat. NaCl (30 mL). The organic fraction was finally concentrated in vacuo affording V (4.05 g) in form of a yellowish gel. The product was used for the next reaction step without further purification.

Anal. RP-HPLC (column I, 10-90% B in A, 15 min, λ=220 nm): $t_R$=14.5 min; MS (ESI, positive): m/z calc. m.i. mass ($C_{17}H_{27}N_3O_5$): 353.2, m/z found: 376.3 [M+Na]+.

2.2.2 Synthesis Example 6: tBuO-L-Glu(OtBu)-u-L-Glu(OBn)-OtBu (VI)

VI

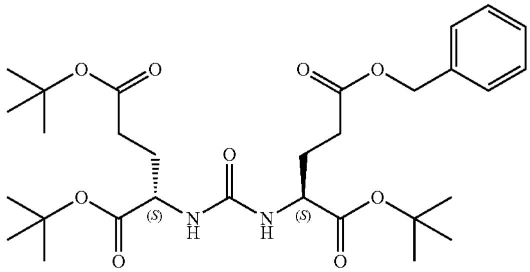

Chemical Formula: $C_{30}H_{46}N_2O_9$
Molecular Weight: 578.70 g/mol

A solution of (S)-di-tert-butyl 2-(1H-imidazole-1-carboxamido)pentanedioate (V) (2.73 g, 7.73 mmol, 1.0 eq.) and H-L-Glu(OBn)-OtBu-HCl (2.55 g, 7.73 mmol, 1.0 eq.) in 1,2-dichloroethane (DCE, 25 mL) was cooled to 0° C. and afterwards treated dropwise with TEA (2.16 mL, 15.5 mmol, 2.0 eq.). The reaction mixture was initially stirred at 0° C. for 1 h, then for 5 h at rt and finally stirred overnight at 40° C. After concentrating the mixture in vacuo, the residue was redissolved in MeOH (5 mL) and purified by flash column chromatography (silica, 40-+50% EtOAc in n-hexane, v/v) yielding VI (3.89 g, 6.72 mmol, 87%) as a yellowish viscous oil.

Anal. RP-HPLC (column I, 10-90% B in A, 15 min, λ=220 nm): $t_R$=17.4 min; MS (ESI, positive): m/z calc. m.i. mass ($C_{30}H_{46}N_2O_9$): 578.3, m/z found: 411.3 $[M-3tBu+H]^+$, 467.3 $[M-2tBu+H]^+$, 523.3 $[M-tBu+H]^+$, 601.5 $[M+Na]^+$.

2.2.3 Synthesis Example 7: tBuO-L-Glu(OtBu)-u-L-Glu-OtBu (VII)

VII

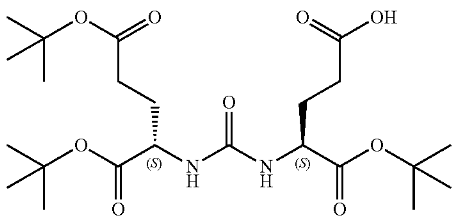

Chemical Formula: $C_{23}H_{40}N_2O_9$
Molecular Weight: 488.57 g/mol

For benzyl- (Bn) deprotection, tBuO-L-Glu(OtBu)-u-L-Glu(OBn)-OtBu (VI) (3.89 g, 6.73 mmol, 1.0 eq.) was dissolved in abs. EtOH (35 mL) and treated with 10% palladium on carbon (390 mg, 0.673 mmol, 0.1 eq., w/w). The reaction mixture was stirred overnight at rt under hydrogen atmosphere, filtered through Celite® and concentrated in vacuo giving VII (3.00 g, 6.14 mmol, 91%) as a colorless hygroscopic solid.

Anal. RP-HPLC (column I, 10-90% B in A, 15 min, λ=220 nm): $t_R$=11.3 min; MS (ESI, positive): m/z calc. m.i. mass ($C_{23}H_{40}N_2O_9$): 488.3, m/z found: 321.2 [M-3tBu+H]$^+$, 489.1 [M+H]$^+$, 511.4 [M+Na]$^+$.

2.3 Synthesis Example 8: Synthesis of the Reference Compound Precursor X

The reference compound precursor tBuO-L-Glu(OtBu)-u-L-Lys(p-$SnBu_3$-BA)-OtBu (X) was synthesized over three reaction steps following a previously published procedure (Scheme 3) (M. Weineisen, J. Simecek, M. Schottelius, M. Schwaiger, H.-J. Wester, EJNMMI research 2014, 4, 63).

Scheme 3. Synthesis of the reference compound precursor X

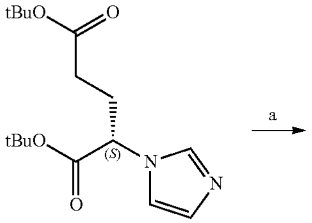

V

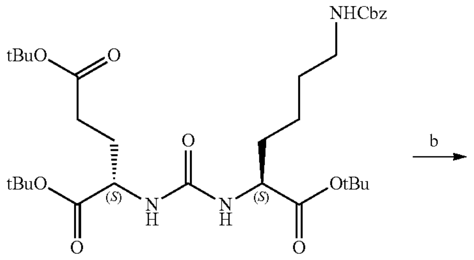

VIII

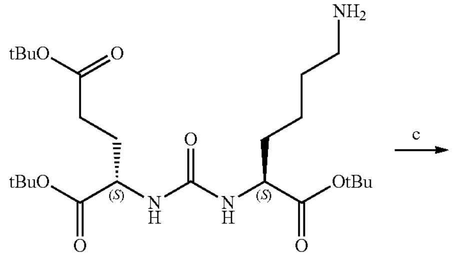

X

IX a) H-L-Lys(Cbz)-OtBu•HCl, TEA, (DCE); b) 10% Pd/C, (EtOH); c) N-succinimidyl 4-(tri-n-butylstannyl)benzoate, TEA, (DCM).

tBuO-L-Glu(OtBu)-u-L-Lys(Cbz)-OtBu (VIII)

VIII

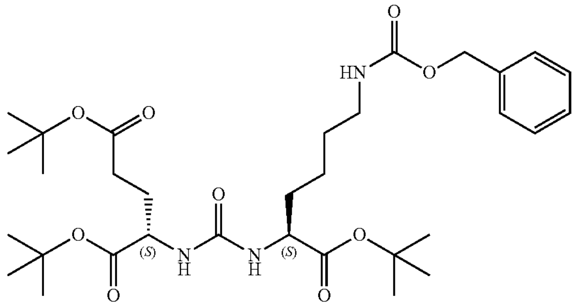

Chemical Formula: $C_{32}H_{51}N_3O_9$
Molecular Weight: 621.77 g/mol

A solution of (S)-di-tert-butyl 2-(1H-imidazole-1-carboxamido)pentanedioate (V) (3.57 g, 10.1 mmol, 1.0 eq.) in DCE (45 mL) was cooled to 0° C. and TEA (2.82 mL, 20.2 mmol, 2.0 eq.) as well as H-L-Lys(Cbz)-OtBu-HCl (4.14 g, 11.1 mmol, 1.1 eq.) were added under stirring. The reaction mixture was heated to 40° C. overnight, subsequently washed with water (45 mL) and sat. aq. NaCl (45 mL), dried over $MgSO_4$, filtered, and concentrated in vacuo. The resulting crude product was purified by flash column chromatography (silica, 40% EtOAc in n-hexane, v/v) affording VIII (5.04 g, 8.11 mmol, 80%) as a colourless oil.

TLC: $R_f$ (5% EtOAc in n-hexane, v/v)=0.45 [$KMnO_4$].

tBuO-L-Glu(OtBu)-u-L-Lys-OtBu (IX)

IX

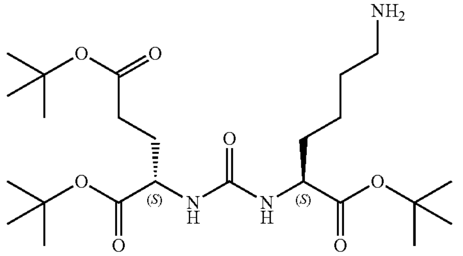

Chemical Formula: $C_{24}H_{45}N_3O_7$
Molecular Weight: 487.63 g/mol

For benzyloxycarbonyl- (Cbz) deprotection, tBuO-L-Glu(OtBu)-u-L-Lys(Cbz)-OtBu (VIII) (6.03 g, 9.71 mmol, 1.0 eq.) was dissolved in abs. EtOH (150 mL) and treated with 10% palladium on carbon (600 mg, 1.00 mmol, 0.1 eq., w/w). The reaction mixture was stirred overnight at rt under hydrogen atmosphere, filtered through Celite® and concentrated in vacuo yielding IX (4.33 g, 8.88 mmol, 91%) as a colorless waxy solid.

Anal. RP-HPLC (column I, 10-90% B in A, 15 min, λ=220 nm): $t_R$=12.6 min; MS (ESI, positive): m/z calc. m.i. mass ($C_{24}H_{45}FN_3O_7$): 487.3, m/z found: 488.3 [M+H]$^+$, 510.3 [M+Na]$^+$.

tBuO-L-Glu(OtBu)-u-L-Lys(p-$SnBu_3$-BA)-OtBu
(X)

X

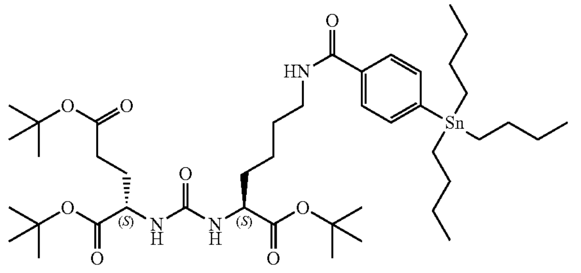

Chemical Formula: $C_{43}H_{75}N_3O_8Sn$
Molecular Weight: 880.78 g/mol tBuO-L-Glu(OtBu)-u-L-Lys-OtBu (IX) (86.4 mg, 0.177 mmol, 1.2 eq.) and N-succinimidyl 4-(tri-n-butylstannyl) benzoate (75.0 mg, 0.148 mmol, 1.0 eq.) were dissolved in DCM (1.5 mL) and TEA (92.6 μL, 0.664 mmol, 4.5 eq.) was added. The reaction mixture was stirred at rt overnight and subsequently washed with water (50 mL). Finally, the separated organic phase was concentrated in vacuo yielding the reference compound precursor X (118.6 mg) as a pale-yellow oil. The crude product was used for the $^{125}$I-labeling reaction without further purification.

MS (ESI, positive): m/z calc. m.i. mass ($C_{43}H_{75}N_3O_8Sn$): 881.5, m/z found: 882.7 $[M+H]^+$, 1764.5 $[2M+H]^+$.

2.4 Synthesis Example 9: Synthesis of tBuO-D-Glu (OtBu)-u-D-Glu-OtBu (XV)

The pharmacokinetic modifier XV was synthesized in analogy to the PSMA-binding motif tBuO-L-Glu(OtBu)-u-L-Glu-OtBu (VII) (Scheme 4).

Scheme 4. Synthesis of tBuO-D-Glu(OtBu)-u-D-Glu-OtBu (XV)

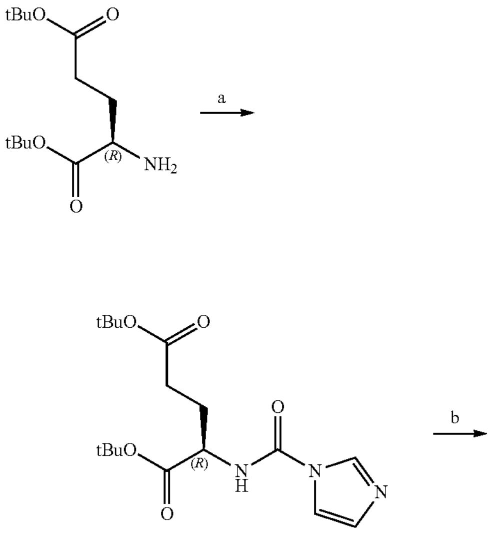

XIII

-continued

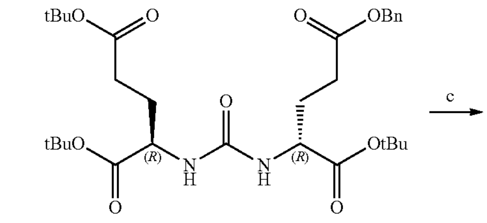

XV

XIV a) CDI, DMAP, TEA, (DCM); b) H-D-Glu(OBn)-OtBu•HCl, TEA, (DCE); c) 10% Pd/C, (EtOH).

XV

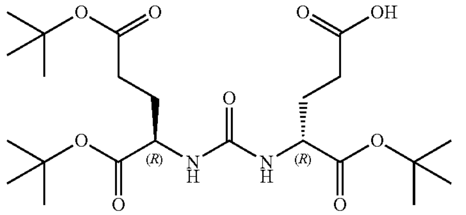

Chemical Formula: $C_{23}H_{40}N_2O_9$
Molecular Weight: 488.57 g/mol

With H-D-Glu(OtBu)-OtBu HCl as starting material, (R)-di-tert-butyl 2-(1H-imidazole-1-carboxamido)pentanedioate (XIII) (1.48 g, 4.19 mmol, 91%) was synthesized in a first reaction step, coupled with H-D-Glu(OBn)-OtBu·HCl to yield tBuO-D-Glu(OtBu)-u-D-Glu(OBn)-OtBu (XIV) (2.05 g, 3.54 mmol, 84%) in a second conversion and was finally Bn-deprotected affording the pharmacokinetic modifier XV (1.42 g, 2.91 mmol, 82%) as a colorless hygroscopic solid.

Anal. RP-HPLC (column I, 10-90% B in A, 15 min, λ=220 nm): $t_R$=12.0 min; MS (ESI, positive): m/z calc. m.i. mass ($C_{23}H_{40}N_2O_9$): 488.3, m/z found: 489.5 $[M+H]^+$.

2.5 Synthesis Example 10: Synthesis of 3,5-bis(tert-butoxycarbonyl)benzoic acid (XVI) 3,5-Bis(tert-butoxycarbonyl)benzoic acid (XVI) was synthesized by twofold tBu-protection of trimesic acid (Scheme 5).

Scheme 5. Synthesis of 3,5-bis(tert-butoxycarbonyl)benzoic acid (XVI)

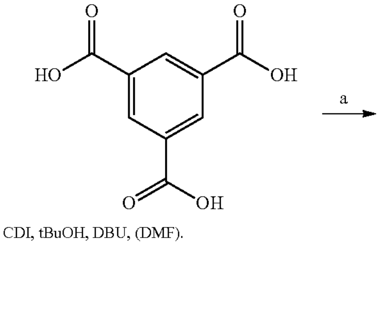

XVI a) CDI, tBuOH, DBU, (DMF).

XVI

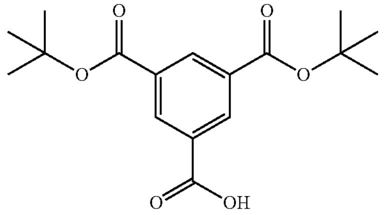

Chemical Formula: $C_{17}H_{22}O_6$
Molecular Weight: 322.36 g/mol

Trimesic acid (500 mg, 2.38 mmol, 1.0 eq.) and CDI (769 mg, 4.76 mmol, 2.0 eq.) were dissolved in DMF (10 mL) and the solution was stirred for 1 h at 40° C. Afterwards, tBuOH (667 μL, 7.14 mmol, 3.0 eq.) and 1,8-diazabicyclo(5.4.0) undec-7-ene (DBU, 707 μL, 4.76 mmol, 2.0 eq.) were added and the reaction mixture was stirred for another 24 h at 40° C. before purification via flash chromatography. 3,5-Bis (tert-butoxycarbonyl)benzoic acid (XVI) (310 mg, 0.962 mmol, 40%) was obtained as a colorless solid.

Flash chromatography (Biotage™ SNAP KPC18-HS column, 12 g, 93 Å, 382 $m^2/g$, 30-80% B in A, 20 min, λ=220 nm): $t_R$=15.5 min; MS (ESI, negative): m/z calc. m.i. mass ($C_{17}H_{22}O_6$): 322.1, m/z found: 320.9 $[M-H]^-$.

2.6 General Synthesis Procedures for SPPS

GSP1 Resin Loading

2-CTC-resin (1.0 eq., 1.60 mmol/g) was transferred into a syringe and swollen with a solution containing the solved fluorenylmethyloxycarbonyl- (Fmoc) protected amino acid or an Fmoc-protected carboxy-bearing compound (1.5 eq.) with N,N-diisopropylethylamine (DIPEA, 1.3 eq.) in DMF (10 mL/g of resin). The mixture was shaken for 5 min at rt and afterwards DIPEA (2.6 eq.) was added again. The syringe content was shaken for another 90 min at rt. Then, unreacted groups on the 2-CTC-resin were capped by adding MeOH (1 mL/g of resin) and shaking the mixture for 15 min at rt. Finally, the resin was filtered, washed successively with DMF (3×15 mL/g of resin), MeOH (3×15 mL/g of resin), DCM (3×15 mL/g of resin), and dried in vacuo. The resin loading was calculated according to following formula (Equation 1).

$$\text{loading [mol/g]} = \frac{(m_2 - m_1)}{(\text{MW} - 36.46\ \text{g/mol}) \cdot m_2}$$

Equation 1. Calculation of the resin loading.

GSP2 On-Resin Fmoc-Deprotection

Prior to a coupling reaction, the amine functionality was Fmoc-deprotected by treating the resin twice with a solution of 20% piperidine (Pip) in DMF (v/v, 15 mL/g of resin) for respectively 5 min and 15 min at rt. For compounds containing a 1-(4,4-dimethyl-2,6-dioxocyclohex-1-ylidene) ethyl- (Dde) protecting group, the treatment was performed twice for 5 min at rt. Subsequently, the resin was filtered and washed thoroughly with DMF (7×15 mL/g of resin).

GSP3 On-Resin Amide Bond Formation a) Amino Acid/Carboxy-Bearing Compound Coupling Reaction The amino acid or the carboxy-bearing compound (1.5-3.0 eq.), 1-hydroxy-7-azabenzotriazole (HOAt, 1.5-3.0 eq.) and O-(benzotriazol-1-yl)-N,N,N',N'-tetramethyluronium tetrafluoroborate (TBTU, 1.5-3.0 eq.) were dissolved in DMF (10 mL/g of resin) and sym-collidine (4.5-9.0 eq.) was added. After 10 min, the mixture was transferred into the syringe containing the swollen resin and shaken for 1.5 h at rt. Finally, the resin was filtered and washed with DMF (3×15 mL/g of resin) as well as DCM (3×15 mL/g of resin).

b) Succinic Anhydride Coupling Reaction

A solution of succinic anhydride (7.0 eq.) and DIPEA (7.0 eq.) in DMF (10 mL/g of resin) was transferred into the syringe containing the swollen resin and shaken for 12 h at rt. The resin was afterwards filtered and washed with DMF (3×15 mL/g of resin) as well as DCM (3×15 mL/g of resin).

c) SiFA-Coupling Reaction 4-(Di-tert-butylfluorosilyl)benzoic acid (IV) (2.0 eq.), HOAt (2.0 eq.) and TBTU (2.0 eq.) were dissolved in DMF (10 mL/g of resin) and sym-collidine (6.0 eq.) was added. After 10 min, the mixture was transferred into the syringe containing the swollen resin and shaken for 2 h at rt. Subsequently, the resin was filtered and washed with DMF (3×15 mL/g of resin) as well as DCM (3×15 mL/g of resin).

GSP4 On-Resin Dde-Deprotection (a) Dde-Deprotection in Absence of an Fmoc-Protecting Group In absence of an Fmoc-protecting group, Dde-deprotection was carried out by treating the resin with a solution of 2% hydrazine monohydrate in DMF (v/v, 15 mL/g of resin) for 20 min at rt. Finally, the resin was filtered and washed thoroughly with DMF (7×15 mL/g of resin) as well as DCM (3×15 mL/g of resin).

(b) Selective Dde-Deprotection in Presence of an Fmoc-Protecting Group

In presence of an Fmoc-protecting group, Dde-deprotection was performed by treating the resin twice with a solution of imidazole (90 eq.) and hydroxylamine hydrochloride (120 eq.) in a mixture of N-methyl-2-pyrrolidone (NMP) and DMF (5:1, v/v, 15 mL/g of resin) for 1.5 h at rt. The resin was finally filtered and washed thoroughly with DMF (3×15 mL/g of resin) as well as DCM (3×15 mL/g of resin).

GSP5 Cleavage from the Resin and Final Deprotection

The resin-bound compound with acid-labile protecting groups was treated twice with a solution of TFA/triisopropylsilane (TIPS)/water (95:2.5:2.5, v/v/v, 10 mL/g of resin) for 1 h at rt and subsequently washed with the cleavage cocktail (10 mL/g of resin). Then, the combined acidic fractions were concentrated using a stream of nitrogen. The resulting residue was taken up in aq. tBuOH, freeze-dried and, if required, prepared for prep. RP-HPLC purification by dissolution in an appropriate solvent.

2.7 Synthesis Example 11: Synthesis of SiFA-D-Asp(OH)—OH (XVII)

SiFA-D-Asp(OH)—OH (XVII) was obtained via SPPS (Scheme 6).

Scheme 6. Synthesis of SiFA-D-Asp(OH)-OH (XVII)

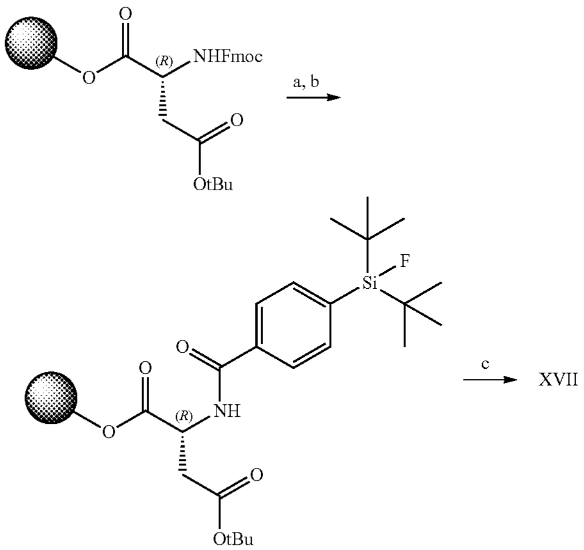

a) 20% Pip in DMF; b) 4-(di-tert-butylfluorosilyl)benzoic acid (IV), HOAt, TBTU, sym-collidine, (DMF); c) 95% TFA/2.5% TIPS/2.5% water.

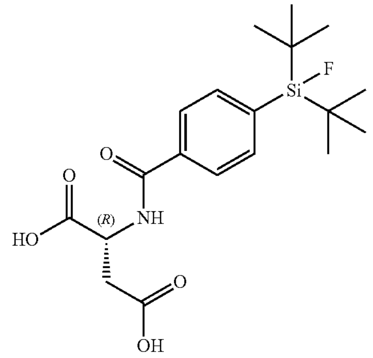

Chemical Formula: $C_{19}H_{28}FNO_5Si$
Molecular Weight: 397.52 g/mol

2-CTC-resin was loaded with Fmoc-D-Asp(OtBu)-OH (GSP1). The amino acid was subsequently Fmoc-deprotected (GSP2) and coupled with 4-(di-tert-butylfluorosilyl) benzoic acid (IV) (GSP3c). The compound was finally cleaved from the resin under removal of the tBu-protecting group (GSP5) giving crude SiFA-D-Asp(OH)—OH (XVII) (126 mg, 0.316 mmol, quant.) as a colorless oil.

Anal. RP-HPLC (column II, 10-90% B in A, 15 min, λ=220 nm): $t_R$=13.0 min; MS (ESI, positive): m/z calc. m.i. mass ($C_{19}H_{28}FNO_5Si$): 397.2, m/z found: 398.2 $[M+H]^+$.

2.8 Synthesis of Novel SiFA-PSMA Ligands

2.8.1 Synthesis Example 12: Resin-Bound SiFA-PSMA Ligand Precursor XI

Scheme 7. Synthesis of the resin-bound SiFA-PSMA ligand precursor XI

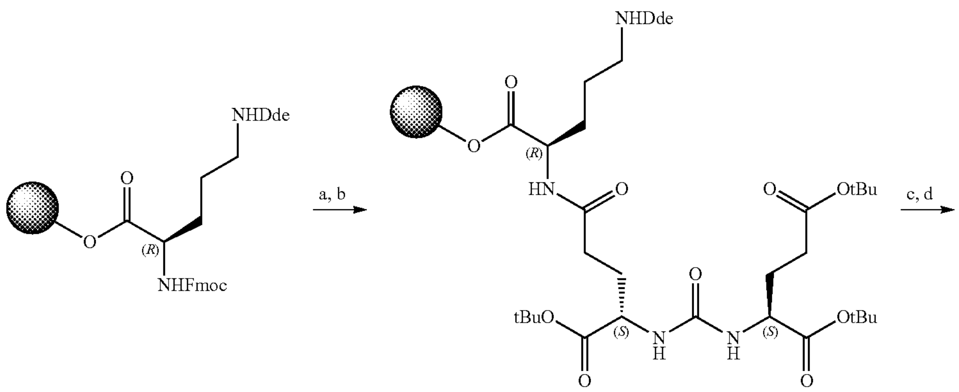

-continued
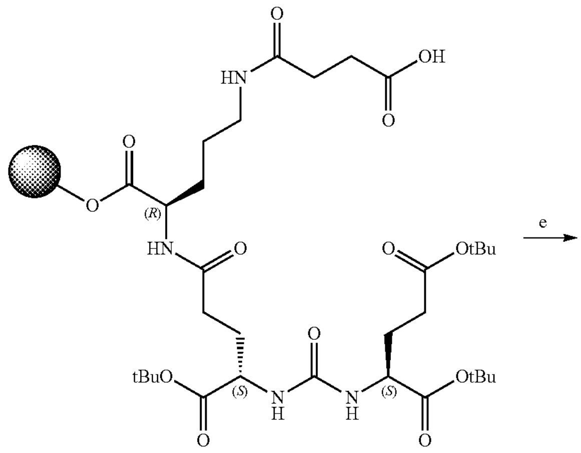
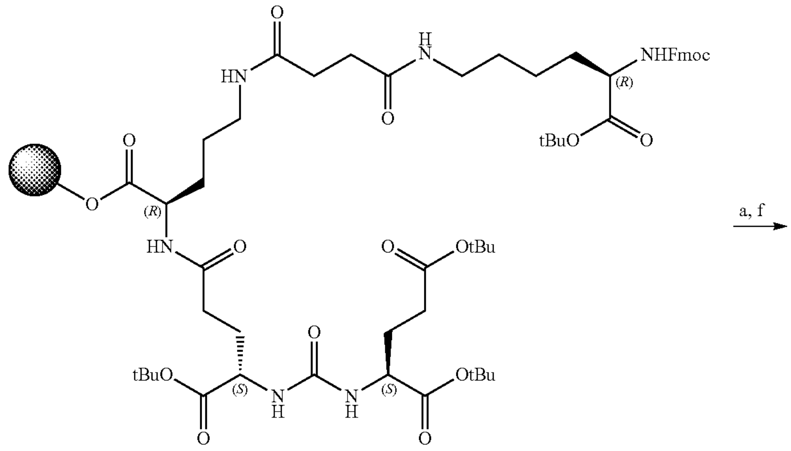
XVIII

-continued

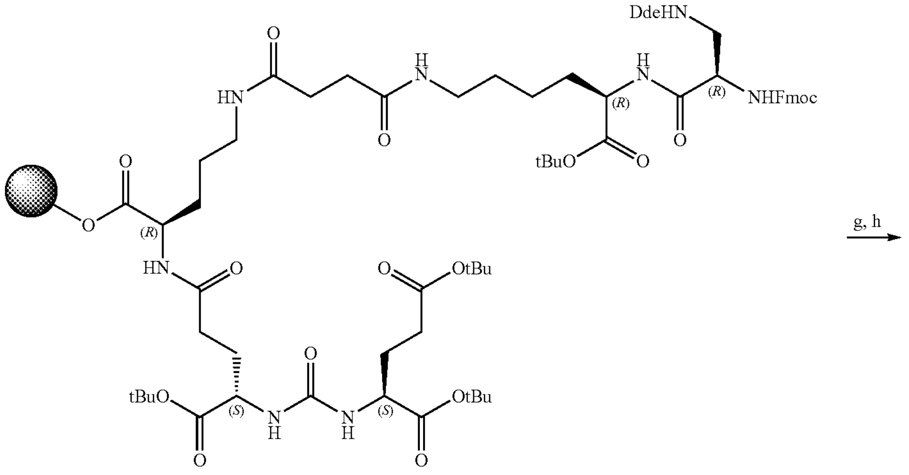

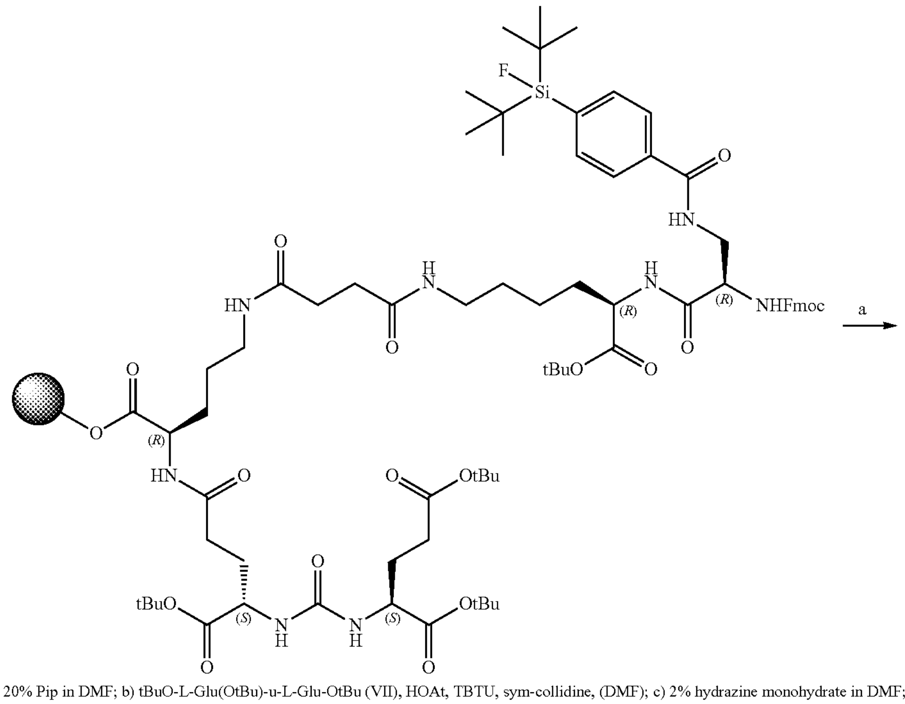

XI a) 20% Pip in DMF; b) tBuO-L-Glu(OtBu)-u-L-Glu-OtBu (VII), HOAt, TBTU, sym-collidine, (DMF); c) 2% hydrazine monohydrate in DMF; d) succinic anhydride, DIPEA (DMF); e) Fmoc-D-Lys-OtBu, HOAt, TBTU, sym-collidine, (DMF); f) Fmoc-D-Dap(Dde)-OH, HOAt, TBTU, sym-collidine, (DMF); g) imidazole, hydroxylamine hydrochloride, (DMF/NMP); h) 4-(di-tert-butylfluorosilyl)benzoic acid (IV), HOAt, TBTU, (DMF).

The resin-bound precursor XI for the synthesis of novel SiFA-PSMA ligands was obtained via SPPS (Scheme 7). Therefore, 2-CTC-resin was loaded with Fmoc-D-Orn(Dde)-OH (GSP1). The amino acid was subsequently Fmoc-deprotected (GSP2) and coupled with tBuO-L-Glu(OtBu)-u-L-Glu-OtBu (VII) (GSP3a). After cleaving the Dde-protecting group (GSP4a), the resulting N-amine was coupled with succinic anhydride (GSP3b). Then, Fmoc-D-Lys-OtBu was coupled with the carboxyl functionality resulting from the anhydride opening (GSP3a) and the Fmoc-protecting group was cleaved (GSP2). The resin-bound peptide was further elongated with Fmoc-D-Dap(Dde)-OH (GSP3a) and Dde-deprotected (GSP4b). Finally, the resulting $N^{\beta}$-amine was coupled with 4-(di-tert-butylfluorosilyl)benzoic acid (IV) (GSP3c) and the resin-bound peptide was Fmoc-deprotected (GSP2), affording the SiFA-PSMA ligand precursor XI.

XI
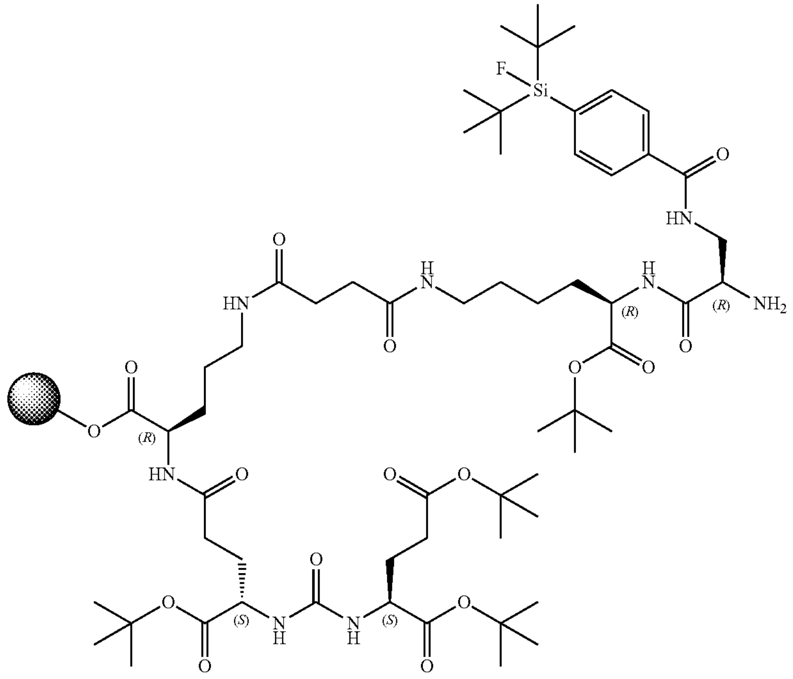
2.8.2 Examples 1a to 1k: SiFA-PSMA Ligands 01 a-k
Scheme 8. Synthesis of SiFA-PSMA ligands 01 a-k
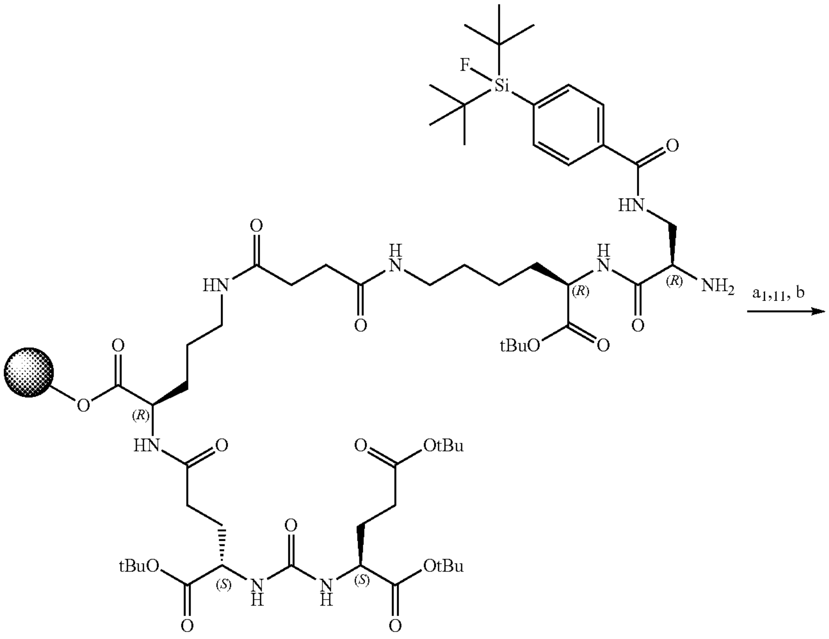

-continued
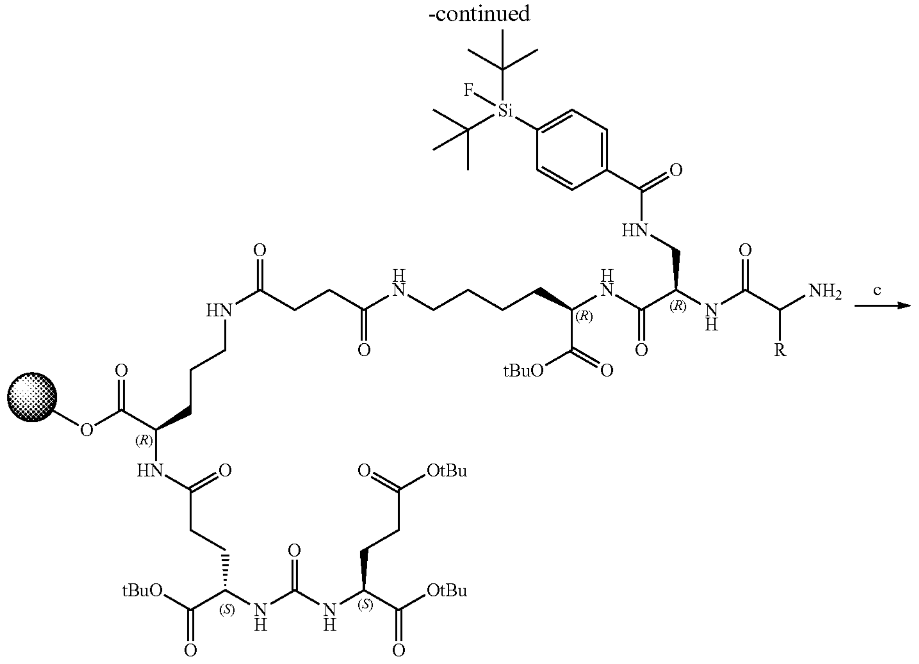
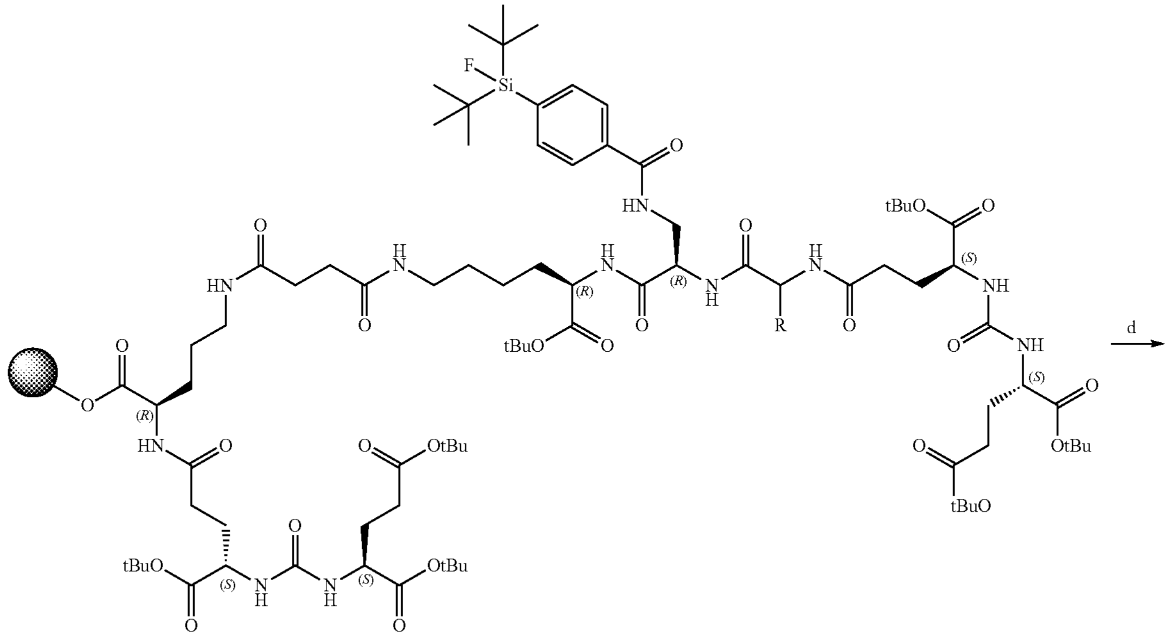
R = D-Asp
01 a
R = D-Glu
01 b
R =L-Glu
01 c
R =D-Cit
01 d
R =D-Dap
01 e -continued R =D-Orn 01 f R =D-Lys 01 g R =L-Lys 01 h R = Gly 01 i R = D-Thr 01 j R = D-Phe 01 k $a_1$) Fmoc-D-Asp(OtBu)-OH, HOAt, TBTU, sym-collidine, (DMF);
$a_2$) Fmoc-D-Glu(OtBu)-OH, HOAt, TBTU, sym-collidine, (DMF);
$a_3$) Fmoc-L-Glu(OtBu)-OH, HOAt, TBTU, sym-collidine, (DMF);
$a_4$) Fmoc-D-Cit-OH, HOAt, TBTU, sym-collidine, (DMF);
$a_5$) Fmoc-D-Dap(Boc)-OH, HOAt, TBTU, sym-collidine, (DMF);
$a_6$) Fmoc-D-Orn(Boc)-OH, HOAt, TBTU, sym-collidine, (DMF);
$a_7$) Fmoc-D-Lys(Boc)-OH, HOAt, TBTU, sym-collidine, (DMF);
$a_8$) Fmoc-L-Lys(Boc)-OH, HOAt, TBTU, sym-collidine, (DMF);
$a_9$) Fmoc-Gly-OH, HOAt, TBTU, sym-collidine, (DMF);
$a_{10}$) Fmoc-D-Thr(OtBoc)-OH, HOAt, TBTU, sym-collidine, (DMF);
$a_{11}$) Fmoc-D-Phe-OH, HOAt, TBTU, sym-collidine, (DMF);
b) 20% Pip in DMF;
c) tBuO-L-Glu(OtBu)-u-L-Glu-OtBu (VII), HOAt, TBTU, sym-collidine, (DMF);
d) 95% TFA/2.5% TIPS/2.5% water.

SiFA-PSMA ligands 01 a-k were synthesized according to the general procedures for SPPS (Scheme 8). Briefly, resin-bound peptide XI was coupled with the respective Fmoc-protected amino acid (GSP3a). After cleavage of the Fmoc-protecting group (GSP2), the resulting NV-amine was coupled with tBuO-L-Glu(OtBu)-u-L-Glu-OtBu (VII) (GSP3a). Finally, the ligand was cleaved from the resin under removal of acid-labile protecting groups (GSP5) and purified via prep. RP-HPLC. SiFA-PSMA ligands 01 a-k were obtained as colorless solids.

01 a-k

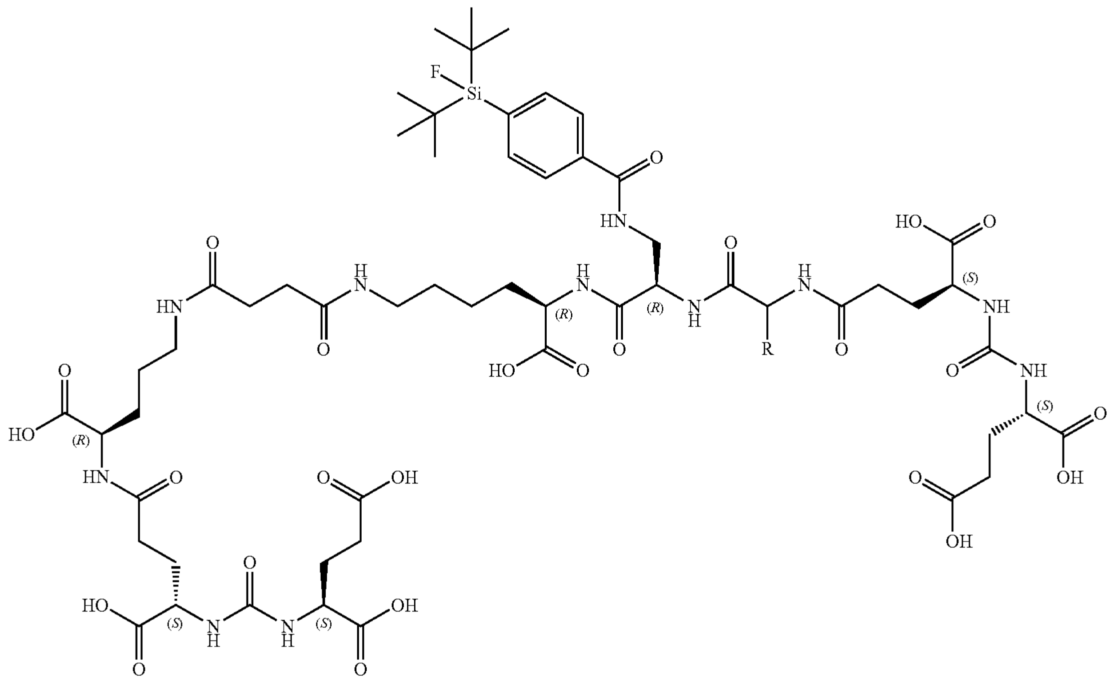

-continued 01 a R = D-Asp
01 b R = D-Glu
01 c R = L-Glu
01 d R = D-Cit
01 e R = D-Dap
01 f R = D-Orn
01 g R = D-Lys
01 h R = L-Lys
01 i R = Gly
01 j R = D-Thr
01 k R = D-Phe As will be understood, R=D-Asp, D-Glu, L-Glu, D-Cit, D-Dap, D-Orn, D-Lys, L-Lys, Gly, D-Thr and D-Phe indicates that the amino acid unit —(CO)—CH(R)—NH— bearing the group R in the formula of compounds 01 a-k is derived from D-Asp (example 01 a), D-Glu (example 01 b), L-Glu (example 01 c), D-Cit (example 01 d), D-Dap (example 01 e), D-Orn (example 01 f), D-Lys (example 01 g), L-Lys (example 01 h), Gly (example 01 i), D-Thr (example 01 j) and D-Phe (example 01 k), respectively.

01 a: prep. RP-HPLC (column IV, 38-45% B in A, 20 min, λ=220 nm): $t_R$=9.4 min; yield: 6.40 mg (4.47 μmol, 36%); anal. RP-HPLC (column III, 10-70% B in A, 15 min, λ=220 nm): $t_R$=11.2 min; purity: 96%; MS (ESI, positive): m/z calc. m.i. mass ($C_{59}H_{88}FN_{11}O_{27}Si$): 1429.6, m/z found: 716.2 $[M+2H]^{2+}$, 1430.9 $[M+H]^+$.

01 b: prep. RP-HPLC (column IV, 38-45% B in A, 20 min, λ=220 nm): $t_R$=9.6 min; yield: 4.70 mg (3.25 μmol, 40%); anal. RP-HPLC (column III, 10-70% B in A, 15 min, λ=220 nm): $t_R$=11.5 min; purity: 95%; MS (ESI, positive): m/z calc. m.i. mass ($C_{60}H_{90}FN_{11}O_{27}Si$): 1443.6, m/z found: 723.1 $[M+2H]^{2+}$, 1445.0 $[M+H]^+$.

01 c: prep. RP-HPLC (column IV, 38-45% B in A, 20 min, λ=220 nm): $t_R$=11.0 min; yield: 4.34 mg (3.00 μmol, 49%); anal. RP-HPLC (column III, 10-70% B in A, 15 min, λ=220 nm): $t_R$=11.4 min; purity: 98%; MS (ESI, positive): m/z calc. m.i. mass ($C_{60}H_{90}FN_{11}O_{27}Si$): 1443.6, m/z found: 723.2 $[M+2H]^{2+}$, 1444.7 $[M+H]^+$.

01 d: prep. RP-HPLC (column IV, 38-45% B in A, 20 min, λ=220 nm): $t_R$=8.2 min; yield: 4.01 mg (2.72 μmol, 56%); anal. RP-HPLC (column III, 10-70% B in A, 15 min, λ=220 nm): $t_R$=11.0 min; purity: 99%; MS (ESI, positive): m/z calc. m.i. mass ($C_{61}H_{94}FN_{13}O_{26}Si$): 1471.6, m/z found: 737.2 $[M+2H]^{2+}$, 1473.0 $[M+H]^+$.

01 f: prep. RP-HPLC (column IV, 38-45% B in A, 20 min, λ=220 nm): $t_R$=6.4 min; yield: 3.82 mg (2.47 μmol, 59%); anal. RP-HPLC (column III, 10-70% B in A, 15 min, λ=220 nm): $t_R$=10.8 min; purity: 98%; MS (ESI, positive): m/z calc. m.i. mass ($C_{60}H_{93}FN_{12}O_{25}Si$): 1428.6, m/z found: 715.7 $[M+2H]^{2+}$, 1429.8 $[M+H]^+$.

01 g: prep. RP-HPLC (column VI, 40-70% B in A, 20 min, λ=220 nm): $t_R$=6.3 min; yield: 7.96 mg (5.11 μmol, 49%); anal. RP-HPLC (column III, 10-70% B in A, 15 min, λ=220 nm): $t_R$=10.9 min; purity: 99%; MS (ESI, positive): m/z calc. m.i. mass ($C_{61}H_{95}FN_{12}O_{25}Si$): 1442.6, m/z found: 722.5.0 $[M+2H]^{2+}$, 1443.6 $[M+H]^+$.

01 h: prep. RP-HPLC (column VIII, 35-40% B in A, 20 min, λ=220 nm): $t_R$=7.7 min; yield: 4.96 mg (3.18 μmol, 37%); anal. RP-HPLC (column II, 10-70% B in A, 15 min, λ=220 nm): $t_R$=10.1 min; purity: 98%; MS (ESI, positive): m/z calc. m.i. mass ($C_{61}H_{95}FN_{12}O_{25}Si$): 1442.6, m/z found: 722.8 $[M+2H]^{2+}$, 1443.8 $[M+H]^+$.

01 i: prep. RP-HPLC (column IV, 38-45% B in A, 20 min, λ=220 nm): $t_R$=10.5 min; yield: 7.46 mg (5.44 μmol, 50%); anal. RP-HPLC (column II, 10-70% B in A, 15 min, λ=220 nm): $t_R$=11.1 min; purity: 98%; MS (ESI, positive): m/z calc. m.i. mass ($C_{57}H_{86}FN_{11}O_{25}Si$): 1371.6, m/z found: 687.3 $[M+2H]^{2+}$, 1373.6 $[M+H]^+$.

01 j: prep. RP-HPLC (column IV, 35-45% B in A, 20 min, λ=220 nm): $t_R$=13.9 min; yield: 5.56 mg (3.93 μmol, 36%); anal. RP-HPLC (column II, 10-70% B in A, 15 min, λ=220 nm): $t_R$=11.0 min; purity: 97%; MS (ESI, positive): m/z calc. m.i. mass ($C_{59}H_{90}FN_{11}O_{26}Si$): 1415.6, m/z found: 709.1 $[M+2H]^{2+}$, 1417.0 $[M+H]^+$.

01 k: prep. RP-HPLC (column IV, 40-60% B in A, 20 min, λ=220 nm): $t_R$=11.2 min; yield: 7.06 mg (4.83 μmol, 47%); anal. RP-HPLC (column II, 10-70% B in A, 15 min, λ=220 nm): $t_R$=12.5 min; purity: 98%; MS (ESI, positive): m/z calc. m.i. mass ($C_{64}H_{92}FN_{11}O_{25}Si$): 1461.6, m/z found: 732.5 $[M+2H]^{2+}$, 1464.0 $[M+H]^+$.

2.8.3 Example 2a: SiFA-PSMA Ligand 02 a
Scheme 9. Synthesis of SiFA-PSMA ligand 02 a
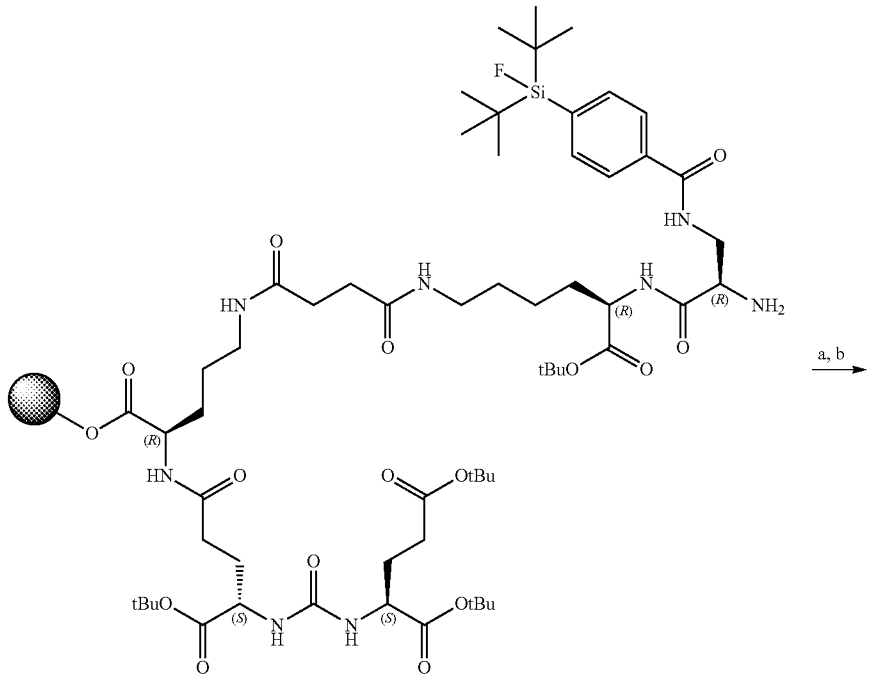
XI
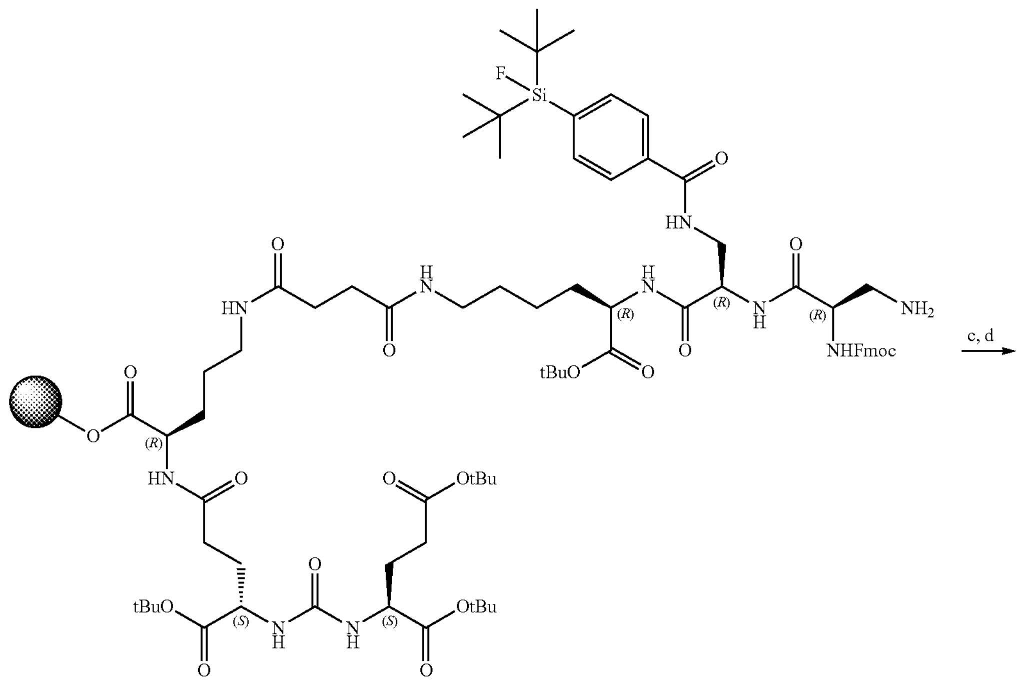

-continued

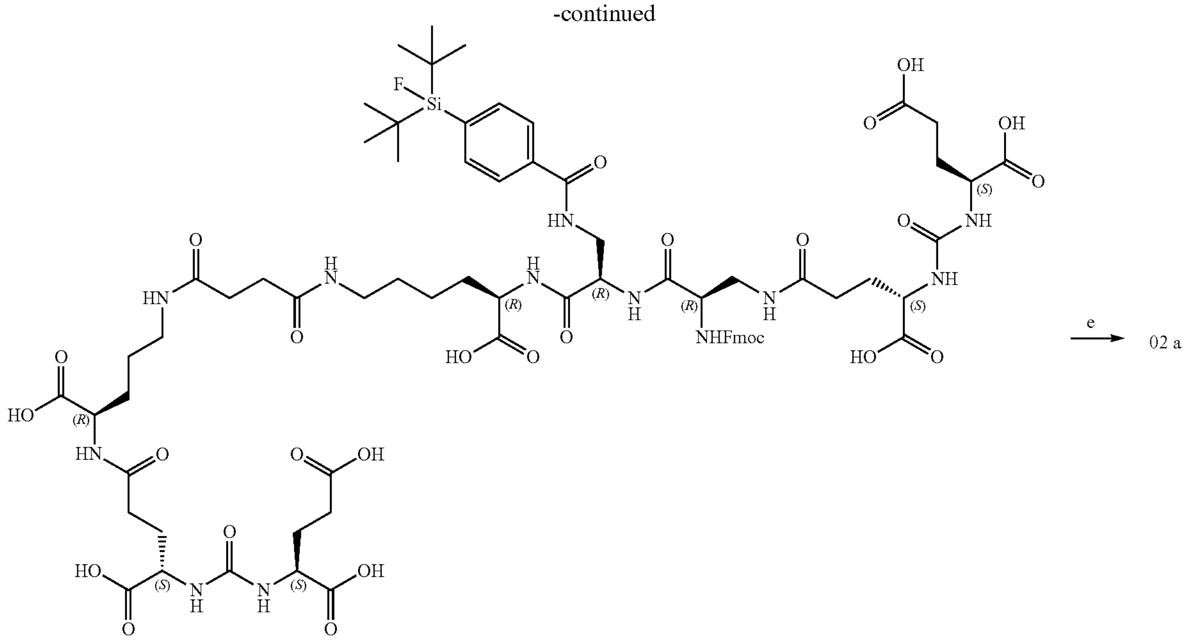

a) Fmoc-D-Dap(Dde)-OH, HOAt, TBTU, sym-collidine, (DMF); b) imidazole, hydroxylamine hydrochloride, (DMF/NMP); c) tBuO-L-Glu(OtBu)-u-L-Glu-OtBu (VII), HOAt, TBTU, sym-collidine, (DMF); d) 95% TFA/2.5% TIPS/2.5% water; e) 20% Pip in DMF.

SiFA-PSMA ligand 02 a was synthesized according to the mentioned procedures for SPPS (Scheme 9). Shortly, resin-bound peptide XI was coupled with Fmoc-D-Dap(Dde)-OH (GSP3a). After cleaving the Dde-protecting group (GSP4b), the resulting $N^{\beta}$-amine was coupled with tBuO-L-Glu (OtBu)-u-L-Glu-OtBu (VII) (GSP3a). The Fmoc-protected ligand was subsequently cleaved from the resin under removal of tBu-protecting groups (GSP5) and purified via prep. RP-HPLC (column V, 40-70% B in A, 20 min, $\lambda$=220 nm, $t_R$=11.7 min). Finally, the obtained peptide was Fmoc-deprotected (GSP2) and again purified via prep. RP-HPLC yielding SiFA-PSMA ligand 02 a as a colorless solid.

02 a

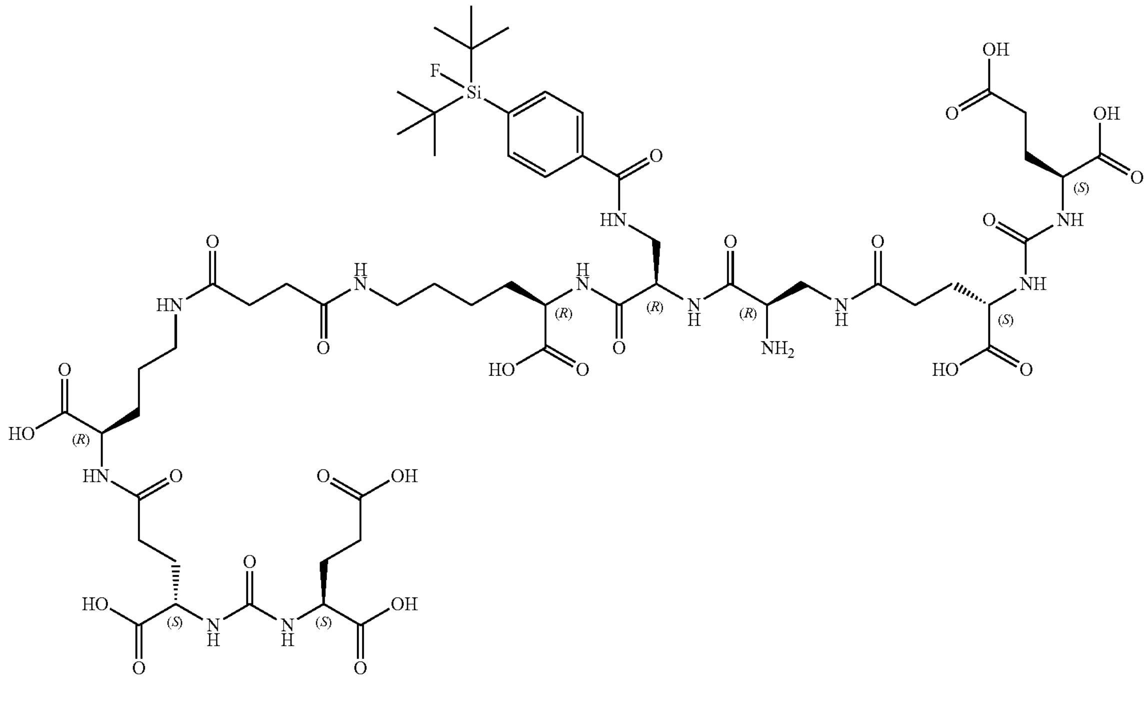

02 a: prep. RP-HPLC (column IV, 35-45% B in A, 20 min, $\lambda$=220 nm): $t_R$=11.6 min; yield: 3.48 mg (2.30 µmol, 21%); anal. RP-HPLC (column III, 10-70% B in A, 15 min, $\lambda$=220 nm): $t_R$=11.4 min; purity: 97%; MS (ESI, positive): m/z calc. m.i. mass ($C_{58}H_{89}FN_{12}O_{25}Si$): 1400.6, m/z found: 701.7 $[M+2H]^{2+}$, 1402.0 $[M+H]^+$.
2.8.4: Examples 2 b and 2 c: SiFA-PSMA Ligands 02 b-c
Scheme 10. Synthesis of SiFA-PSMA ligands 02 b-c
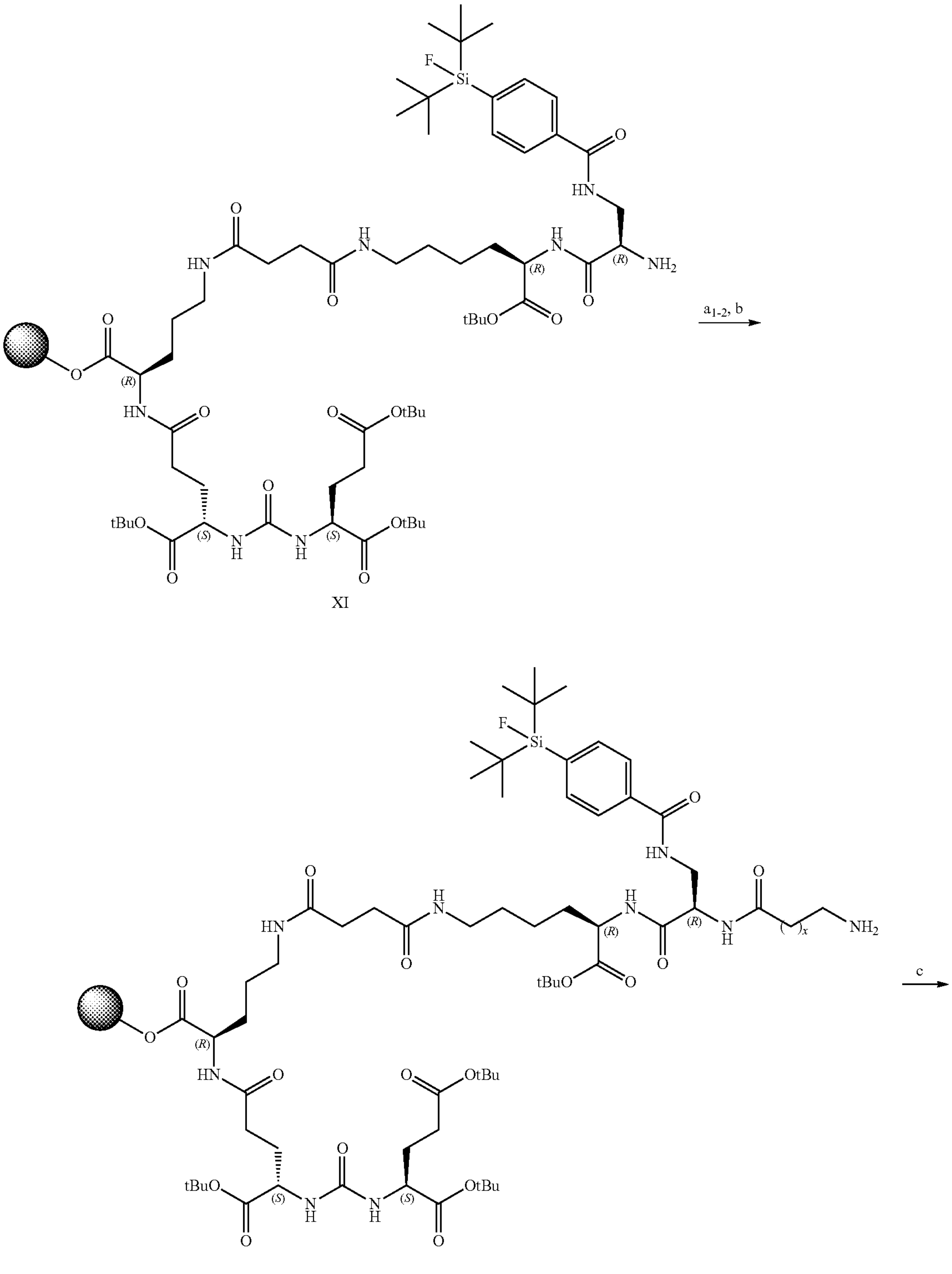

-continued

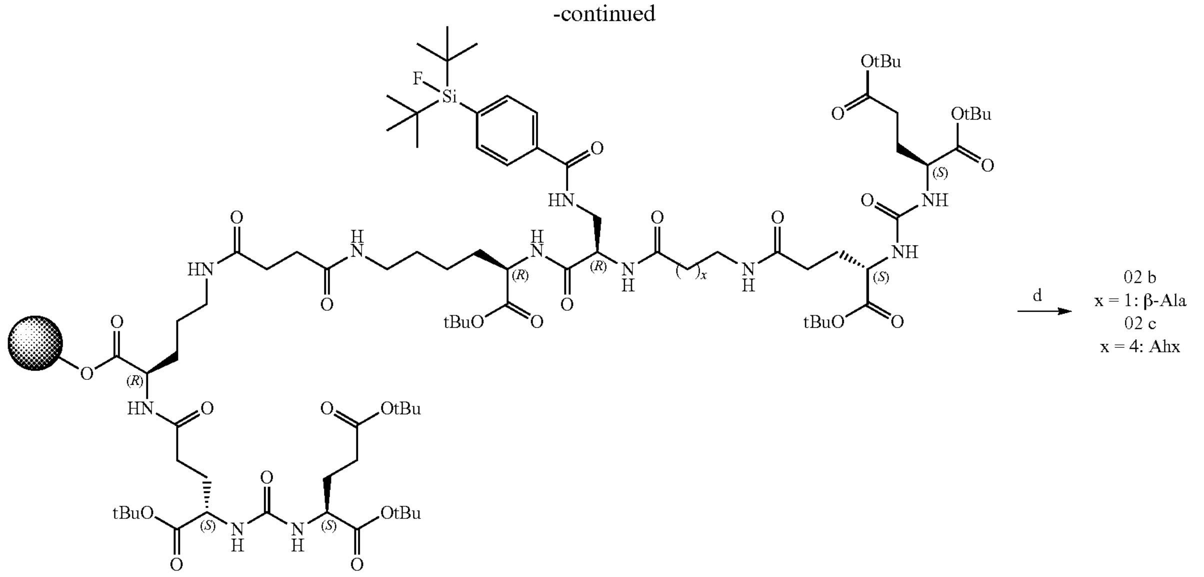

$a_1$) Fmoc-β-Ala-OH, HOAt, TBTU, sym-collidine, (DMF); $a_2$) Fmoc-Ahx-OH, HOAt, TBTU, sym-collidine, (DMF); b) 20% Pip in DMF; c) tBuO-L-Glu(OtBu)-u-L-Glu-OtBu (VII), HOAt, TBTU, sym-collidine, (DMF); d) 95% TFA/2.5% TIPS/2.5% water.

SiFA-PSMA ligands 02 b-c were synthesized according to the mentioned procedures for SPPS (Scheme X). In brief, resin-bound peptide XI was coupled with the respective Fmoc-protected amino acid (GSP3a) and the peptide was subsequently Fmoc-deprotected (GSP2). Afterwards, the resulting amine was coupled with tBuO-L-Glu(OtBu)-u-L-Glu-OtBu (VII) (GSP3a). The ligands were finally cleaved from the resin under removal of tBu-protecting groups (GSP5) and purified via prep. RP-HPLC yielding SiFA-PSMA ligands 02 b-c as colorless solids.

02 b-c

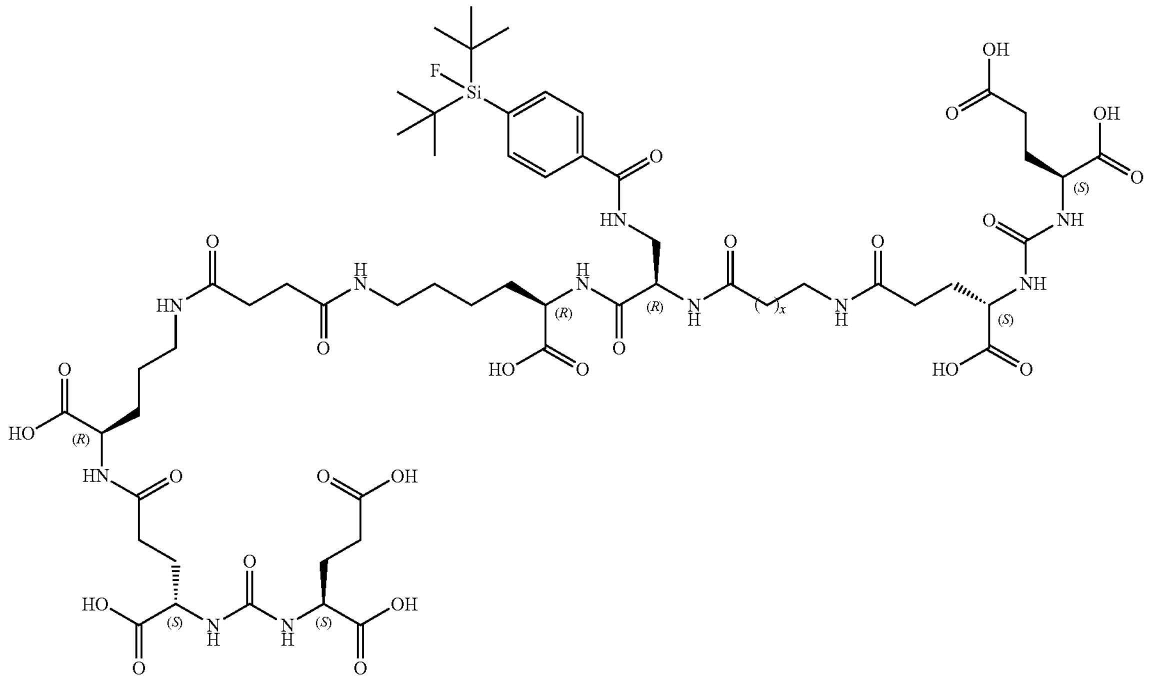

02 b x = 1: β-Ala
02 c x = 4: Ahx 02 b: prep. RP-HPLC (column VII, 40-50% B in A, 20 min, λ=220 nm): $t_R$=17.0 min; yield: 3.89 mg (2.81 μmol, 25%); anal. RP-HPLC (column II, 10-70% B in A, 15 min, λ=220 nm): $t_R$=10.9 min; purity: 97%; MS (ESI, positive): m/z calc. m.i. mass ($C_{58}H_{88}FN_{11}O_{25}Si$): 1385.6, m/z found: 694.0 $[M+2H]^{2+}$, 1386.8 $[M+H]^+$.

02 c: prep. RP-HPLC (column VII, 40-50% B in A, 20 min, λ=220 nm): $t_R$=13.0 min; yield: 5.00 mg (3.50 μmol, 29%); anal. RP-HPLC (column II, 10-70% B in A, 15 min, λ=220 nm): $t_R$=11.1 min; purity: 96%; MS (ESI, positive): m/z calc. m.i. mass ($C_{61}H_{94}FN_{11}O_{25}Si$): 1427.6, m/z found: 714.4 $[M+2H]^{2+}$, 1427.4 $[M+H]^+$.

2.8.5 Example 2 d: SiFA-PSMA Ligand 02 d

Scheme 11. Synthesis of SiFA-PSMA ligand 02 d

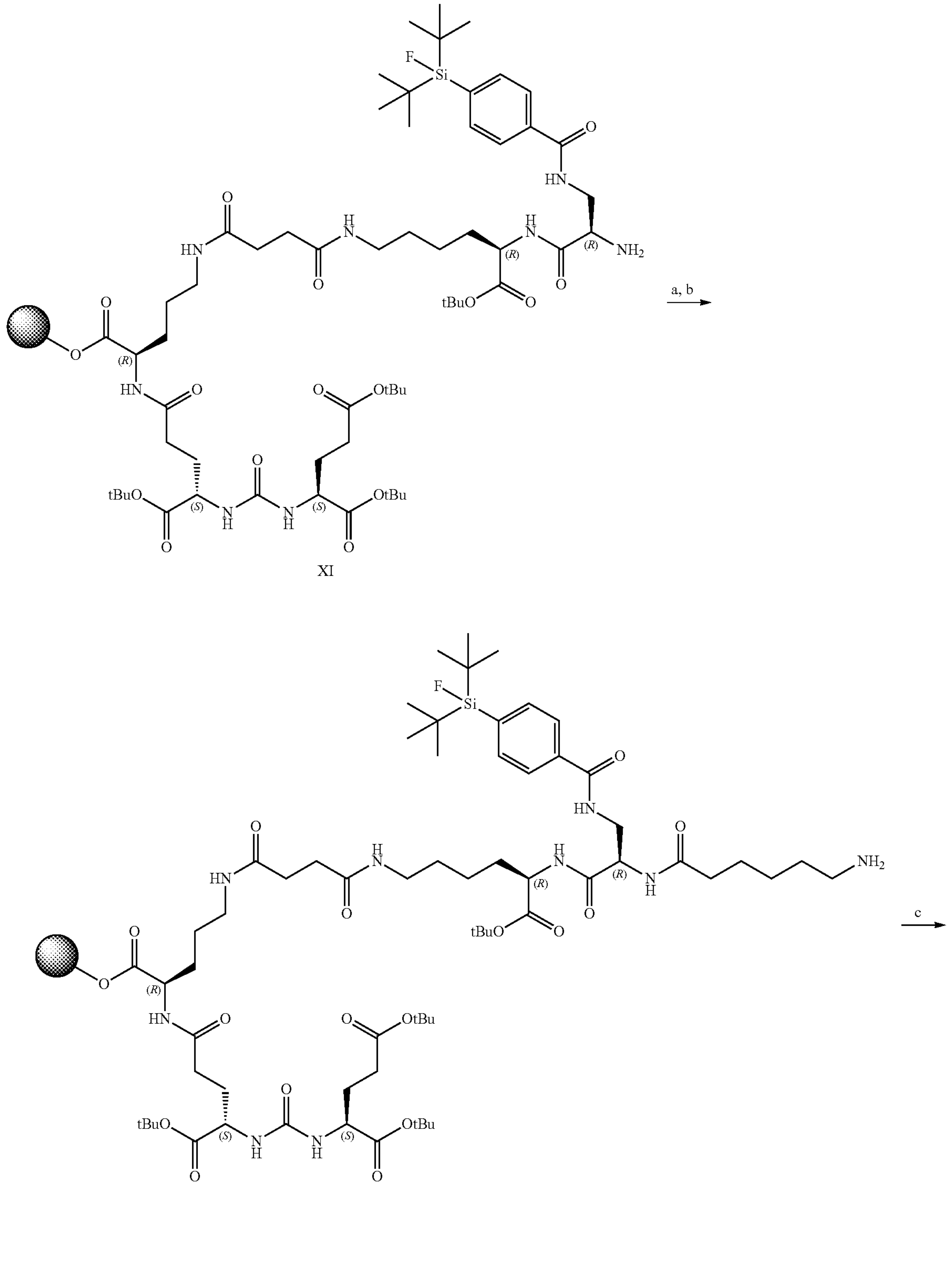

-continued

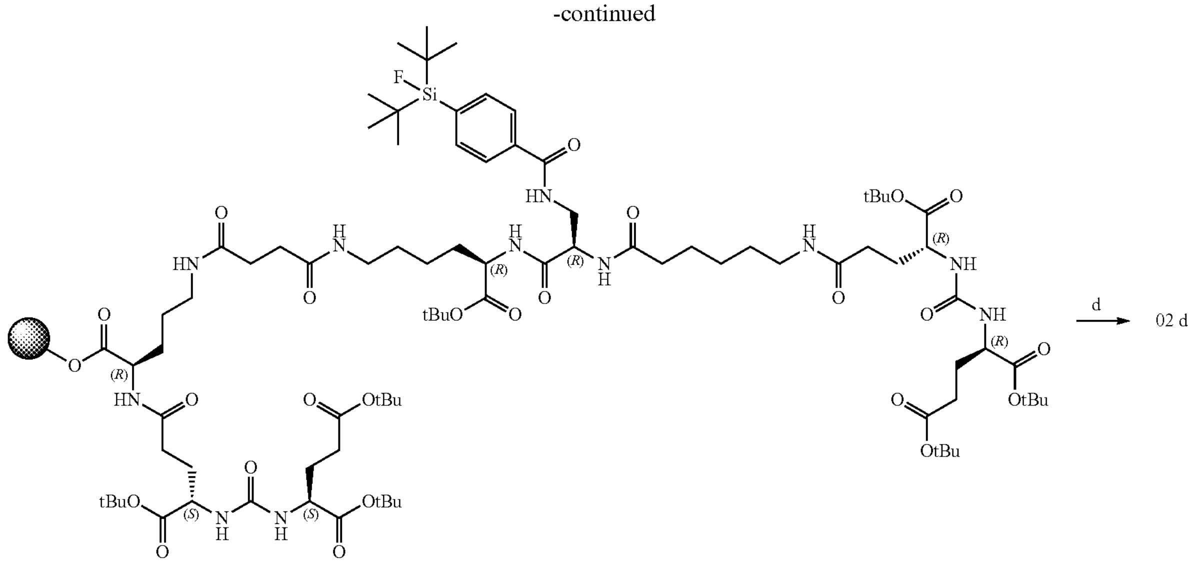

a) Fmoc-Ahx-OH, HOAt, TBTU, sym-collidine, (DMF); b) 20% Pip in DMF; c) tBuO-D-Glu(OtBu)-u-D-Glu-OtBu (XV), HOAt, TBTU, sym-collidine, (DMF); d) 95% TFA/2.5% TIPS/2.5% water.

SiFA-PSMA ligand 02 d was synthesized in analogy to SiFA-PSMA ligand 02 c (Scheme 11). Briefly, resin-bound peptide XI was coupled with Fmoc-Ahx-OH (GSP3a). After cleaving the Fmoc-protecting group (GSP2), the amine was coupled with tBuO-D-Glu(OtBu)-u-D-Glu-OtBu (XV) (GSP3a). The ligand was finally cleaved from the resin under removal of tBu-protecting groups (GSP5) and purified via prep. RP-HPLC giving SiFA-PSMA ligand 02 d as a colorless solid.

02 d

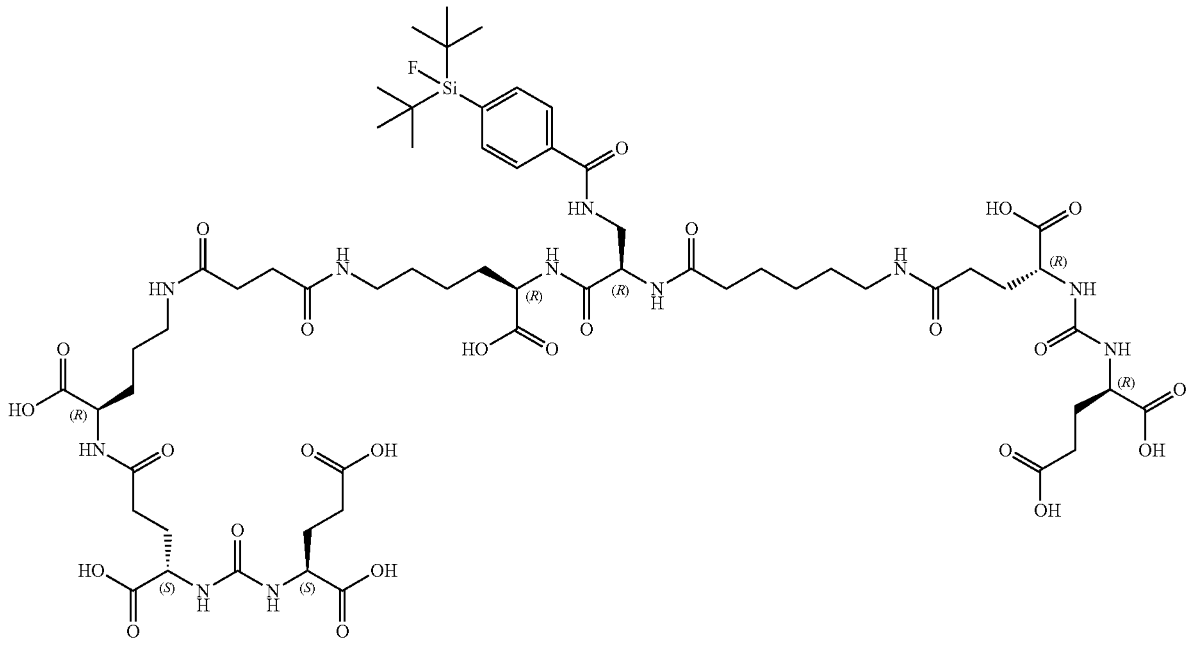

02 d: prep. RP-HPLC (column IV, 45-55% B in A, 20 min, λ=220 nm): $t_R$=5.4 min; yield: 1.24 mg (0.868 μmol, 7%); anal. RP-HPLC (column II, 10-70% B in A, 15 min, λ=220 nm): 5 $t_R$=11.0 min; purity: 99%; MS (ESI, positive): m/z calc. m.i. mass ($C_{61}H_{94}FN_{11}O_{25}Si$): 1427.6, m/z found: 714.7 $[M+2H]^{2+}$, 1427.6 $[M+H]^+$.
2.8.6 Example 2 e: SiFA-PSMA Ligand 02 e
Scheme 12. Synthesis of SiFA-PSMA ligand 02 e
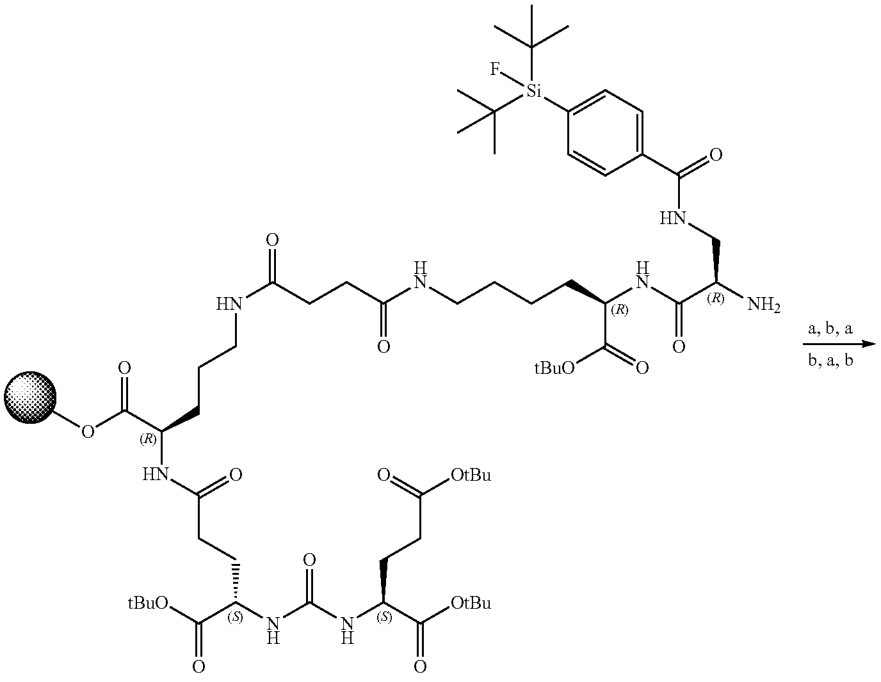
XI
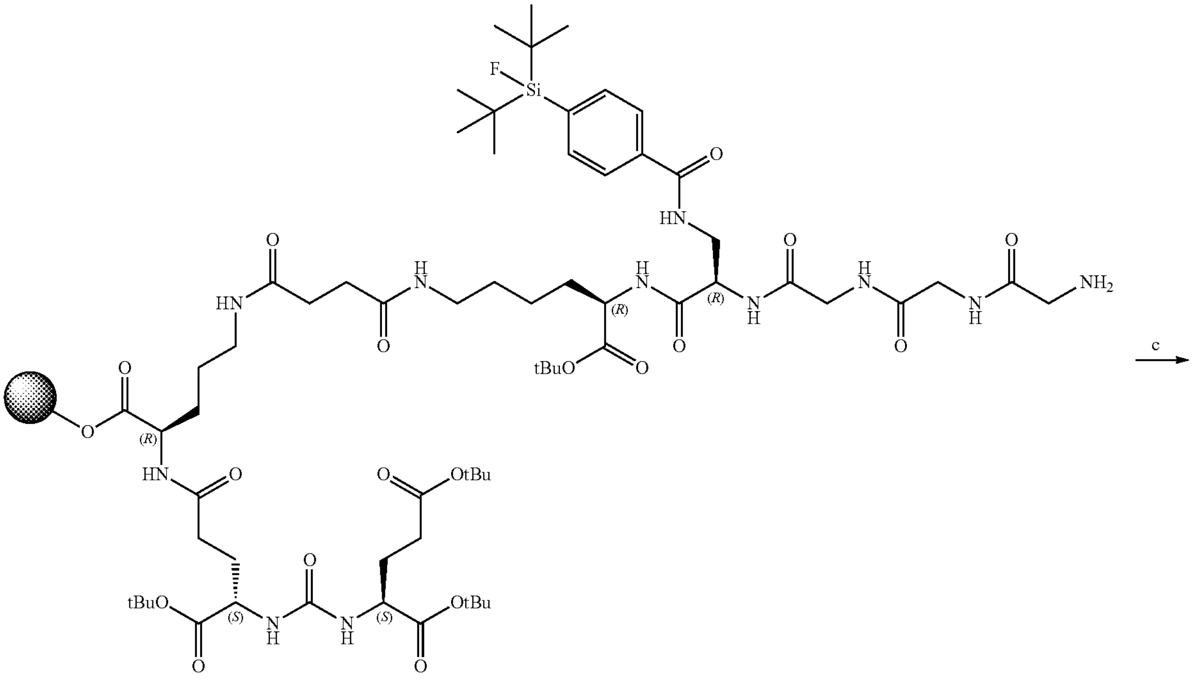

-continued

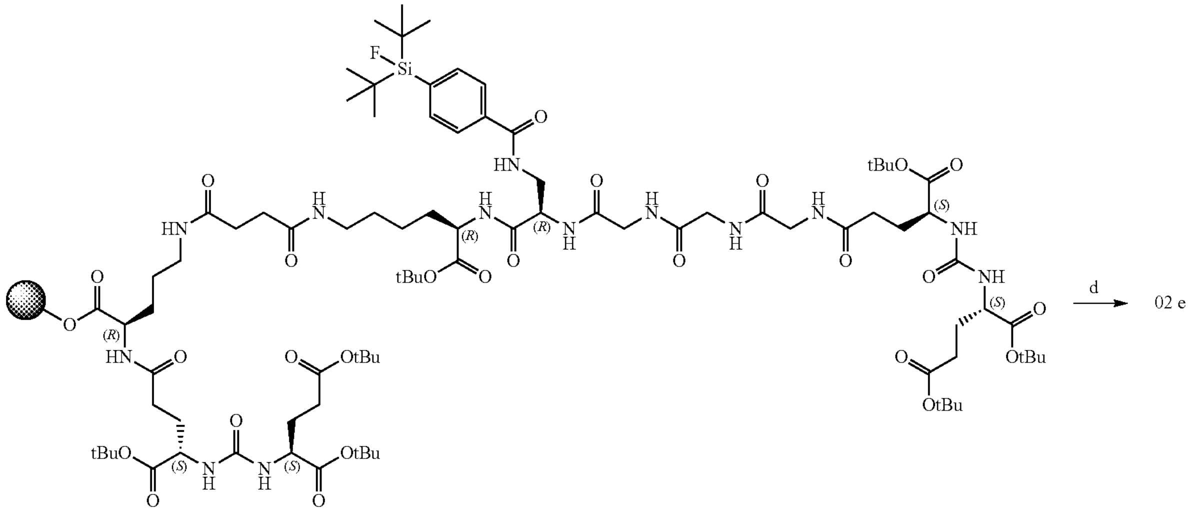

a) Fmoc-Gly-OH, HOAt, TBTU, sym-collidine, (DMF); b) 20% Pip in DMF; c) tBuO-L-Glu(OtBu)-U-L-Glu-OtBu (VII), HOAt, TBTU, sym-collidine, (DMF); d) 95% TFA/2.5% TIPS/2.5% water.

SiFA-PSMA ligand 02 e was synthesized according to the mentioned procedures for SPPS (Scheme 12). In short, resin-bound peptide XI was extended with three glycine units by repetitive coupling with Fmoc-Gly-OH (GSP3a) followed by Fmoc-deprotection (GSP2). Afterwards, the resulting amine was coupled with tBuO-L-Glu(OtBu)-u-L-Glu-OtBu (VII) (GSP3a), the ligand was finally cleaved from the resin under removal of tBu-protecting groups (GSP5) and purified via prep. RP-HPLC giving SiFA-PSMA ligand 02 e as a colorless solid.

02 e

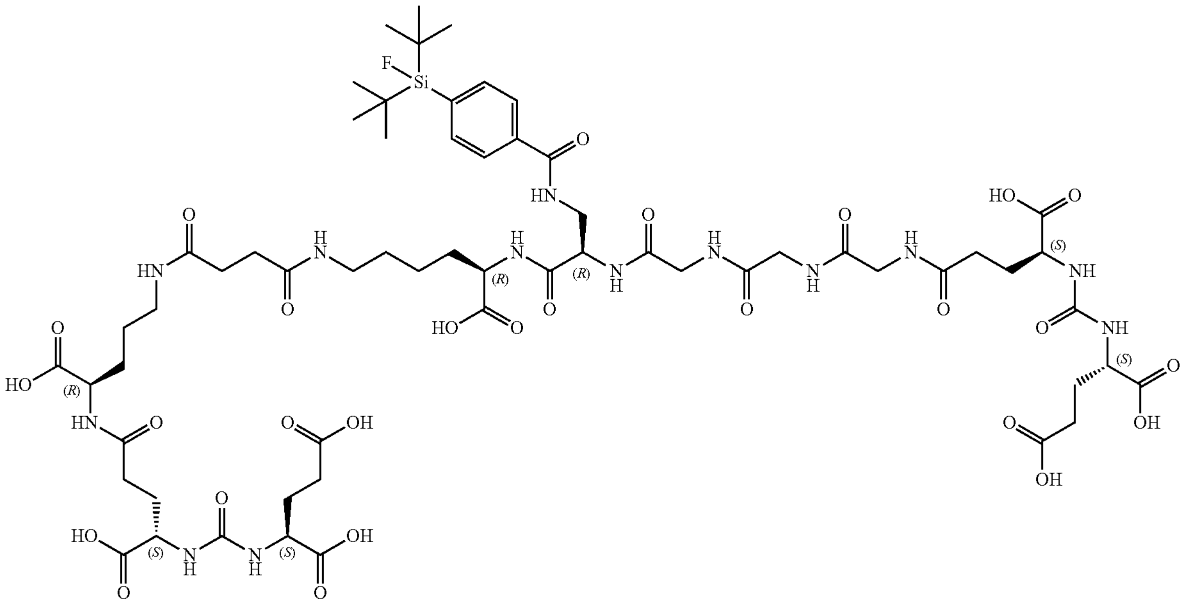

02 e: prep. RP-HPLC (column IV, 38-45% B in A, 20 min, $\lambda$=220 nm): $t_R$=9.8 min; yield: 2.12 mg (1.43 μmol, 12%); anal. RP-HPLC (column II, 10-70% B in A, 15 min, $\lambda$=220 nm): $t_R$=10.5 min; purity: 96%; MS (ESI, positive): m/z calc. m.i. mass ($C_{61}H_{92}FN_{13}O_{27}Si$): 1485.6, m/z found: 743.9 $[M+2H]^{2+}$, 1486.6 $[M+H]^+$.
2.8.7 Examples 3a to 3i: SiFA-PSMA Ligands 03 a-i
Scheme 13. Synthesis of SiFA-PSMA ligands 03 a-i
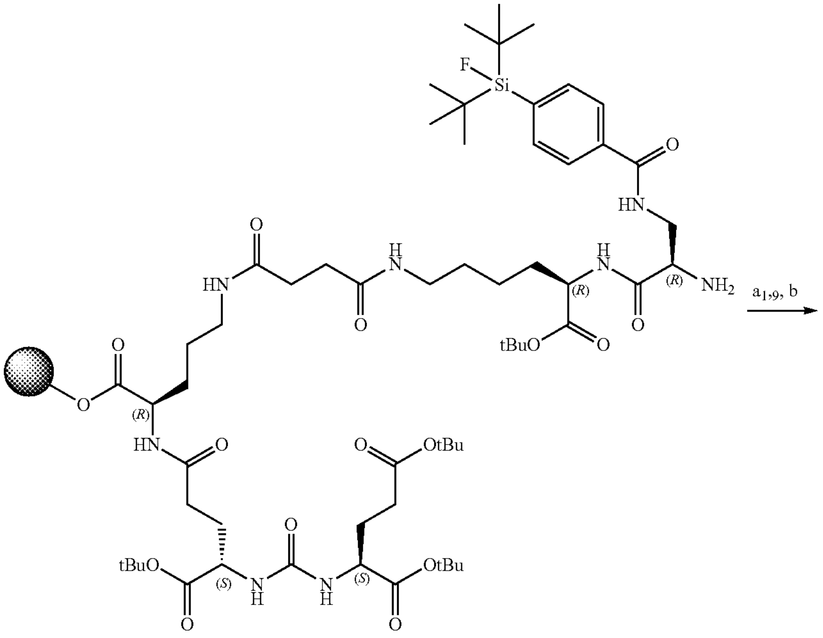
XI
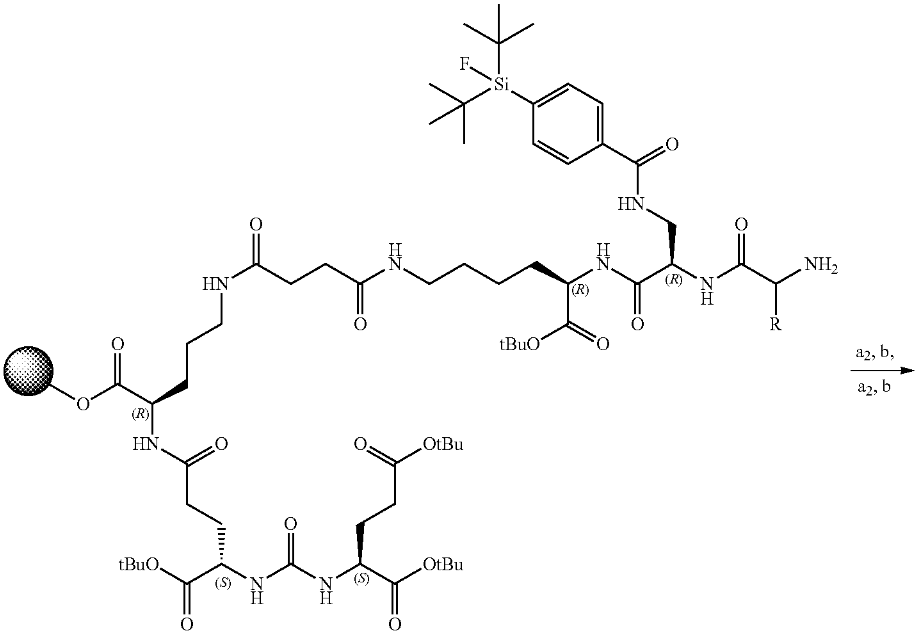

-continued

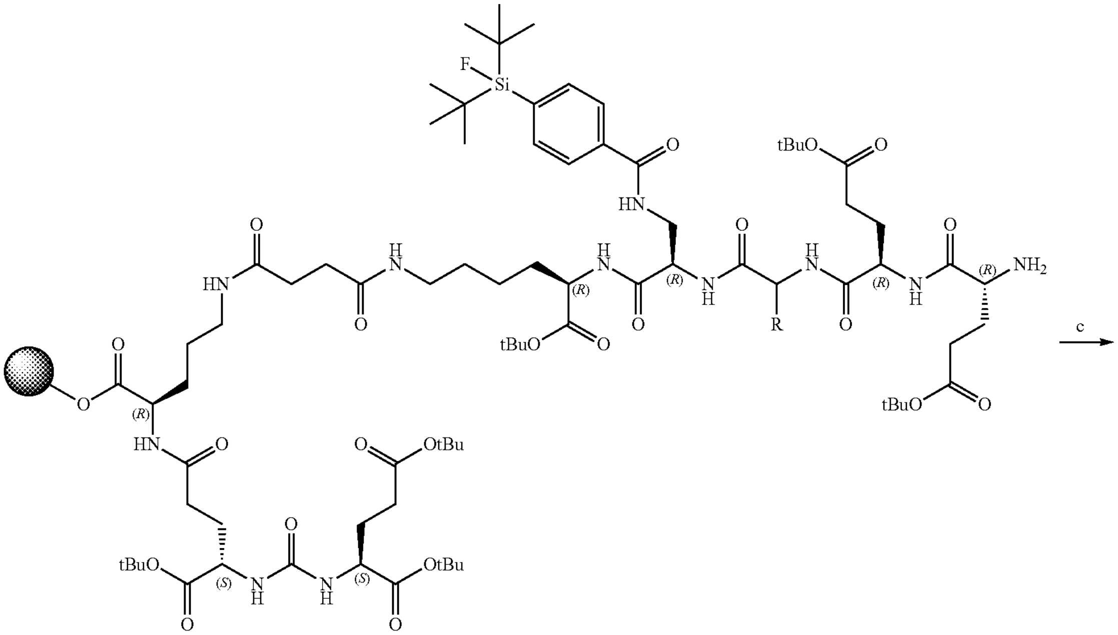

R = D-Asp
03 a
R = D-Glu
03 b
R =D-Cit
03 c
R =D-Dap
03 d
R =D-Orn
03 e
R =D-Lys
03 f
R = Gly
03 g
R = D-Thr
03 h
R = D-Phe
03 i $a_1$) Fmoc-D-Asp(OtBu)-OH, HOAt, TBTU, sym-collidine, (DMF);
$a_2$) Fmoc-D-Glu(OtBu)-OH, HOAt, TBTU, sym-collidine, (DMF);
$a_3$) Fmoc-D-Cit-OH, HOAt, TBTU, sym-collidine, (DMF);
$a_4$) Fmoc-D-Dap(Boc)-OH, HOAt, TBTU, sym-collidine, (DMF);
$a_5$) Fmoc-D-Orn(Boc)-OH, HOAt, TBTU, sym-collidine, (DMF);
$a_6$) Fmoc-D-Lys(Boc)-OH, HOAt, TBTU, sym-collidine, (DMF);
$a_7$) Fmoc-Gly-OH, HOAt, TBTU, sym-collidine, (DMF);
$a_8$) Fmoc-D-Thr(OtBu)-OH, HOAt, TBTU, sym-collidine, (DMF);
$a_9$) Fmoc-D-Phe-OH, HOAt, TBTU, sym-collidine, (DMF);
b) 20% Pip in DMF;
c) 95% TFA/2.5% TIPS/2.5% water.

SiFA-PSMA ligands 03 a-f were synthesized according to the general procedures for SPPS (Scheme 13). Briefly, resin-bound peptide XI was coupled with the respective Fmoc-protected amino acid (GSP3a). After cleavage of the Fmoc-protecting group (GSP2), the resulting $N^{\beta}$-amine was coupled with Fmoc-D-Glu(OtBu)-OH (GSP3a) and the peptide was again Fmoc-deprotected (GSP2). This procedure was repeated one more time. The ligand was finally cleaved from the resin under removal of acid-labile protecting groups (GSP5) and purified via prep. RP-HPLC. SiFA-PSMA ligands 03 a-i resulted as colorless solids.

03 a-i

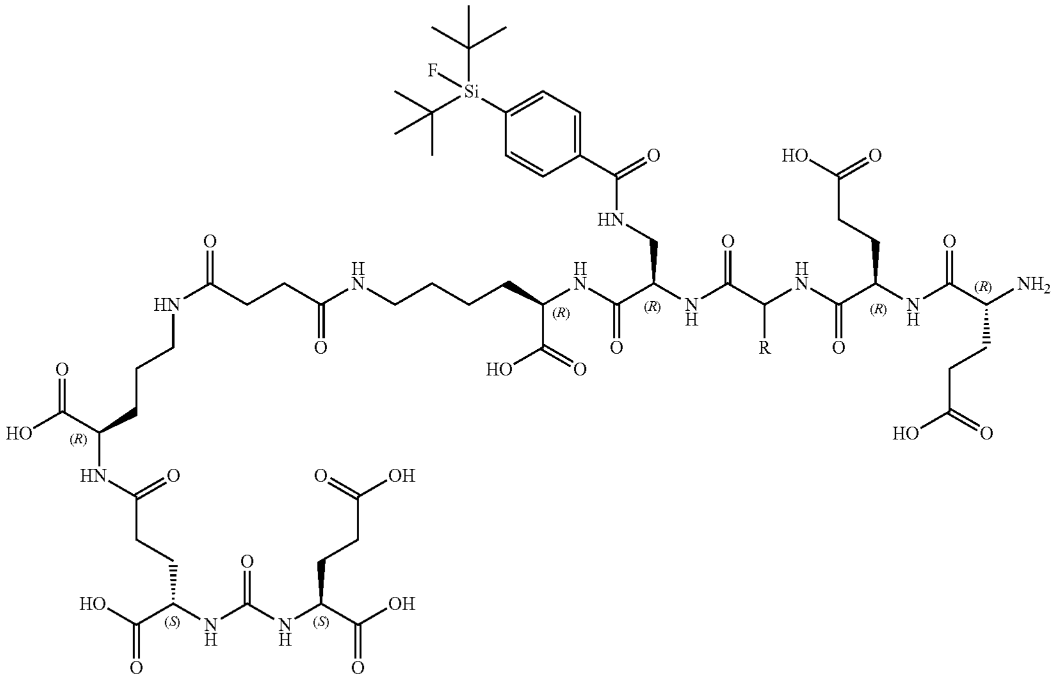

03 a R = D-Asp
03 b R = D-Glu
03 c R = D-Cit
03 d R = D-Dap
03 e R = D-Orn
03 f R = D-Lys
03 g R = Gly
03 h R = D-Thr
03 i R = D-Phe

As will be understood, R=D-Asp, D-Glu, D-Cit, D-Dap, D-Orn, D-Lys, Gly, D-Thr and D-Phe indicates that the amino acid unit —(CO)—CH(R)—NH— bearing the group R in the formula of compounds 03 a-i is derived from D-Asp (example 03 a), D-Glu (example 03 b), D-Cit (example 03 c), D-Dap (example 03 d), D-Orn (example 03 e), D-Lys (example 03 f), Gly (example 03 g), D-Thr (example 03 h) and D-Phe (example 03 i), respectively.

03 a: prep. RP-HPLC (column IV, 38-45% B in A, 20 min, λ=220 nm): $t_R$=13.6 min; yield: 5.06 mg (3.37 μmol, 25%); anal. RP-HPLC (column III, 10-70% B in A, 15 min, λ=220 nm): $t_R$=11.3 min; purity: 96%; MS (ESI, positive): m/z calc. m.i. mass ($C_{58}H_{88}FN_{11}O_{25}Si$): 1385.6, m/z found: 694.1 $[M+2H]^{2+}$, 1387.0 $[M+H]^{+}$.

03 b: prep. RP-HPLC (column IV, 38-45% B in A, 20 min, λ=220 nm): $t_R$=7.8 min; yield: 5.10 mg (3.37 μmol, 25%); anal. RP-HPLC (column III, 10-70% B in A, 15 min, λ=220 nm): $t_R$=11.4 min; purity: 98%; MS (ESI, positive): m/z calc. m.i. mass ($C_{59}H_{90}FN_{11}O_{25}Si$): 1399.6, m/z found: 701.2 $[M+2H]^{2+}$, 1401.0 $[M+H]^{+}$.

03 c: prep. RP-HPLC (column IV, 38-45% B in A, 20 min, λ=220 nm): $t_R$=7.0 min; yield: 5.40 mg (3.50 μmol, 31%); anal. RP-HPLC (column III, 10-70% B in A, 15 min, λ=220 nm): $t_R$=11.0 min; purity: 98%; MS (ESI, positive): m/z calc. m.i. mass ($C_{60}H_{94}FN_{13}O_{24}Si$): 1427.6, m/z found: 715.2 $[M+2H]^{2+}$, 1428.8 $[M+H]^{+}$.

03 d: prep. RP-HPLC (column IV, 38-45% B in A, 20 min, λ=220 nm): $t_R$=5.4 min; yield: 4.65 mg (3.16 μmol, 46%); anal. RP-HPLC (column III, 10-70% B in A, 15 min, λ=220 nm): $t_R$=10.8 min; purity: 97%; MS (ESI, positive): m/z calc. m.i. mass ($C_{57}H_{89}FN_{12}O_{23}Si$): 1356.6, m/z found: 679.7 $[M+2H]^{2+}$, 1358.0 $[M+H]^{+}$.

03 e: prep. RP-HPLC (column IV, 35-40% B in A, 20 min, λ=220 nm): $t_R$=10.2 min; yield: 4.51 mg (2.80 μmol, 25%); anal. RP-HPLC (column II, 10-70% B in A, 15 min, λ=220 nm): $t_R$=9.6 min; purity: 98%; MS (ESI, positive): m/z calc. m.i. mass ($C_{59}H_{93}FN_{12}O_{23}Si$): 1384.6, m/z found: 693.8 $[M+2H]^{2+}$, 1386.7 $[M+H]^{+}$.

03 f: prep. RP-HPLC (column IV, 35-45% B in A, 20 min, λ=220 nm): $t_R$=7.5 min; yield: 7.44 mg (4.57 μmol, 40%); anal. RP-HPLC (column II, 10-70% B in A, 15 min, λ=220 nm): $t_R$=9.9 min; purity: 95%; MS (ESI, positive): m/z calc. m.i. mass ($C_{60}H_{95}FN_{12}O_{23}Si$): 1398.6, m/z found: 700.9 $[M+2H]^{2+}$, 1400.8 $[M+H]^+$.

03 g: prep. RP-HPLC (column IV, 38-45% B in A, 20 min, λ=220 nm): $t_R$=9.5 min; yield: 2.50 mg (1.73 μmol, 17%); anal. RP-HPLC (column II, 10-70% B in A, 15 min, λ=220 nm): $t_R$=10.3 min; purity: 98%; MS (ESI, positive): m/z calc. m.i. mass ($C_{56}H_{86}FN_{11}O_{23}Si$): 1327.6, m/z found: 665.0 $[M+2H]^{2+}$, 1328.7 $[M+H]^+$.

03 h: prep. RP-HPLC (column IV, 38-45% B in A, 20 min, λ=220 nm): $t_R$=9.5 min; yield: 4.38 mg (2.95 μmol, 28%); anal. RP-HPLC (column II, 10-70% B in A, 15 min, λ=220 nm): $t_R$=10.2 min; purity: >99%; MS (ESI, positive): m/z calc. m.i. mass ($C_{58}H_{90}FN_{11}O_{24}Si$): 1371.6, m/z found: 687.1 $[M+2H]^{2+}$, 1372.8 $[M+H]^+$.

03 i: prep. RP-HPLC (column IV, 40-50% B in A, 20 min, λ=220 nm): $t_R$=12.4 min; yield: 5.35 mg (3.49 μmol, 31%); anal. RP-HPLC (column II, 10-70% B in A, 15 min, λ=220 nm): $t_R$=11.3 min; purity: 99%; MS (ESI, positive): m/z calc. m.i. mass ($C_{63}H_{92}FN_{11}O_{23}Si$): 1417.6, m/z found: 710.1 $[M+2H]^{2+}$, 1418.9 $[M+H]^+$.

2.8.8 Example 4: SiFA-PSMA Ligand 04

Scheme 14. Synthesis of SiFA-PSMA ligand 04

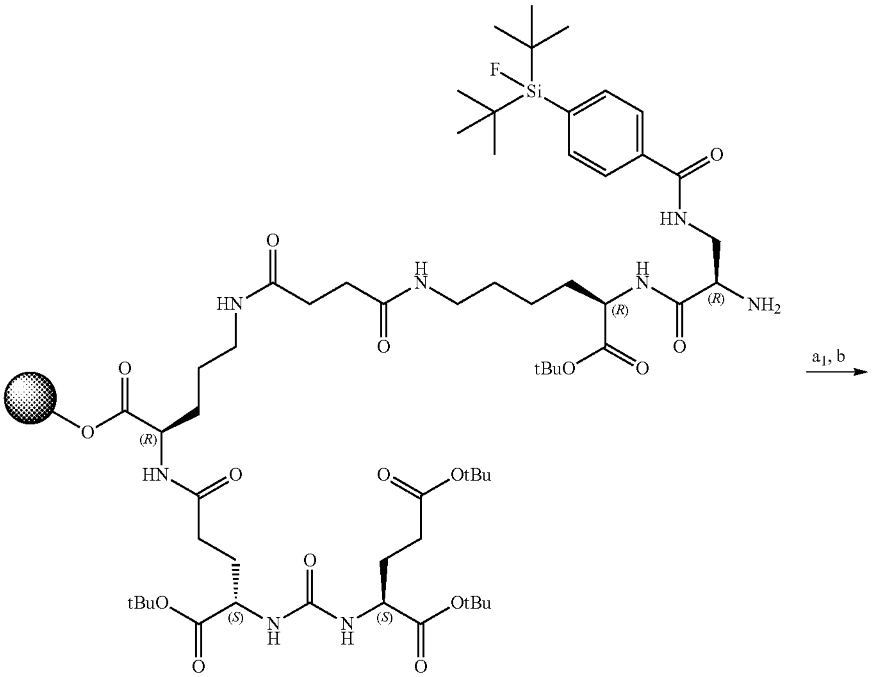

XI

-continued

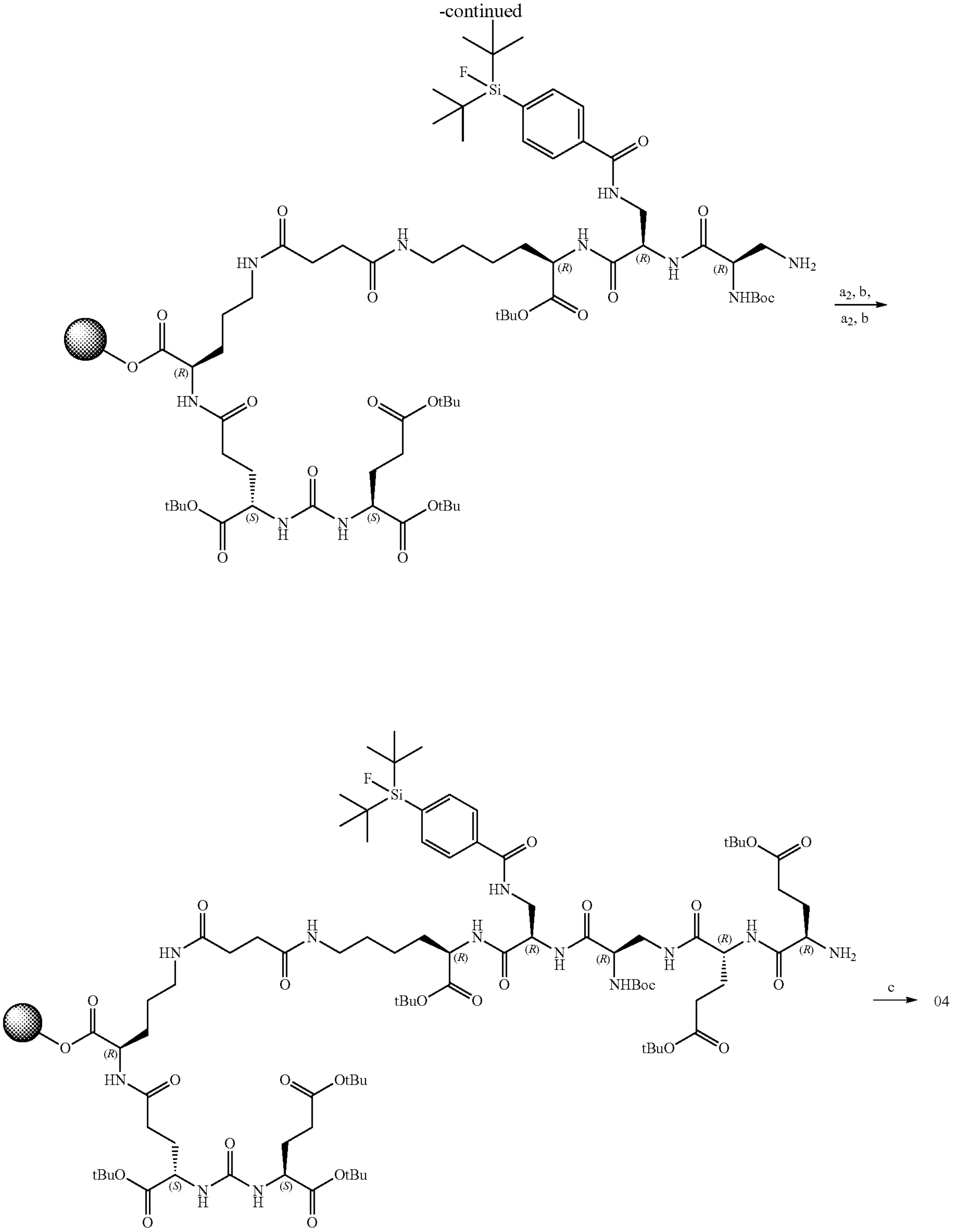

$a_1$) Boc-D-Dap(Fmoc)-OH, HOAt, TBTU, sym-collidine, (DMF); $a_2$) Fmoc-D-Glu(OtBu)-OH, HOAt, TBTU, sym-collidine, (DMF); b) 20% Pip in DMF; c) 95% TFA/2.5% TIPS/2.5% water.

SiFA-PSMA ligand with peptide-based modifier 04 was synthesized according to the general procedures for SPPS (Scheme 14). Shortly, resin-bound peptide XI was coupled with Boc-D-Dap(Fmoc)-OH (GSP3a) and the peptide was Fmoc-deprotected (GSP2). The resulting $N^{\beta}$-amine was afterwards coupled with Fmoc-D-Glu(OtBu)-OH (GSP3a) and the peptide was again Fmoc-deprotected (GSP2). This procedure was repeated one more time. The ligand was finally cleaved from the resin under removal of acid-labile protecting groups (GSP5) and purified via prep. RP-HPLC affording SiFA-PSMA ligand 04 as a colorless solid.

04
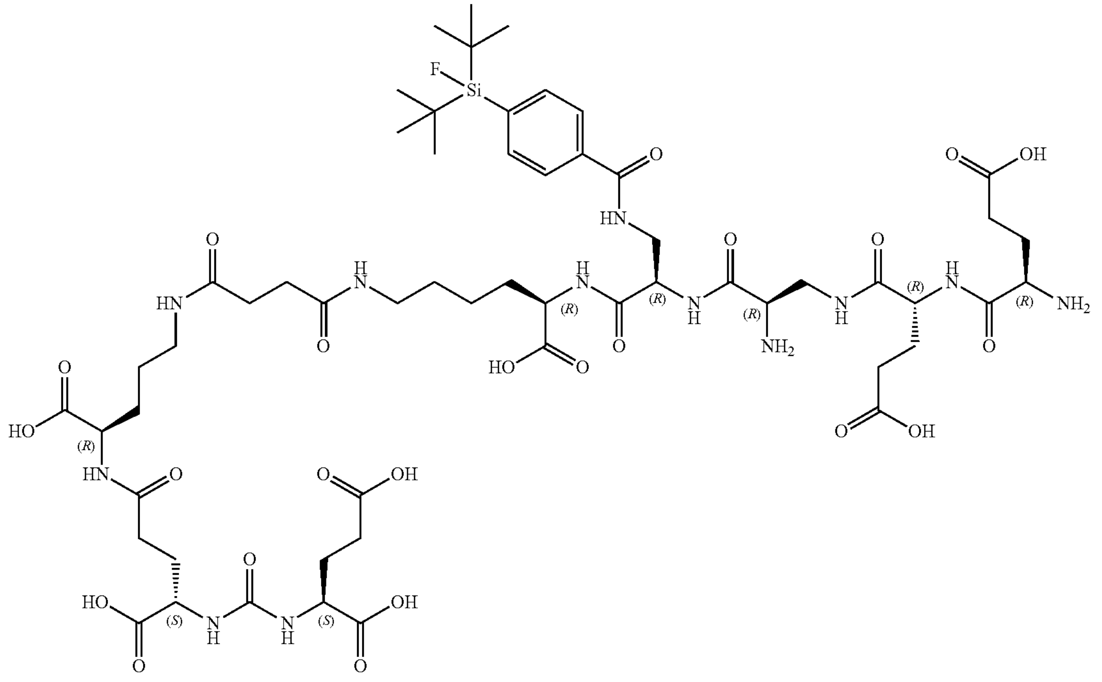
04: prep. RP-HPLC (column IV, 32-40% B in A, 20 min, λ=220 nm): $t_R$=13.2 min; yield: 4.87 mg (3.07 μmol, 27%); anal. RP-HPLC (column II, 10-70% B in A, 15 min, λ=220 nm): $t_R$=9.8 min; purity: 98%; MS (ESI, positive): m/z calc. m.i. mass ($C_{57}H_{89}FN_{12}O_{23}Si$): 1356.6, m/z found: 679.5 $[M+2H]^{2+}$, 1357.8 $[M+H]^+$.
2.8.9 Example 5: SiFA-PSMA Ligand 05
Scheme 15. Synthesis of SiFA-PSMA ligand 05
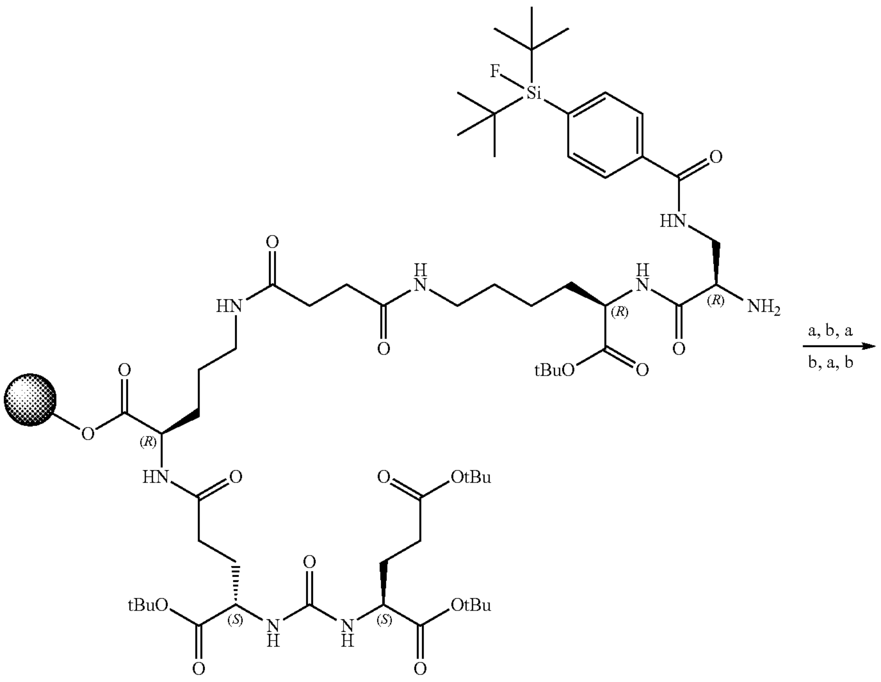
XI -continued

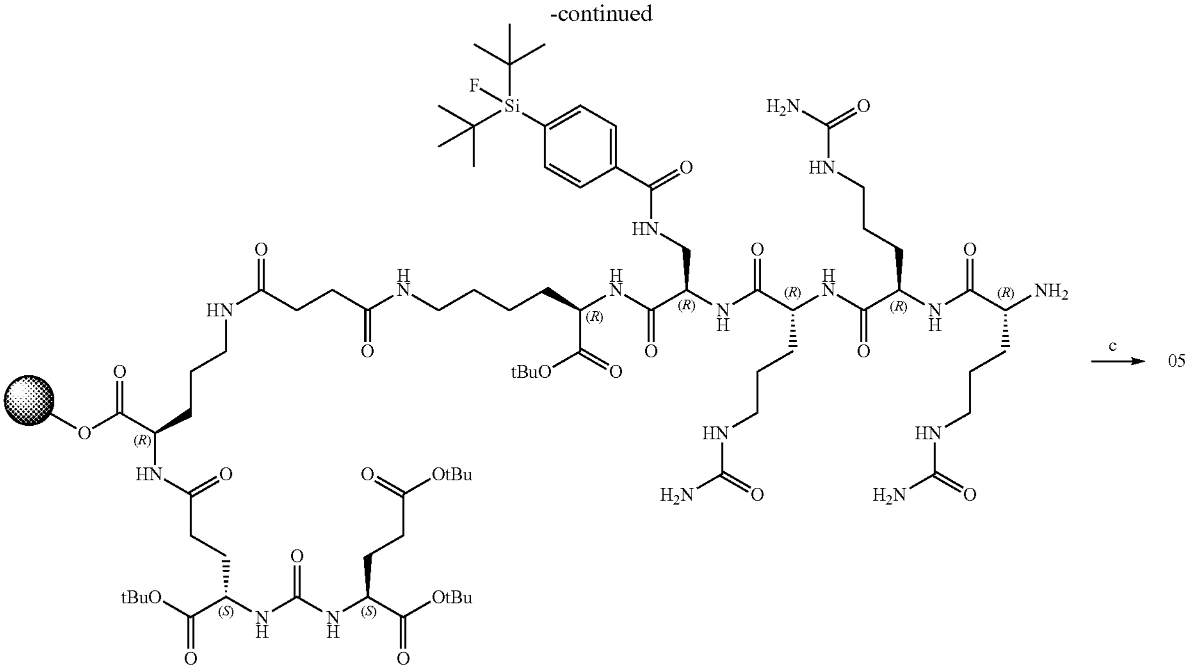

a) Fmoc-D-Cit-OH, HOAt, TBTU, sym-collidine, (DMF); b) 20% Pip in DMF; c) 95% TFA/2.5% TIPS/2.5% water.

SiFA-PSMA ligand 05 was synthesized according to the general procedures for SPPS (Scheme 15). In short, resin-bound peptide XI was coupled with Fmoc-D-Cit-OH (GSP3a) and the peptide was Fmoc-deprotected (GSP2). This procedure was repeated two more times. The ligand was finally cleaved from the resin under removal of acid-labile tBu-protecting groups (GSP5) and purified via prep. RP-HPLC yielding SiFA-PSMA ligand 05 as a colorless solid.

05

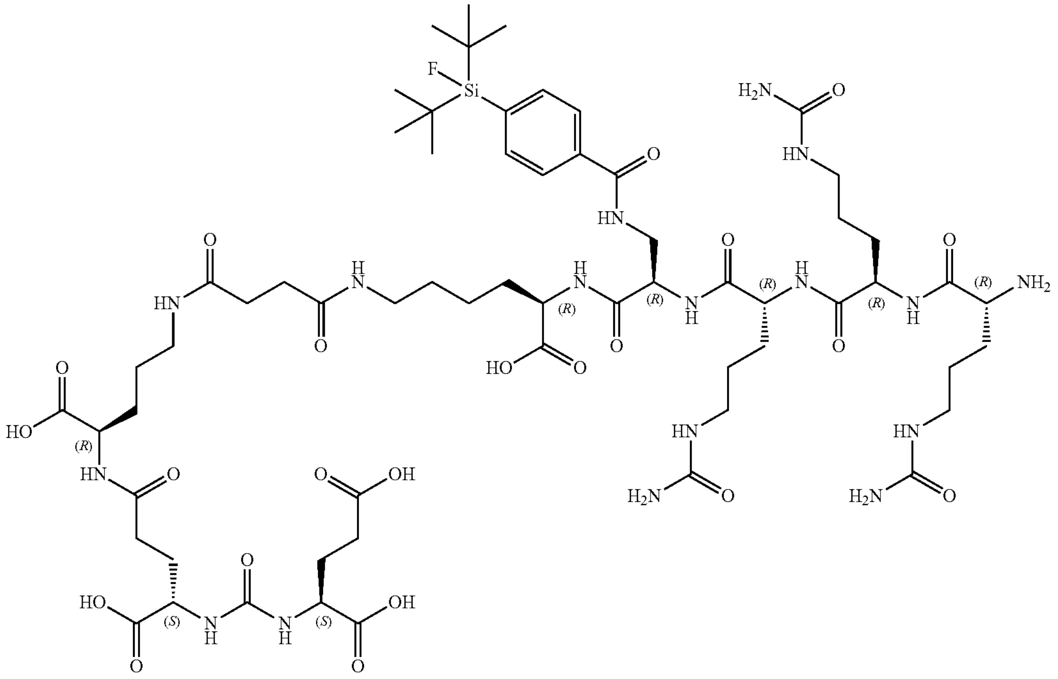

05: prep. RP-HPLC (column IV, 35-45% B in A, 20 min, λ=220 nm): $t_R$=8.3 min; yield: 7.56 mg (4.73 μmol, 36%); anal. RP-HPLC (column II, 10-70% B in A, 15 min, λ=220 nm): $t_R$=10.0 min; purity: 97%; MS (ESI, positive): m/z calc. m.i. mass ($C_{62}H_{102}FN_{17}O_{22}Si$): 1483.7, m/z found: 743.4 $[M+2H]^{2+}$, 1486.5 $[M+H]^{+}$.
2.8.10 Example 6: SiFA-PSMA Ligand 06
Scheme 16. Synthesis of SiFA-PSMA ligand 06
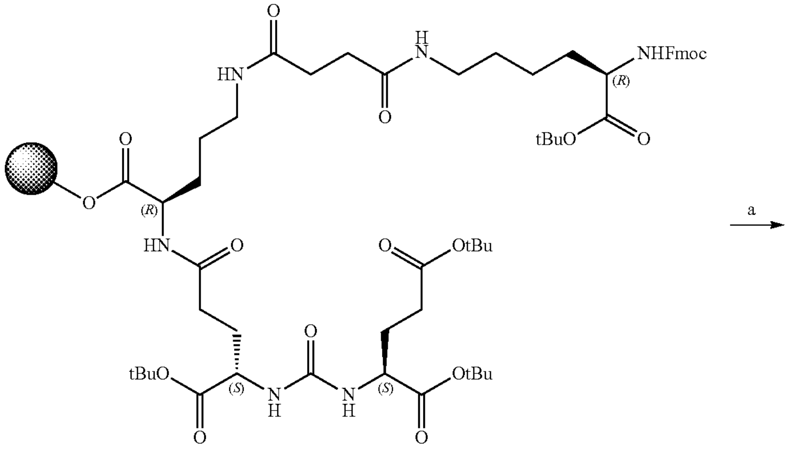
XVIII
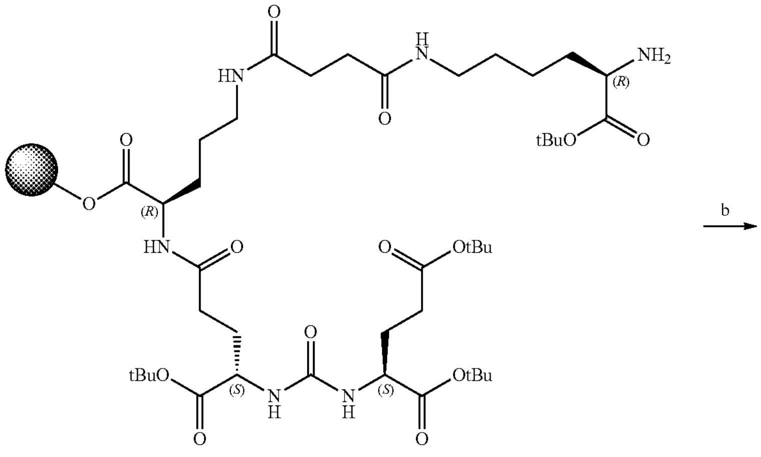

-continued

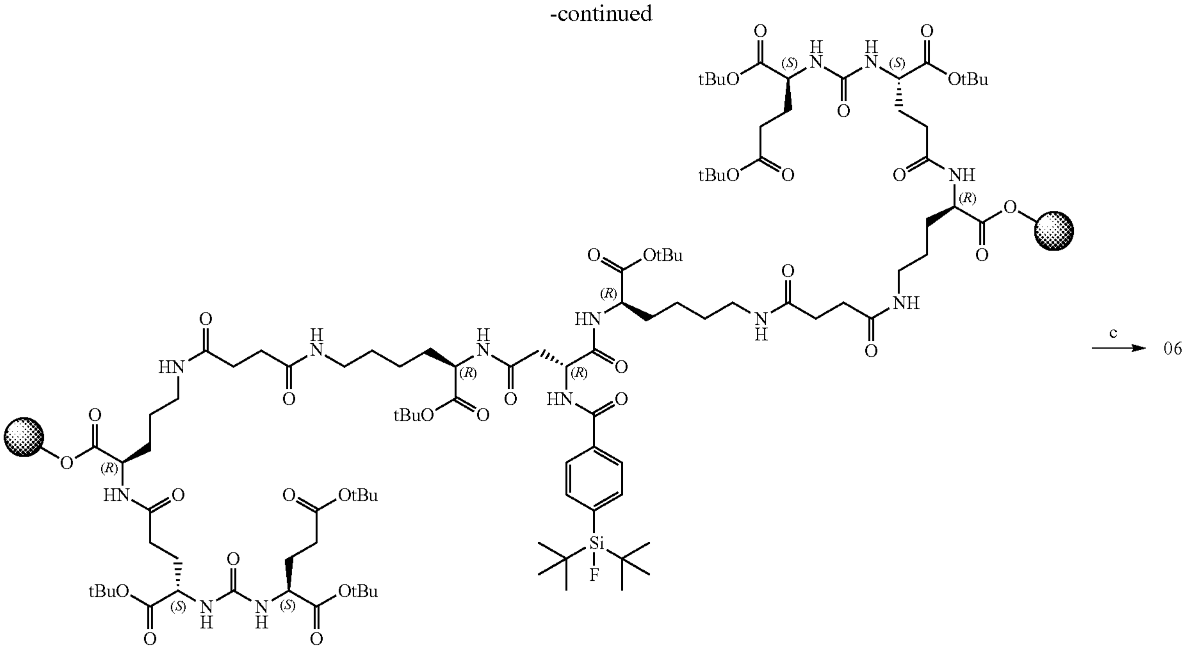

a) 20% Pip in DMF; b) SiFA-D-Asp(OH)-OH (XVII), HOAt, TBTU, sym-collidine, (DMF); c) 95% TFA/2.5% TIPS/2.5% water.

SiFA-PSMA ligand 06 was synthesized following the general synthesis procedures for SPPS (Scheme 16). Briefly, the resin-bound peptide XVIII was Fmoc-deprotected (GSP2) and subsequently coupled with SiFA-o-Asp(OH)—OH (XVII) (GSP3a) affording the dimerized ligand on the resin. The peptide was finally cleaved from the resin under removal of acid-labile tBu-protecting groups (GSP5) and purified via prep. RP-HPLC yielding SiFA-PSMA ligand 06 as a colorless solid.

06

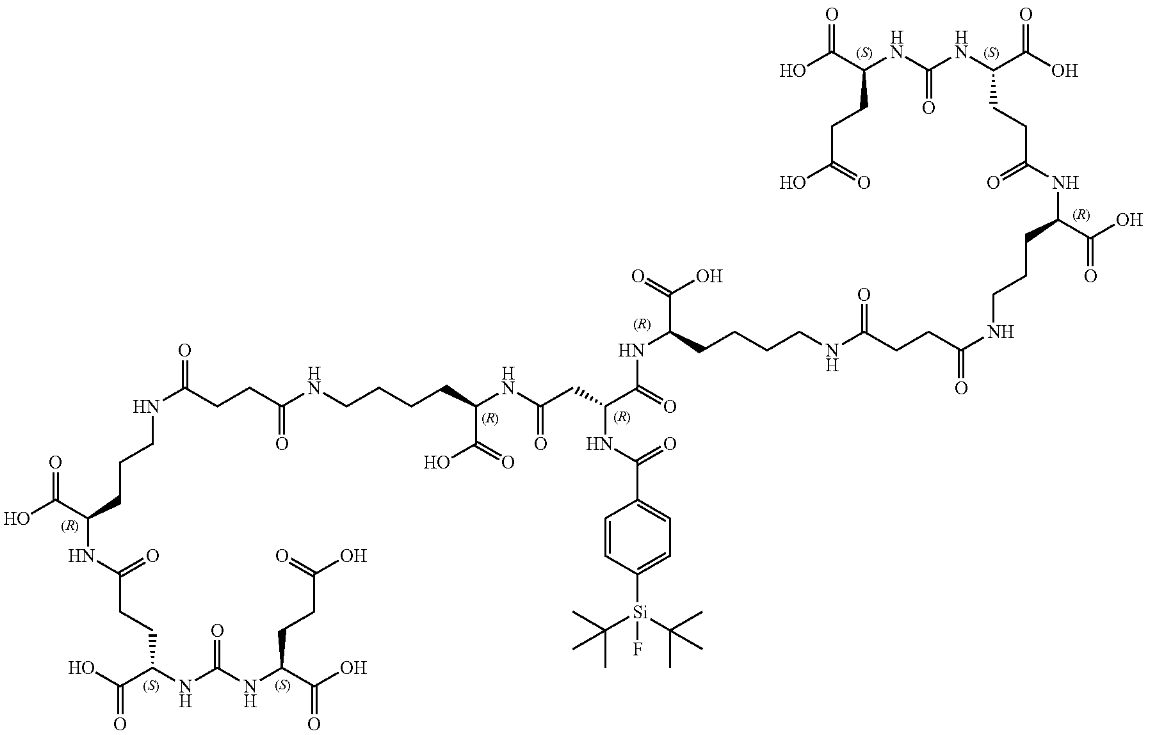

06: prep. RP-HPLC (column IV, 38-45% B in A, 20 min, λ=220 nm): $t_R$=7.6 min; yield: 3.42 mg (4.47 μmol, 14%); anal. RP-HPLC (column III, 10-70% B in A, 15 min, λ=220 nm): $t_R$=11.1 min; purity: 97%; MS (ESI, positive): m/z calc. m.i. mass ($C_{71}H_{108}FN_{13}O_{31}Si$): 1685.7, m/z found: 844.3 $[M+2H]^{2+}$, 1687.3 [M+H]1.
2.8.11 Example 7: SiFA-PSMA Ligand 07
Scheme 17. Synthesis of SiFA-PSMA ligand 07
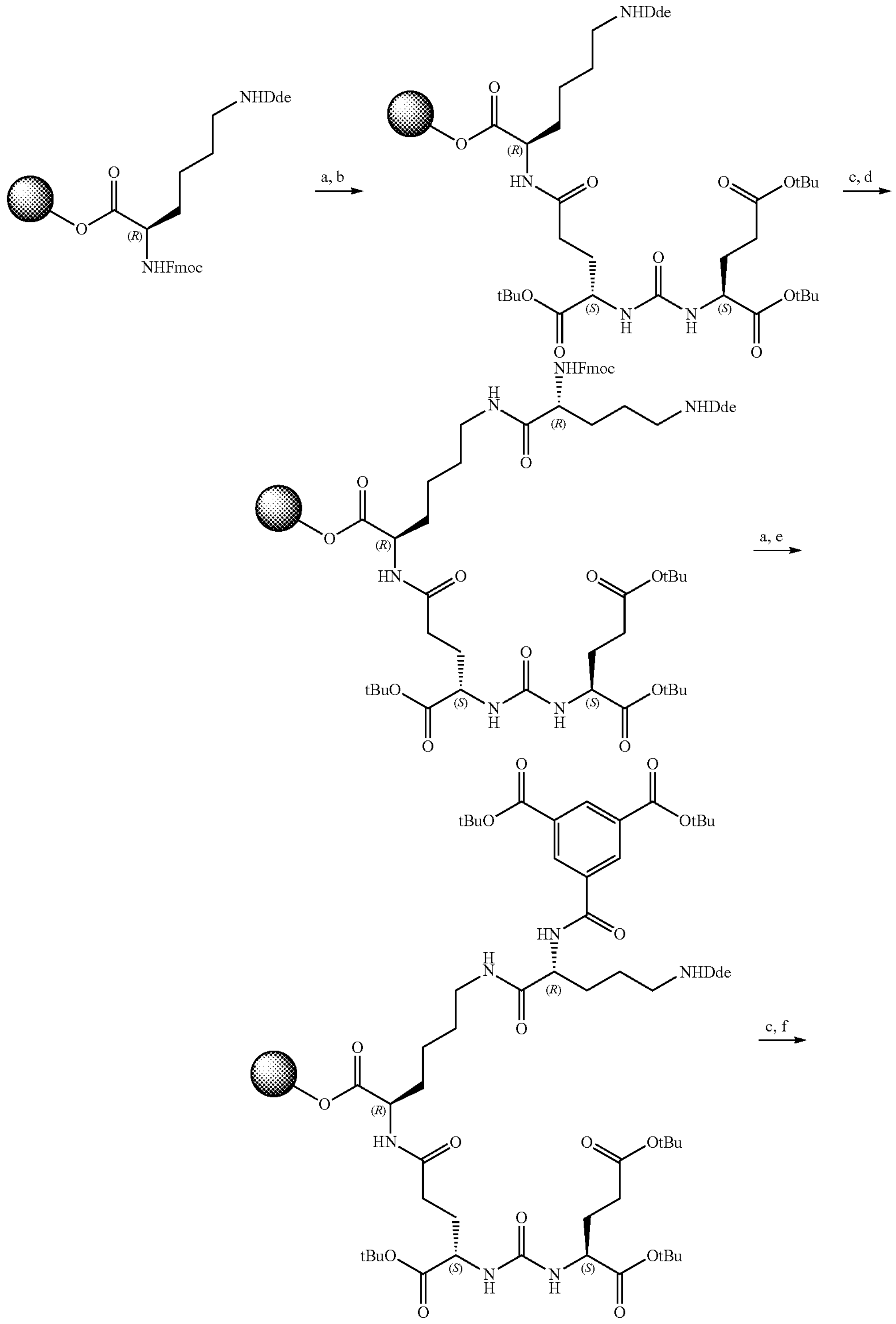

-continued

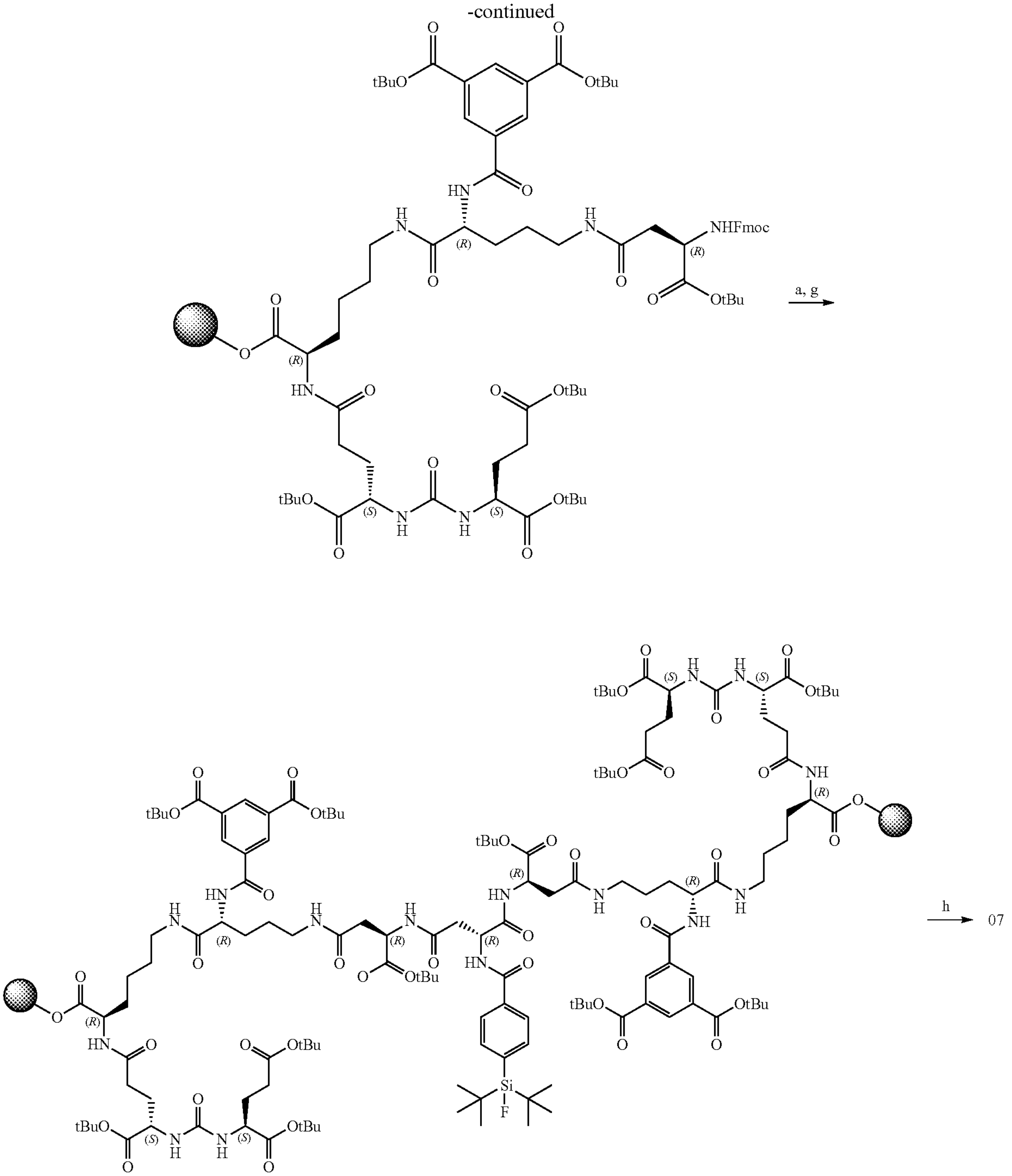

a) 20% Pip in DMF; b) tBuO-L-Glu(OtBu)-u-L-Glu-OtBu (VII), HOAt, TBTU, sym-collidine, (DMF); c) 2% hydrazine monohydrate in DMF; d) Fmoc-D-Orn(Dde)-OH, HOAt, TBTU, sym-collidine, (DMF); e) 3,5-bis(tert-butoxycarbonyl)benzoic acid (XVI), HOAt, TBTU, sym-collidine, (DMF); f) Fmoc-D-Asp(OH)-OtBu, HOAt, TBTU, sym-collidine, (DMF); g) SiFA-D-Asp(OH)-OH (XVII), HOAt, TBTU, sym-collidine, (DMF), h) 95% TFA/2.5% TIPS/2.5% water.

SiFA-PSMA ligand 07 was obtained following the general synthesis procedures for SPPS (Scheme 17). Therefore, 2-CTC-resin was loaded with Fmoc-D-Lys(Dde)-OH (GSP1). The amino acid was subsequently Fmoc-deprotected (GSP2) and coupled with tBuO-L-Glu(OtBu)-u-L-Glu-OtBu (VII) (GSP3a). After cleaving the Dde-protecting group (GSP4a), the resulting $N^{E}$-amine was coupled with Fmoc-D-Orn(Dde)-OH (GSP3a). Then, the resin-bound peptide was Fmoc-deprotected (GSP2) and elongated with 3,5-bis(tert-butoxycarbonyl)benzoic acid (XVI) (GSP3a). The Dde-protecting group was subsequently cleaved (GSP4a) and the resulting $N^{3}$-amine was coupled with Fmoc-D-Asp(OH)-OtBu (GSP3a). After Fmoc-deprotection (GSP2) the resin-bound peptide was coupled with SiFA-D-Asp(OH)—OH (XVII) (GSP3a) affording the dimerized ligand on the resin. The peptide was finally cleaved from the resin under removal of acid-labile tBu-protecting groups (GSP5) and purified via prep. RP-HPLC giving SiFA-PSMA ligand 07 as a colorless solid.

07

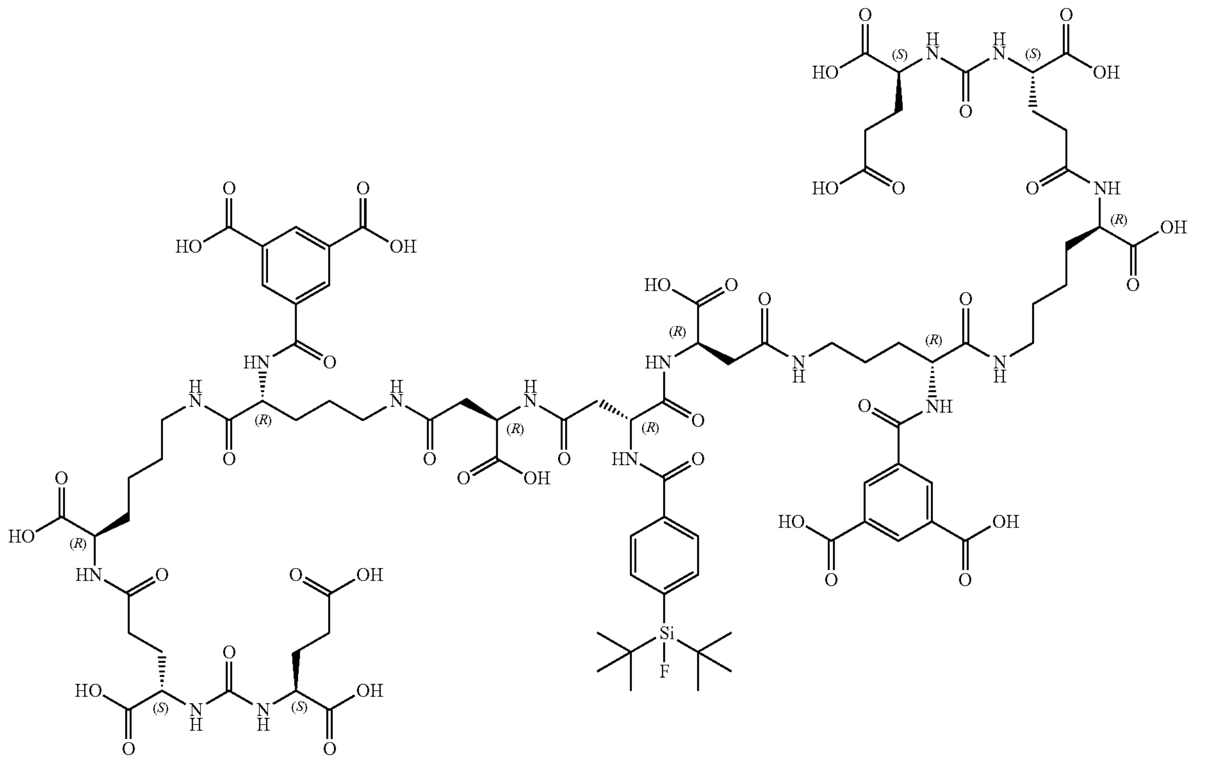

07: prep. RP-HPLC (column IV, 40-50% B in A, 20 min, λ=220 nm): $t_R$=7.5 min; yield: 10.5 mg (4.99 μmol, 25%); anal. RP-HPLC (column II, 10-70% B in A, 15 min, λ=220 nm): $t_R$=10.3 min; purity: 99%; MS (ESI, positive): m/z calc. m.i. mass ($C_{39}H_{118}FN_{15}O_{41}Si$): 2099.7, m/z found: 1050.7 $[M+2H]^{2}$+.

3. Results

3.1 Radiofluorination

The RCY for the radiofluorination of SiFA-PSMA ligands with urea- and peptide-based modifiers are summarized below (Table 2).

TABLE 2

RCY for $^{18}$F-labeling of SiFA-PSMA ligands with urea- and peptide-based modifiers (30 nmol, based on the final activity after purification in reference to the eluted activity from QMA as starting activity). Data are expressed as mean % ± SD.

| SiFA-PSMA ligand | RCY [%] |
|---|---|
| [$^{18}$F]01 a | 72 ± 3 (n = 2) |
| [$^{18}$F]01 b | 75 (n = 1) |
| [$^{18}$F]01 c | 38 (n = 1) |
| [$^{18}$F]01 d | 47 (n = 1) |
| [$^{18}$F]01 e | 42 (n = 1) |
| [$^{18}$F]01 f | 67 ± 7 (n = 4) |
| [$^{18}$F]01 g | 65 ± 3 (n = 3) |
| [$^{18}$F]01 h | 43 (n = 1) |
| [$^{18}$F]01 i | 56 (n = 1) |
| [$^{18}$F]01 j | 67 (n = 1) |
| [$^{18}$F]01 k | 41 (n = 1) |

TABLE 2-continued

RCY for $^{18}$F-labeling of SiFA-PSMA ligands with urea- and peptide-based modifiers (30 nmol, based on the final activity after purification in reference to the eluted activity from QMA as starting activity). Data are expressed as mean % ± SD.

| SiFA-PSMA ligand | RCY [%] |
|---|---|
| [$^{18}$F]02 a | 60 ± 11 (n = 5) |
| [$^{18}$F]02 b | 62 (n = 1) |
| [$^{18}$F]02 c | 55 ± 11 (n = 2) |
| [$^{18}$F]02 d | 34 (n = 1) |
| [$^{18}$F]02 e | 22 (n = 1) |
| [$^{18}$F]03 a | 34 (n = 1) |
| [$^{18}$F]03 b | 61 (n = 1) |
| [$^{18}$F]03 c | 44 (n = 1) |
| [$^{18}$F]03 d | 43 (n = 1) |
| [$^{18}$F]03 e | 64 ± 2 (n = 2) |
| [$^{18}$F]03 f | 57 ± 3 (n = 3) |
| [$^{18}$F]03 g | 31 (n = 1) |
| [$^{18}$F]03 h | 37 (n = 1) |
| [$^{18}$F]03 i | 40 ± 4 (n = 2) |
| [$^{18}$F]04 | 29 (n = 1) |
| [$^{18}$F]05 | 39 (n = 1) |
| [$^{18}$F]06 | 36 ± 3 (n = 2) |
| [$^{18}$F]07 | 36 (n = 1) |

3.2 Lipophilicity

TABLE 3

Determined $logD_{7.4}$ values of $^{18}F$-labeled SiFA-PSMA ligands with urea-based and peptide-based modifiers. Data are expressed as mean ± SD (n = 5).

| SiFA-PSMA ligand | $logD_{7.4}$ |
|---|---|
| [$^{18}$F]01 a | −4.02 ± 0.04 |
| [$^{18}$F]01 b | −4.04 ± 0.08 |
| [$^{18}$F]01 c | −3.72 ± 0.02 |
| [$^{18}$F]01 d | −3.28 ± 0.03 |
| [$^{18}$F]01 e | −3.96 ± 0.07 |
| [$^{18}$F]01 f | −3.65 ± 0.09 |
| [$^{18}$F]01 g | −3.71 ± 0.03 |
| [$^{18}$F]01 h | −3.71 ± 0.16 |
| [$^{18}$F]01 i | −3.96 ± 0.04 |
| [$^{18}$F]01 j | −3.86 ± 0.07 |
| [$^{18}$F]01 k | −2.99 ± 0.02 |
| [$^{18}$F]02 a | −3.65 ± 0.09 |
| [$^{18}$F]02 b | −3.70 ± 0.02 |
| [$^{18}$F]02 c | −3.27 ± 0.02 |
| [$^{18}$F]02 d | −3.24 ± 0.03 |
| [$^{18}$F]02 e | −3.50 ± 0.04 |
| [$^{18}$F]03 a | −3.80 ± 0.06 |
| [$^{18}$F]03 b | −3.85 ± 0.04 |
| [$^{18}$F]03 c | −3.31 ± 0.02 |
| [$^{18}$F]03 d | −3.42 ± 0.05 |
| [$^{18}$F]03 e | −3.40 ± 0.17 |
| [$^{18}$F]03 f | −3.43 ± 0.02 |
| [$^{18}$F]03 g | −3.56 ± 0.04 |
| [$^{18}$F]03 h | −3.66 ± 0.03 |
| [$^{18}$F]03 i | −2.30 ± 0.03 |
| [$^{18}$F]04 | −3.33 ± 0.11 |
| [$^{18}$F]05 | −3.17 ± 0.02 |
| [$^{18}$F]06 | −3.77 ± 0.04 |
| [$^{18}$F]07 | −3.45 ± 0.01 |

3.3 Binding Affinity to PSMA

TABLE 4

Determined binding affinities ($IC_{50}$) of synthesized SiFA-PSMA ligands with urea-based and peptide-based modifiers on LNCaP cells (150.000 cells/well) with [$^{125}$I]L-Glu-u-L-Lys(p-I-BA) (XII) [$IC_{50}$ = 7.9 ± 2.4 nM] as the reference (c = 0.2 nM, 1 h, 4° C., HBSS add. 1% BSA). Data are expressed as mean nM ± SD (n = 3).

| SiFA-PSMA ligand | $IC_{50}$ [nM] |
|---|---|
| 01 a | 7.8 ± 0.8 |
| 01 b | 11.8 ± 2.2 |
| 01 c | 17.0 ± 0.9 |
| 01 d | 13.0 ± 1.2 |
| 01 e | 9.2 ± 1.4 |
| 01 f | 8.3 ± 1.5 |
| 01 g | 8.7 ± 0.7 |
| 01 h | 8.7 ± 0.6 |
| 01 i | 8.8 ± 1.7 |
| 01 j | 9.2 ± 1.2 |
| 01 k | 29.4 ± 0.6 |
| 02 a | 10.2 ± 1.2 |
| 02 b | 5.6 ± 1.3 |
| 02 c | 5.9 ± 1.0 |
| 02 d | 9.9 ± 0.8 |
| 02 e | 9.0 ± 2.2 |
| 03 a | 9.3 ± 1.7 |
| 03 b | 8.8 ± 1.0 |
| 03 c | 11.7 ± 1.5 |
| 03 d | 9.1 ± 0.8 |
| 03 e | 8.5 ± 1.2 |
| 03 f | 6.9 ± 1.0 |
| 03 g | 11.9 ± 2.0 |
| 03 h | 10.7 ± 2.1 |
| 03 i | 20.6 ± 1.8 |
| 04 | 12.2 ± 1.9 |
| 05 | 16.2 ± 2.0 |
| 06 | 7.4 ± 1.9 |
| 07 | 5.5 ± 0.6 |

3.4 Internalization

TABLE 5

Determined internalized activities of $^{18}F$-labeled SiFA-PSMA ligands with urea-based and peptide-based modifiers (c = 0.5 nm) on LNCaP cells (125.000 cells/well) at 1 h in % of [$^{125}$I] L-Glu-u-L-Lys(p-I-BA) (XII) as the reference (c = 0.2 nm, 37° C., DMEM/F-12 add. 5% BSA). Data is corrected for non-specific binding (10 μm PMPA) and expressed as mean % ± SD (n = 3).

| SiFA-PSMA ligand | Internalization [%] |
|---|---|
| [$^{18}$F]01 a | 162.54 ± 7.08 |
| [$^{18}$F]01 b | 126.43 ± 4.23 |
| [$^{18}$F]01 c | 175.08 ± 5.93 |
| [$^{18}$F]01 d | 95.68 ± 9.86 |
| [$^{18}$F]01 e | 125.13 ± 1.14 |
| [$^{18}$F]01 f | 123.13 ± 2.14 |
| [$^{18}$F]01 g | 104.75 ± 4.37 |
| [$^{18}$F]01 h | 142.95 ± 7.49 |
| [$^{18}$F]01 i | 160.83 ± 2.72 |
| [$^{18}$F]01 j | 120.83 ± 0.92 |
| [$^{18}$F]01 k | 61.61 ± 1.33 |
| [$^{18}$F]02 a | 231.60 ± 14.21 |
| [$^{18}$F]02 b | 200.83 ± 3.32 |
| [$^{18}$F]02 c | 156.95 ± 13.21 |
| [$^{18}$F]02 d | 119.56 ± 5.84 |
| [$^{18}$F]02 e | 190.26 ± 16.87 |
| [$^{18}$F]03 a | 135.74 ± 6.70 |
| [$^{18}$F]03 b | 135.78 ± 5.50 |
| [$^{18}$F]03 c | 87.55 ± 2.28 |
| [$^{18}$F]03 d | 171.82 ± 9.57 |
| [$^{18}$F]03 e | 111.98 ± 3.90 |
| [$^{18}$F]03 f | 94.24 ± 6.01 |
| [$^{18}$F]03 g | 121.44 ± 3.72 |
| [$^{18}$F]03 h | 107.42 ± 3.66 |
| [$^{18}$F]03 i | 50.33 ± 2.97 |
| [$^{18}$F]04 | 124.49 ± 2.61 |
| [$^{18}$F]05 | 90.13 ± 6.13 |
| [$^{18}$F]06 | 270.03 ± 16.10 |
| [$^{18}$F]07 | 311.75 ± 7.30 |

3.5 Binding to HSA

The determined HSA binding values of SiFA-PSMA ligands with urea- and peptide-based modifiers are summarized below (Table 6).

TABLE 6

Determined HSA binding values of synthesized SiFA-PSMA ligands with urea-and peptide-based modifiers on a Chiralpak HSA column.

| SiFA-PSMA | ligand Binding to HSA [%] |
|---|---|
| 01 a | ≥99.0 |
| 01 b | ≥99.0 |
| 01 c | ≥98.9 |
| 01 d | ≥98.9 |
| 01 e | ≥99.0 |
| 01 f | 98.9 |
| 01 g | 98.9 |
| 01 h | 98.7 |
| 01 i | 98.9 |
| 01 j | ≥98.9 |
| 01 k | ≥98.9 |
| 02 a | ≥98.9 |
| 02 b | ≥98.9 |
| 02 c | ≥99.0 |
| 02 d | ≥98.9 |
| 02 e | ≥98.9 |
| 03 a | 98.8 |
| 03 b | 98.9 |
| 03 c | 98.6 |
| 03d | 97.2 |
| 03 e | 97.5 |
| 03 f | 96.9 |
| 03 g | 98.4 |
| 03 h | 97.8 |
| 03 i | 98.9 |
| 04 | 97.9 |
| 05 | 95.7 |
| 06 | ≥98.9 |

3.6 Properties of Known PSMA Inhibitors

The following Table 7 summarizes in vitro properties of known PSMA Inhibitors

TABLE 7

Comparison of PSMA binding affinitiy ($IC_{50}$), internalization (after 1 h) and $logP_{(o/w)}$ of established PSMA-targeting inhibitors.

| PSMA-targeting inhibitor | $logP_{(o/w)}$ | ($IC_{50}$) [nM] | Internalization (1 h) |
|---|---|---|---|
| [$^{nat}F/^{18}F$]DCFPyI[1] | −3.4 | 12.3 ± 1.2 | 118 ± 4 |
| [$^{nat}F/^{18}F$]PSMA-1007[1] | −1.6 | 4.2 ± 0.5 | 118 ± 5 |
| [$^{nat}Ga/^{68}Ga$]PSMA-11[2] | −4.1 ± 0.1 | 6.1 ± 0.8 | 91.1 ± 1.7 |
| [$^{68}Ga$]PSMA-617[3] | −4.30 ± 0.10 | — | — |
| [$^{nat}Ga/^{68}Ga$]PSMA I&T[4] | −4.3 ± 0.3 | 9.3 ± 3.3 | 59.2 ± 1.7 |

References in Table 7:
[1]S. Robu, A Schmidt, M. Eiber, M. Schottelius, T Günther, B.H. Yousefi, M. Schwaiger, H.-J. Wester. *EJNMMI research* 2018, 8, 30.
[2]M. Weineisen, J. Simecek, M. Schottelius, M. Schwaiger, H.-J. Wester, *EJNMMI research* 2014, 4, 63.
[3]C. A. Umbricht, M. Benešová, R. M. Schmid, A. Türler, R. Schibli, N. P. van der Meulen, C. Müller, *EJNMMI research* 2017, 7, 9.
[4]M. Wirtz, A. Schmidt, M. Schottelius, S. Robu, T, Günther, M. Schwaiger, H.-J. Wester, *EJNMMI research* 2018, 8, 84.

3.7 Biodistribution and Small-Animal μPET/CT Imaging

The determined biodistribution profiles of [$^{18}F$]01 a, [$^{18}F$]01 d, [$^{18}F$]02 c, [$^{18}F$]03 f, [$^{18}F$]06 and [$^{18}F$]07 at 1 h p.i. in LNCaP tumor-bearing CB17-SCID mice as well as representative PET/CT-images of [$^{18}F$]01 a at 1 h p.i. in LNCaP tumor-bearing CB17-SCID mice are summarized in FIGS. 2 to 8.

Figure 2:
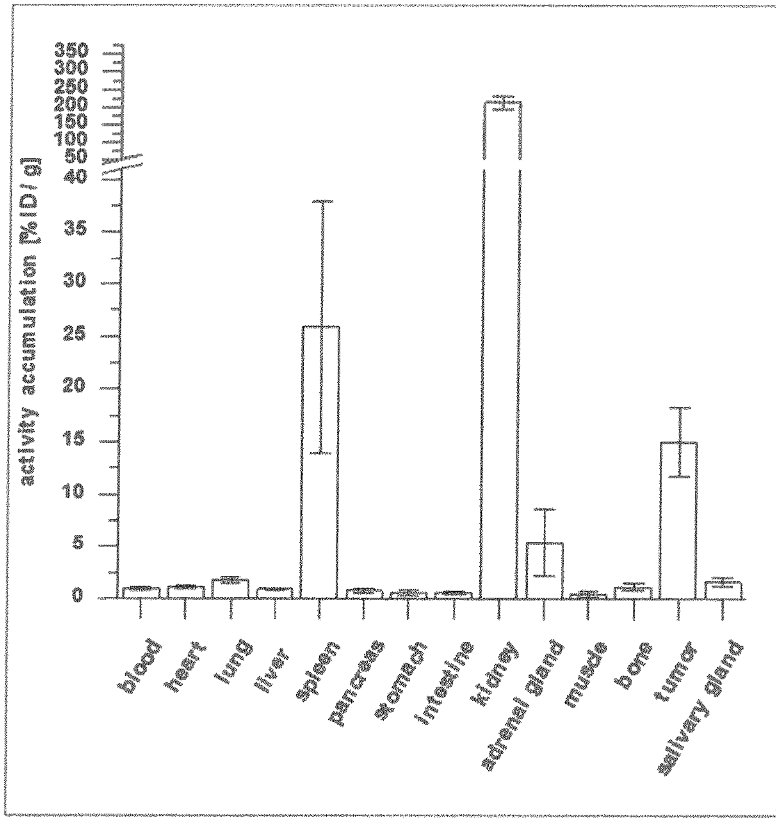

FIG. 2 shows the biodistribution profile of [$^{18}F$]01 a at 1 h p.i. in LNCaP tumor-bearing CB17-SCID mice. Data is expressed as mean % ID/g±SD (n=4).

Figure 3:
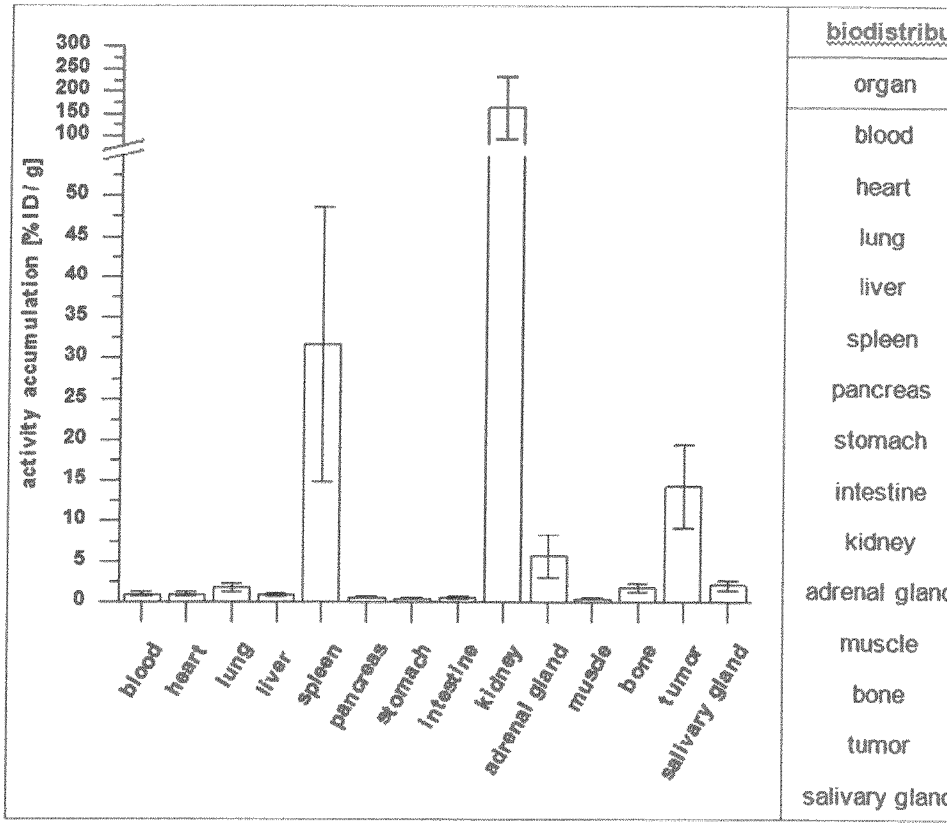
FIG. 3. Biodistribution profile of [$^{18}$F]01 d at 1 h p.i. in LNCaP tumor-bearing CB17-SCID mice. Data is expressed as mean % ID/g±SD (n=4).

FIG. 3 shows the biodistribution profile of [$^{18}F$]01 d at 1 h p.i. in LNCaP tumor-bearing CB17-SCID mice. Data is expressed as mean % ID/g±SD (n=4).

Figure 4:
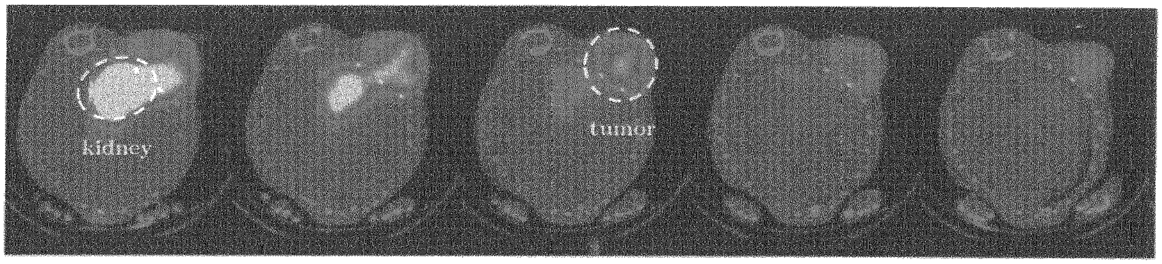
FIG. 4. Representative PET/CT-images (axial slices) of [$^{18}$F]01 a at 1 h p.i. in LNCaP tumor-bearing CB17-SCID mice (15 min acquisition time) and ROI of selected organs indicated by dashed lines.

FIG. 4 shows representative PET/CT-images (axial slices) of [$^{18}F$]01 a at 1 h p.i. in LNCaP tumor-bearing CB17-SCID mice (15 min acquisition time) and ROI of selected organs indicated by dashed lines.

Figure 5:
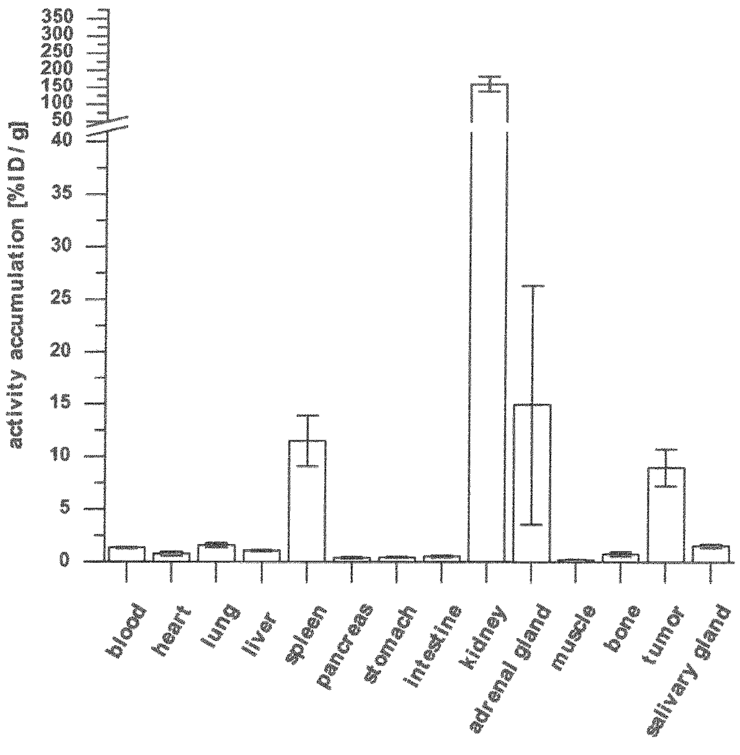
FIG. 5. Biodistribution profile of [$^{18}$F]02 c at 1 h p.i. in LNCaP tumor-bearing CB17-SCID mice. Data is expressed as mean % ID/g±SD (n=4).

FIG. 5 shows the biodistribution profile of [$^{18}F$]02 c at 1 h p.i. in LNCaP tumor-bearing CB17-SCID mice. Data is expressed as mean % ID/g±SD (n=4).

Figure 6:
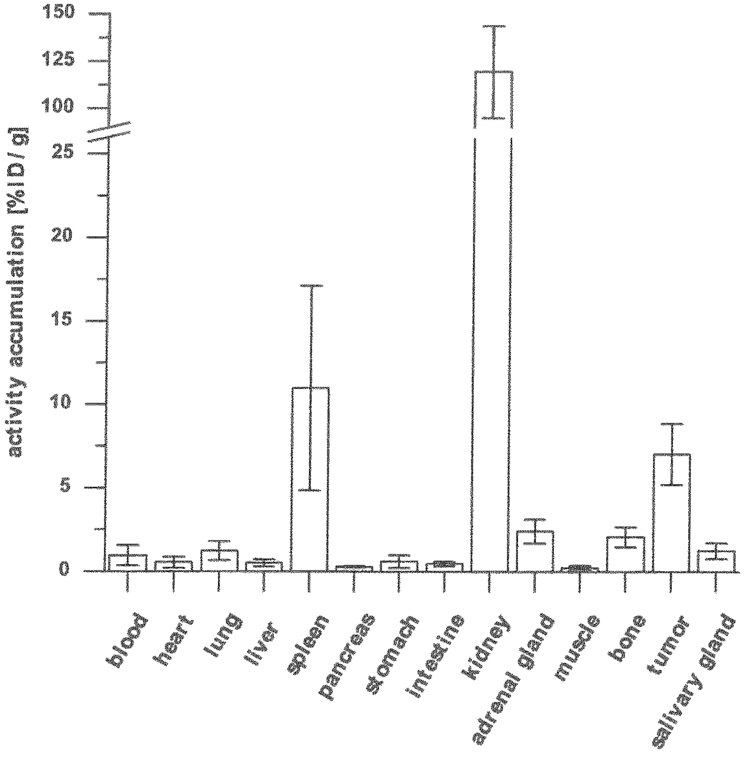
FIG. 6. Biodistribution profile of [$^{18}$F]03 f at 1 h p.i. in LNCaP tumor-bearing CB17-SCID mice. Data is expressed as mean % ID/g±SD (n=4).

FIG. 6 shows the biodistribution profile of [$^{18}F$]03 f at 1 h p.i. in LNCaP tumor-bearing CB17-SCID mice. Data is expressed as mean % ID/g±SD (n=4).

Figure 7:
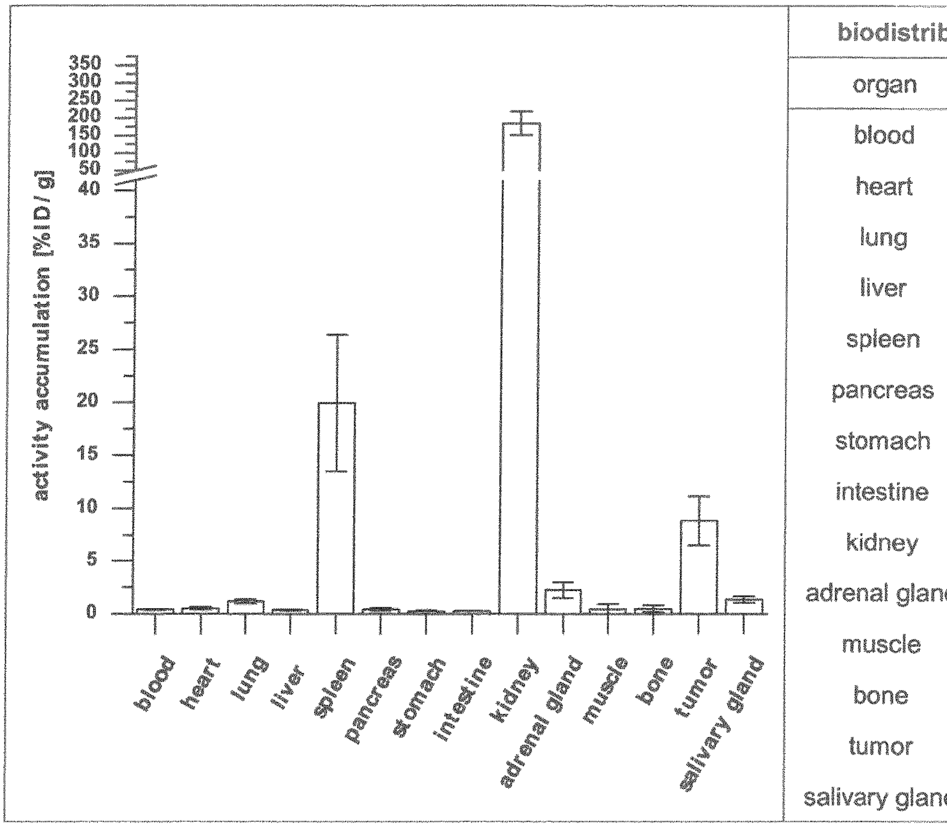
FIG. 7. Biodistribution profile of [$^{18}$F]06 at 1 h p.i. in LNCaP tumor-bearing CB17-SCID mice. Data is expressed as mean % ID/g±SD (n=4).

FIG. 7 shows the biodistribution profile of [$^{18}F$]06 at 1 h p.i. in LNCaP tumor-bearing CB17-SCID mice. Data is expressed as mean % ID/g±SD (n=4).

Figure 8:
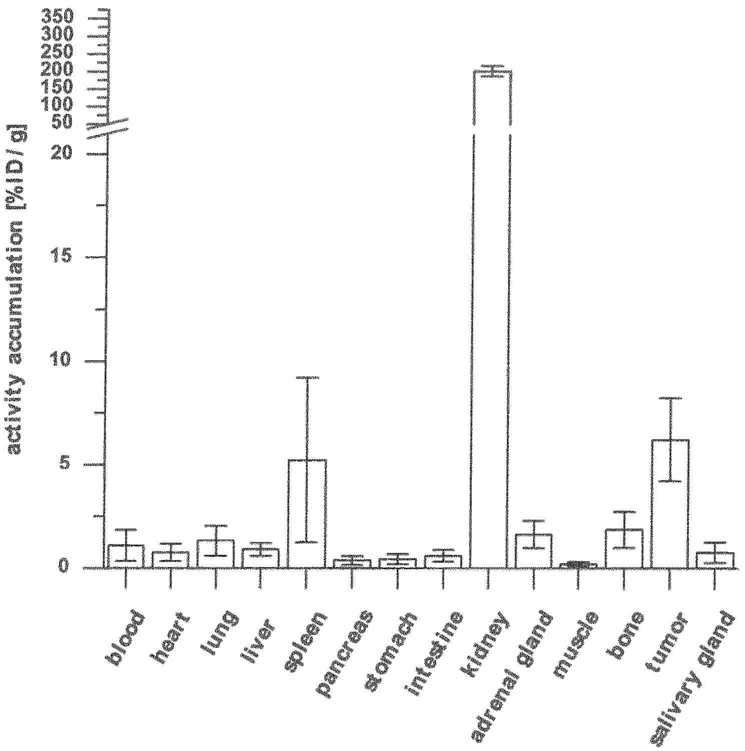
FIG. 8. Biodistribution profile of [$^{18}$F]07 at 1 h p.i. in LNCaP tumor-bearing CB17-SCID mice. Data is expressed as mean % ID/g±SD (n=5).

FIG. 8 shows the biodistribution profile of [$^{18}F$]07 at 1 h p.i. in LNCaP tumor-bearing CB17-SCID mice. Data is expressed as mean % ID/g±SD (n=5).

The invention claimed is:

1. A ligand-SiFA conjugate compound represented by formula (1)

(1)

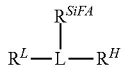

wherein:

$R^L$ is a ligand moiety which is capable of binding to prostate-specific membrane antigen (PSMA) and which has a structure represented by formula (6):

(6)

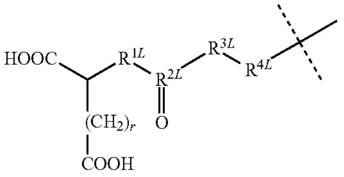

wherein r is an integer of 2 to 6;

$R^{1L}$ is $CH_2$, NH or O;

$R^{2L}$ is C or P(OH);

$R^{3L}$ is $CH_2$, NH or O;

$R^{4L}$ is a linear C1 to C7 alkanediyl group which carries a —COOH substituent;

and wherein the dashed line marks the bond which attaches the moiety to the remainder of the conjugate compound;

$R^{SiFA}$ has a structure represented by formula (7):

(7)

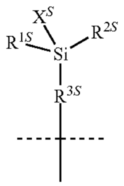

wherein $X^S$ is F, OH or H;

$R^{1S}$ and $R^{2S}$ are independently a linear or branched C3 to C10 alkyl group;

$R^{3S}$ is a C1 to C20 hydrocarbon group, wherein up to 3 carbon atoms may be replaced by a heteroatom selected from N, O and S;

and wherein the dashed line marks the bond which attaches the moiety to the remainder of the conjugate compound;

L is a linking moiety;

$R^H$ is a hydrophilic moiety which comprises (i) a linear or branched sequence of 2 to 10 hydrophilic amino acid units AH, each of which is independently derived from a natural or non-natural amino acid carrying a hydrophilic side chain, and optionally one amino acid unit AN derived from a natural or non-natural amino acid which is devoid of a hydrophilic side chain, wherein the hydrophilic amino acid units and, if present, the unit AN, are bound to each other via a direct covalent bond or via a coupling unit;

and which optionally further comprises (ii) one or more hydrophilic residues RT, each of which may be bound to an amino group, a carboxylic acid group, or to a functional group of a hydrophilic side chain of an amino acid unit;

or a pharmaceutically acceptable salt thereof.

2. The conjugate compound in accordance with claim 1, wherein the moiety —$R^H$ has the structure represented by formula (3A), (3B), (3C), (3D) or (3G):

$$-\left[X^{1H}-A^{1H}\right]_{b1}-X^{2H}-A^{2H} \quad (3A)$$

$$-\left[X^{1H}-A^{1H}\right]_{b1}-X^{3H}-A^{3H}-R^T \quad (3B)$$

$$-A^{1N}-\left[X^{1H}-A^{1H}\right]_{c1}-X^{2H}-A^{2H} \quad (3C)$$

$$-A^{1N}-\left[X^{1H}-A^{1H}\right]_{c1}-X^{3H}-A^{3H}-R^T \quad (3D)$$

wherein b1 is an integer of 1 to 9;

c1 is an integer of 1 to 9;

$A^{1H}$, independently for each occurrence, is a hydrophilic amino acid unit derived from a natural or non-natural amino acid carrying a hydrophilic side chain;

$A^{2H}$ and $A^{3H}$ are each independently a hydrophilic amino acid unit derived from a natural or non-natural amino acid carrying a hydrophilic side chain;

$A^{1N}$ is an amino acid unit derived from an amino acid which is devoid of a hydrophilic side chain;

$X^{1H}$, independently for each occurrence, is a bond or a coupling unit, $X^{2H}$ and $X^{3H}$ are each independently a bond or a coupling unit, and $R^T$ represents a hydrophilic residue which may be bound to an amino group, a carboxylic acid group, or to a functional group of a hydrophilic side chain of the amino acid unit $A^{3H}$;

or a pharmaceutically acceptable salt thereof;

(3G)

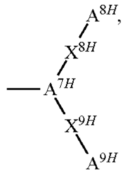

wherein $A^{7H}$, $A^{8H}$ and $A^{9H}$ are each independently a hydrophilic amino acid unit derived from a natural or non-natural amino acid carrying a hydrophilic side chain; and $X^{8H}$ and $X^{9H}$ are each independently a direct bond or a coupling unit;

and optionally a hydrophilic residue $R^T$ may be bound to an amino group, a carboxylic acid group, or to a functional group of a hydrophilic side chain of one or both of the amino acid units $A^{8H}$ and $A^{9H}$;

or a pharmaceutically acceptable salt thereof.

3. The conjugate compound in accordance with claim 1, wherein the moiety —$R^H$ has the structure represented by formula (3E) or (3F):

$$-A^{4H}-X^{4H}-A^{5H}-X^{5H}-A^{6H} \quad (3E),$$

$$-A^{1N}-X^{4H}-A^{5H}-X^{5H}-A^{6H} \quad (3F)$$

wherein $A^{4H}$, $A^{5H}$ and $A^{6H}$ are each independently a hydrophilic amino acid unit derived from a natural or non-natural amino acid carrying a hydrophilic side chain;

$X^{4H}$ and $X^{5H}$ are each independently a direct bond or a coupling unit, and optionally a hydrophilic residue $R^T$ may be bound to an amino group, a carboxylic acid group, or to a functional group of a hydrophilic side chain of the amino acid unit $A^{6H}$; and $A^{1N}$ is an amino acid unit derived from an amino acid devoid of a hydrophilic side chain;

or a pharmaceutically acceptable salt thereof.

4. The conjugate compound in accordance with claim 1, wherein the hydrophilic moiety $R^T$ is selected from a chelator group, a chelate group with a complexed metal or radiometal, a carbohydrate residue, a polyethylene glycol residue, a reduced amino acid and an amino acid analogue with a carboxylic acid isoster;

or a pharmaceutically acceptable salt thereof.

5. The conjugate compound in accordance with claim 1, wherein the hydrophilic amino acid units are, each independently, derived from an amino acid carrying a hydrophilic side chain which comprises at least one hydrophilic functional group selected from an amino group, a carboxylic acid group, a hydroxy group, a guanidino group, an amido group and a urea group or from isosters of these groups;

or a pharmaceutically acceptable salt thereof.

6. The conjugate compound according to claim 1, wherein the hydrophilic amino acid units in $R^H$ are each independently derived from an amino acid selected from 2,3-diaminopropionic acid (Dap), 2,4-diaminobutanoic acid (Dab), ornithine (Orn), lysine (Lys), 4-aminopiperidine-4-carboxylic acid (Apc4), 3-aminopiperidine-3-carboxylic acid (Apc3), 2-aminopiperidine-2-carboxylic acid (Apc2), aspartic acid (Asp), homoglutamic acid (Hgl), glutamic acid (Glu), 2,3-diaminosuccinic acid, diaminopentanedioic acid, diaminohexanedioic acid, diaminoheptanedioic acid, diaminooctanedioic acid, threonine (Thr) and citrulline (Cit);

or a pharmaceutically acceptable salt thereof.

7. The conjugate compound in accordance with claim 1, wherein any amino acid unit derived from an amino acid devoid of a hydrophilic side chain in the moiety —$R^H$ is derived from an amino acid selected from glycine (Gly), phenylalanine (Phe), β-alanine (β-Ala) and aminohexanoic acid (Ahx);

or a pharmaceutically acceptable salt thereof.

8. The conjugate compound in accordance with claim 1, wherein the ligand moiety $R^L$ has a structure represented by formula (6A), (6B), (6C) or (6D):

(6A)

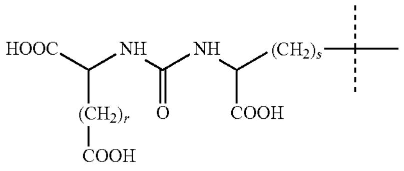

(6B)

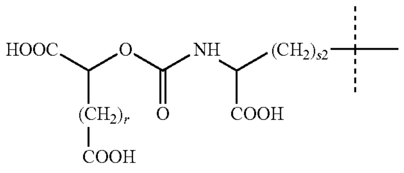

(6C)

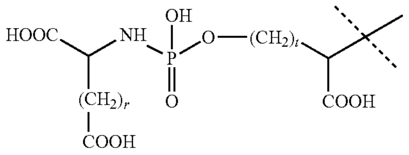

6D)

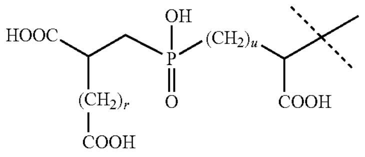

wherein r is an integer of 2 to 6;

s is an integer of 2 to 6;

s2 is an integer of 2 to 6;

t is an integer of 1 to 4;

u is an integer of 1 to 4;

and wherein the dashed line marks the bond which attaches the moiety to the remainder of the conjugate compound;

or a pharmaceutically acceptable salt thereof.

9. The conjugate compound in accordance with claim 1, which is represented by formula (1A):

(1A)

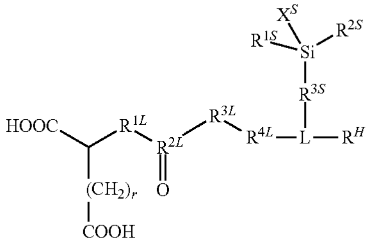

wherein $R^H$ and L are defined as in claim 1;

r is an integer of 2 to 6;

$R^{1L}$ is $CH_2$, NH or O;

$R^{2L}$ is C or P(OH);

$R^{3L}$ is $CH_2$, NH or O;

$R^{4L}$ is a linear C1 to C7 alkanediyl group which carries a —COOH substituent;

$X^S$ is F, OH or H;

$R^{1S}$ and $R^{2S}$ are independently a linear or branched C3 to C10 alkyl group; and $R^{3S}$ is a C1 to C20 hydrocarbon group, wherein up to 3 carbon atoms may be replaced by a heteroatom selected from N, O and S;

or a pharmaceutically acceptable salt thereof.

10. The conjugate compound in accordance with claim 9, which is represented by formula (1G) or (1H):

(1G)

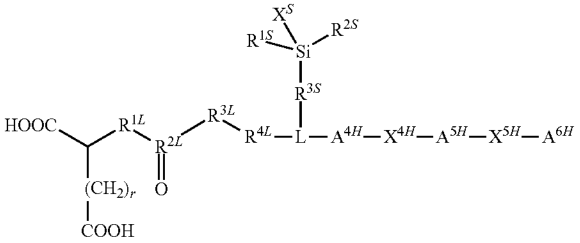

(1H)

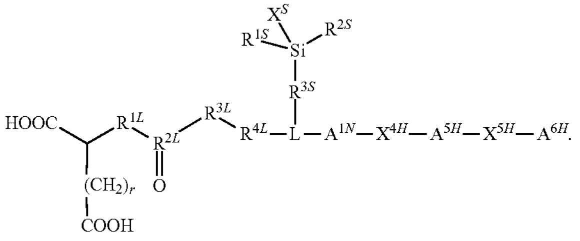

wherein $R^{1L}$, $R^{2L}$, $R^{3L}$, RAL, $R^{1S}$, $R^{2S}$, $R^{3S}$, $X^S$; $R^H$, L and r are defined as in claim 9;

$A^{4H}$, $A^{5H}$ and $A^{6H}$ are each independently a hydrophilic amino acid unit derived from a natural or non-natural amino acid carrying a hydrophilic side chain;

$X^{4H}$ and $X^{5H}$ are each independently a direct bond or a coupling unit, and optionally a hydrophilic residue $R^T$ may be bound to an amino group, a carboxylic acid group, or to a functional group of a hydrophilic side chain of the amino acid unit $A^{6H}$; and $A^{1N}$ is an amino acid unit derived from an amino acid devoid of a hydrophilic side chain;

or a pharmaceutically acceptable salt thereof.

11. The conjugate compound in accordance with claim 1, wherein the linking moiety L has a structure represented by formula (8A) or (8B):

(8A)

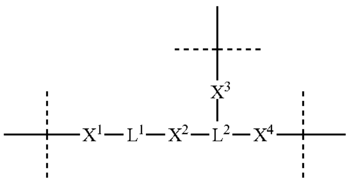

-continued (8B)

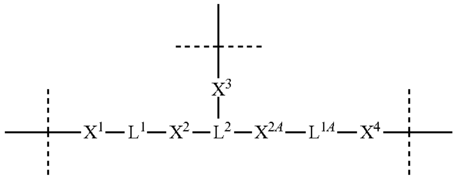

wherein the bond marked with a dashed line at $X^1$ is formed with $R^L$, the bond marked with a dashed line at $X^3$ is formed with $R^{SiFA}$, and the bond marked with a dashed line at $X^4$ is formed with $R^H$;

$X^1$ is selected from an amide bond, an ether bond, a thioether bond, an ester bond, a thioester bond, a urea bond, a thiourea bond and an amine bond;

$X^2$ is selected from an amide bond, an ether bond, a thioether bond, an ester bond, a thioester bond, a urea bond, a thiourea bond and an amine bond;

$X^{2A}$ is selected from an amide bond, an ether bond, a thioether bond, an ester bond, a thioester bond, a urea bond, a thiourea bond and an amine bond;

$X^3$ is selected from an amide bond, an ester bond, an ether bond, an amine bond, and a linking group of the formula:

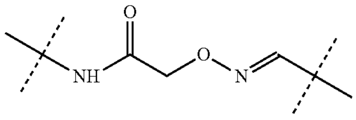, wherein the bond marked with a dashed line at the NH group is formed with $L^2$ and the other bond marked with a dashed line is formed with $R^{SiFA}$;

$X^4$ is a group which forms, in combination with a —NH— group or —C(O)— group contained in an amino acid unit of —$R^H$, or taken in combination with a coupling unit contained in $R^H$, an amide bond, an ester bond, a thioester bond, or a urea bond;

$L^1$ is a divalent linking group comprising a continuous chain of 6 to 36 atoms extending from $X^1$ to $X^2$, wherein said chain is formed by carbon atoms and optional heteroatoms which are selected, independently for each occurrence if more than one heteroatom is present, from N, O and S, and wherein the chain may comprise one or more divalent cyclic or heterocyclic groups, in which case all of the ring atoms are counted as atoms of the continuous chain;

$L^{1A}$ is a divalent linking group comprising a continuous chain of 6 to 24 atoms extending from $X^2A$ to $X^4$, wherein said chain is formed by carbon atoms and optional heteroatoms which are selected, independently for each occurrence if more than one heteroatom is present, from N, O and S, and wherein the chain may comprise one or more divalent cyclic or heterocyclic groups, in which case all of the ring atoms are counted as atoms of the continuous chain; and $L^2$ is a trivalent moiety;

or a pharmaceutically acceptable salt thereof.

12. The conjugate compound in accordance with claim 11, wherein $L^2$ is represented by formula (9):

(9)

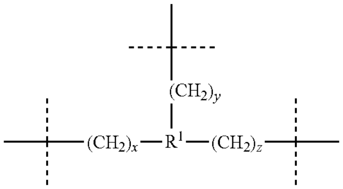

wherein $R^1$ is selected from N, $CR^2$, wherein $R^2$ is H or C1-C6 alkyl, and from a 5 to 7 membered carbocyclic or heterocyclic group;

the bond marked by the dashed line at $(CH_2)_x$ is formed with $X^2$, and x is an integer of 0 to 4;

the bond marked by the dashed line at $(CH_2)_y$ is formed with $X^3$, and y is an integer of 0 to 4; and the bond marked by the dashed line at $(CH_2)_z$ is formed with $X^4$ or $X^{2A}$, respectively, and z is an integer of 0 to 4;

or a pharmaceutically acceptable salt thereof.

13. The conjugate compound in accordance with claim 11, wherein the linking moiety L has a structure represented by formula (10A) or (10B):

(10A)

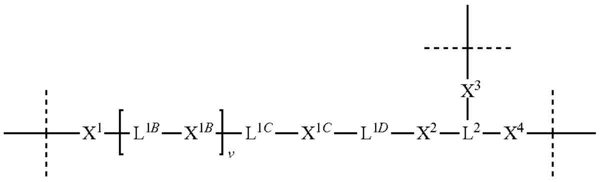

(10B)

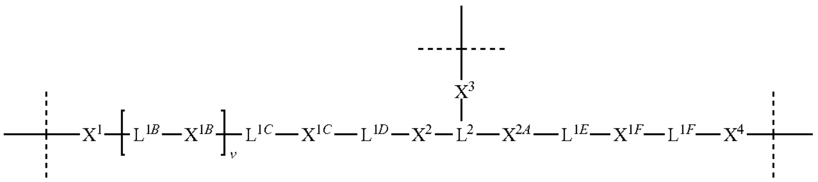

wherein:

$X^1$, $X^2$, $X^{2A}$, $X^3$, $X^4$ and $L^2$ are as defined in claim 11;

v is 0 or 1;

$L^{1B}$ is an optionally substituted C1-C8 alkanediyl group, which may be interrupted by an ether bond and wherein, if the alkanediyl group comprises a chain of 4 or more carbon atoms, 4 consecutive carbon atoms in the chain may be replaced by a benzenediyl group or a cyclohexanediyl group;

$L^{1C}$ and $L^{1F}$ are independently an optionally substituted C1-C8 alkanediyl group, which may be interrupted by an ether bond and wherein, if the alkanediyl group comprises a chain of 4 or more carbon atoms, 4 consecutive carbon atoms in the chain may be replaced by a benzenediyl group or a cyclohexanediyl group;

$L^{1D}$ and $L^{1E}$ are independently an optionally substituted C1-C8 alkanediyl group, which may be interrupted by an ether bond and wherein, if the alkanediyl group comprises a chain of 4 or more carbon atoms, 4 consecutive carbon atoms in the chain may be replaced by a benzenediyl group or a cyclohexanediyl group;

$X^{1B}$ is selected from an amide bond, an ether bond, a thioether bond, an ester bond, a thioester bond, a urea bond, a thiourea bond and an amine bond; and $X^{1C}$ and $X^{1F}$ are independently selected from an amide bond, an ether bond, a thioether bond, an ester bond, a thioester bond, a urea bond, a thiourea bond and an amine bond;

or a pharmaceutically acceptable salt thereof.

14. A pharmaceutical or diagnostic composition comprising or consisting of one or more conjugate compounds or salts in accordance with claim 1.

15. A conjugate compound or salt in accordance with claim 1 for use in a method of diagnosing, treating, or diagnosing and treating (a) cancer; or (b) neoangiogenesis/angiogenesis.

16. The conjugate compound in accordance with claim 1, wherein, in formula (7)

$R^{1S}$ and $R^{2S}$ are tert-butyl; and $R^{3S}$ is a phenyl ring;

or a pharmaceutically acceptable salt thereof.

* * * * *